(12) United States Patent
Henry et al.

(10) Patent No.: US 6,917,887 B2
(45) Date of Patent: Jul. 12, 2005

(54) DIGITAL FLOWMETER

(75) Inventors: Manus P. Henry, England (GB); David W. Clarke, England (GB); James H. Vignos, Needham Heights, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 10/637,620

(22) Filed: Aug. 11, 2003

(65) Prior Publication Data

US 2004/0031328 A1 Feb. 19, 2004

Related U.S. Application Data

(63) Continuation of application No. 09/931,057, filed on Aug. 17, 2001, now Pat. No. 6,754,594, which is a continuation of application No. 09/111,739, filed on Jul. 8, 1998, now Pat. No. 6,311,136.

(60) Provisional application No. 60/066,554, filed on Nov. 26, 1997.

(51) Int. Cl.[7] .......................... G01F 1/00; G01F 23/00; G01F 1/84

(52) U.S. Cl. ................ 702/45; 73/861.355; 73/861.356

(58) Field of Search ............................ 702/45–47, 100, 702/104–106; 73/861.355–861.357

(56) References Cited

U.S. PATENT DOCUMENTS

| | | | |
|---|---|---|---|
| 3,956,682 A | 5/1976 | Van Dyck | 318/640 |
| RE29,383 E | 9/1977 | Gallatin et al. | 137/14 |
| 4,187,721 A * | 2/1980 | Smith | 73/861.356 |
| 4,358,822 A | 11/1982 | Sanchez | 700/31 |
| RE31,450 E | 11/1983 | Smith | 73/861.356 |
| 4,419,898 A | 12/1983 | Zanker et al. | 73/861.02 |
| 4,422,338 A | 12/1983 | Smith | 73/861.356 |
| 4,491,025 A | 1/1985 | Smith et al. | 73/861.355 |
| 4,688,418 A | 8/1987 | Cheung et al. | 73/29.01 |

(Continued)

FOREIGN PATENT DOCUMENTS

| | | |
|---|---|---|
| EP | 0696726 A | 2/1996 |
| EP | 0 698 783 A1 | 2/1996 |
| EP | 0 702 212 A2 | 3/1996 |
| EP | 0827096 | 3/1998 |
| WO | WO 93/21505 | 10/1993 |
| WO | WO 00/10059 | 2/2000 |
| WO | WO 02/08703 | 1/2002 |

OTHER PUBLICATIONS

A.F. Skea, "Effects of Gas Leaks in Oil Flow on Single–Phase Flowmeters", *Flow Measurement and Instrumentation*, vol. 10, pp. 146–150 (1999).

(Continued)

*Primary Examiner*—Marc S. Hoff
*Assistant Examiner*—Manuel L. Barbee
(74) *Attorney, Agent, or Firm*—Fish & Richardson P.C.

(57) ABSTRACT

A flowmeter includes a vibratable conduit, a driver connected to the conduit and operable to impart motion to the conduit, and a sensor connected to the conduit and operable to sense the motion of the conduit. A control and measurement system is connected to the driver and the sensor. The control and measurement system includes circuitry to receive a sensor signal from the sensor, generate a drive signal based on the sensor signal, supply the drive signal to the driver, and generate a measurement of a property of material flowing through the conduit based on the sensor signal.

46 Claims, 71 Drawing Sheets

U.S. PATENT DOCUMENTS

| | | | |
|---|---|---|---|
| 4,727,746 A | 3/1988 | Mikasa et al. ............. 73/23.31 |
| 4,757,390 A | 7/1988 | Mehrgardt et al. ............ 386/34 |
| 4,773,257 A | 9/1988 | Aslesen et al. ............. 73/61.44 |
| 4,782,711 A | 11/1988 | Pratt ..................... 73/861.356 |
| 4,801,897 A | 1/1989 | Flecken ....................... 331/65 |
| 4,817,448 A | 4/1989 | Hargarten et al. ..... 73/861.356 |
| 4,823,614 A | 4/1989 | Dahlin .................. 73/861.357 |
| 4,852,395 A | 8/1989 | Kolpak ...................... 73/61.44 |
| 4,852,410 A * | 8/1989 | Corwon et al. ........ 73/861.355 |
| 4,879,911 A | 11/1989 | Zolock ................. 73/861.356 |
| 4,891,991 A | 1/1990 | Mattar et al. .......... 73/861.357 |
| 4,895,030 A | 1/1990 | Bergamini et al. ..... 73/861.355 |
| 4,911,006 A | 3/1990 | Hargarten et al. ............ 73/198 |
| 4,911,020 A | 3/1990 | Thompson ............. 73/861.356 |
| 4,934,195 A | 6/1990 | Hussain ................. 73/861.355 |
| 4,934,196 A | 6/1990 | Romano ............... 73/861.356 |
| 4,996,871 A | 3/1991 | Romano ...................... 73/32 A |
| 5,027,662 A | 7/1991 | Titlow et al. .......... 73/861.356 |
| 5,029,482 A | 7/1991 | Liu et al. ................ 73/861.04 |
| 5,050,439 A | 9/1991 | Thompson ............. 73/861.356 |
| 5,052,231 A | 10/1991 | Christ et al. ........... 73/861.356 |
| 5,054,313 A | 10/1991 | Fitzgerald et al. ......... 73/54.27 |
| 5,054,326 A | 10/1991 | Mattar ................... 73/861.355 |
| 5,218,869 A | 6/1993 | Pummer ...................... 73/629 |
| 5,228,327 A | 7/1993 | Bruck ........................ 73/1.34 |
| 5,259,250 A | 11/1993 | Kolpak ................. 73/861.355 |
| 5,271,281 A | 12/1993 | Mattar et al. .......... 73/861.355 |
| 5,295,084 A | 3/1994 | Arunachalam et al. ....... 702/50 |
| 5,301,557 A | 4/1994 | Cage et al. ............ 73/861.355 |
| 5,321,991 A * | 6/1994 | Kalotay ................. 73/861.357 |
| 5,343,764 A | 9/1994 | Matter et al. .......... 73/861.355 |
| 5,347,874 A | 9/1994 | Kalotay et al. ........ 73/861.357 |
| 5,400,653 A | 3/1995 | Kalotay et al. ........ 73/861.355 |
| 5,429,002 A | 7/1995 | Coleman ............... 73/861.356 |
| 5,469,748 A | 11/1995 | Kalotay ................. 73/861.356 |
| 5,497,665 A | 3/1996 | Cage et al. ............ 73/861.356 |
| 5,497,666 A | 3/1996 | Patten et al. ........... 73/861.355 |
| 5,535,632 A | 7/1996 | Kolpak ................... 73/861.04 |
| 5,555,190 A | 9/1996 | Derby et al. .................. 702/45 |
| 5,570,300 A | 10/1996 | Henry et al. ................. 702/45 |
| 5,578,764 A | 11/1996 | Yokoi et al. ........... 73/861.356 |
| 5,594,180 A | 1/1997 | Carpenter et al. ..... 73/861.356 |
| 5,648,616 A | 7/1997 | Keel ..................... 73/861.356 |
| 5,654,502 A | 8/1997 | Dutton ................... 73/152.18 |
| 5,687,100 A | 11/1997 | Buttler et al. ............... 702/137 |
| 5,732,193 A | 3/1998 | Aberson ...................... 706/45 |
| 5,734,112 A | 3/1998 | Bose et al. ............. 73/861.56 |
| 5,774,378 A | 6/1998 | Yang ......................... 702/104 |
| 5,804,741 A | 9/1998 | Freeman ............... 73/861.356 |
| 5,877,954 A | 3/1999 | Kimasauskas et al. ........ 700/29 |
| 5,926,096 A | 7/1999 | Mattar et al. .............. 340/606 |
| 5,969,264 A | 10/1999 | Rivkin .................. 73/861.356 |
| 6,073,495 A | 6/2000 | Stadler .................. 73/861.356 |
| 6,092,429 A | 7/2000 | Cunningham et al. ... 73/861.35 |
| 6,185,470 B1 | 2/2001 | Pado et al. .................. 700/104 |
| 6,301,973 B1 | 10/2001 | Smith .................... 73/861.357 |
| 6,309,342 B1 | 10/2001 | Blazey et al. ................. 600/26 |
| 6,311,136 B1 | 10/2001 | Henry et al. ................. 702/45 |
| 6,318,156 B1 * | 11/2001 | Dutton et al. ............. 73/61.44 |
| 6,318,186 B1 * | 11/2001 | Smith et al. ........... 73/861.356 |
| 6,327,914 B1 | 12/2001 | Dutton ................. 73/861.356 |
| 6,378,354 B1 | 4/2002 | Sharp ......................... 73/1.16 |
| 6,505,131 B1 | 1/2003 | Henrot ........................ 702/54 |
| 6,505,519 B2 | 1/2003 | Henry et al. ........... 73/861.356 |
| 6,507,791 B2 | 1/2003 | Henry et al. .................. 702/45 |
| 6,551,251 B2 | 4/2003 | Zuckerwar et al. ......... 600/528 |
| 6,564,619 B2 | 5/2003 | Dutton et al. .............. 73/61.44 |
| 2002/0033043 A1 | 3/2002 | Dutton et al. .............. 73/61.44 |
| 2002/0038186 A1 | 3/2002 | Henry et al. .................. 702/45 |
| 2002/0133307 A1 | 9/2002 | Maginnis .................... 702/100 |

OTHER PUBLICATIONS

David Spitzer; "Mass Flowmeters"; *Industries Flow Measurement, Chapter 12*; pp. 197–210; 1990.

E. Luntta et al., "Neural Network Approach to Ultrasonic Flow Measurements", *Flow Measurement and Instrumentation*, vol. 10, pp. 35–43, 1999.

J. Hemp et al.; "On the Theory and Performance of Coriolis Mass Flowmeters"; *Proceedings of the International Conference on Mass Flow Measurement Direct and Indirect*; IBC Technical Services; 40 pages; Feb. 1989.

R. Reimann, "Developments in Tow–Phase Mass Flow Rate Instrumentation", pp. 339–402.

J.T. Grumski et al., "Performance of a Coriolis–type Mass Flow Meter in the Measurement of Two–phase (air–liquid) Mixtures", ASME Fluid Engineering Division Publication FED, vol. 17, pp. 75–84, 1984.

Joseph DeCarlo; "True Mass–Flow Measurement", *Fundamentals of Flow Measurement, Unit 11–2*; pp. 208–220; 1984.

M. Henry et al., "The Implications of Digital Communications on Sensor Validation", Report No. QUEL 1912/92, University of Oxford, Department of Engineering Science, Apr. 1992.

M.P. Henry et al., "A New Approach to Sensor Validation", Improving Analyser Performance, IMC, Mar. 17, 1992.

M.P. Henry et al., "A self–Validating Digital Coriolis Mass–flow Meter" (1); overview, 1999.

M.P. Henry et al., "A standard Interface for Self–Validating Sensors", Report No. QUEL 1884/91, University of Oxford, Department of Engineering Science, Sep. 1991.

M.P. Henry et al., "Signal processing, Data Handling and Communications: The Case for Measurement Validation", Mar. 1992.

M.P. Henry, "Intelligent Behaviour For Self–Validating Sensors", Advances in Measurement, pp 1–7, date unknown.

M.P. Henry, "Self–Validation Improves Coriolis Meter", *Control Engineering*, 42 (6), pp. 81–86 (1995).

M.P. Henry, "Sensor Validation and Fieldbus", *IEE Computing and Control Engineering Journal*, 6(6), pp. 263–269.

R.P. Liu et al., "A Neural Network to Correct Mass Flow Errors Caused by Two Phase Flow in a Digital Coriolis Mass Flow Meter", Engineering Science Department, Oxford University.

Kutin, Jože, et al., "Phase–Locking Control of the Coriolis Meter's Resonance Frequency Based on Virtual Instrumentation," *Sensors and Actuators* A 104 (2003), pp. 86–93.

Merriam–Webster's Collegiate Dictionary, Tenth Edition, 1998, p. 747.

Wood, et al., "A Phase–Locked Loop for Driving Vibrating Tube Densimeters," Rev. Sci. Instrum., vol. 60, No. 3, Mar. 1989, pp. 493–494.

* cited by examiner

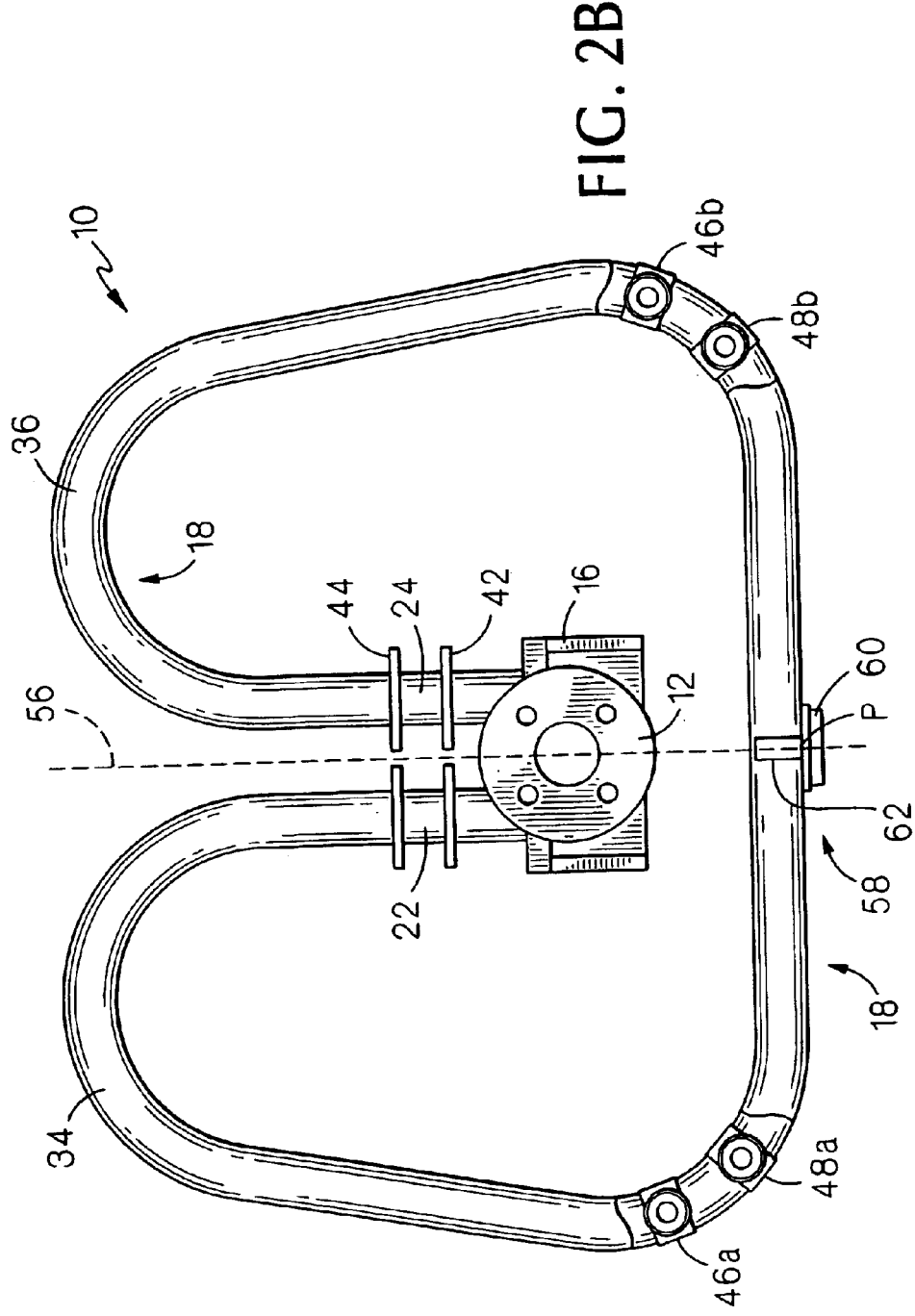

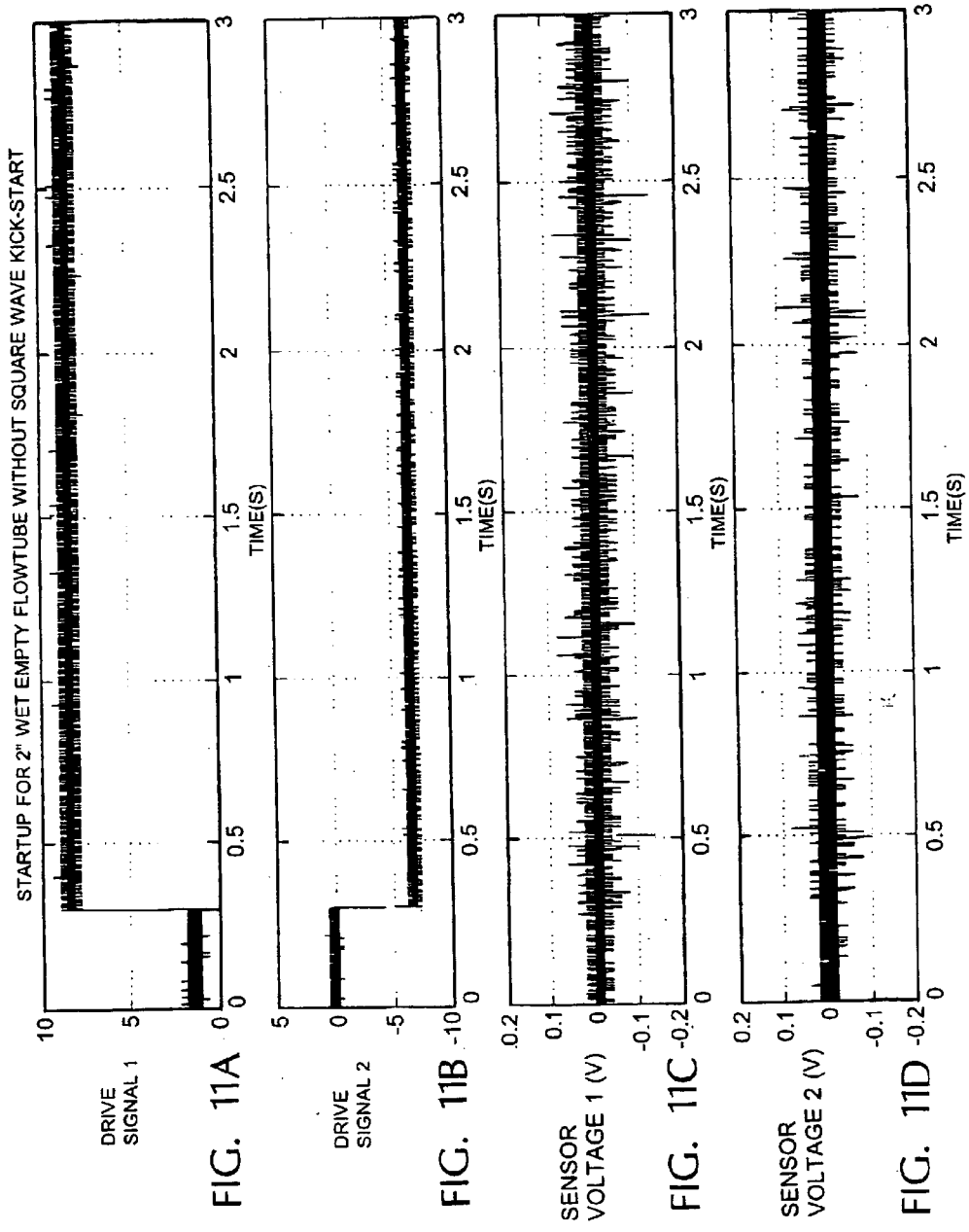

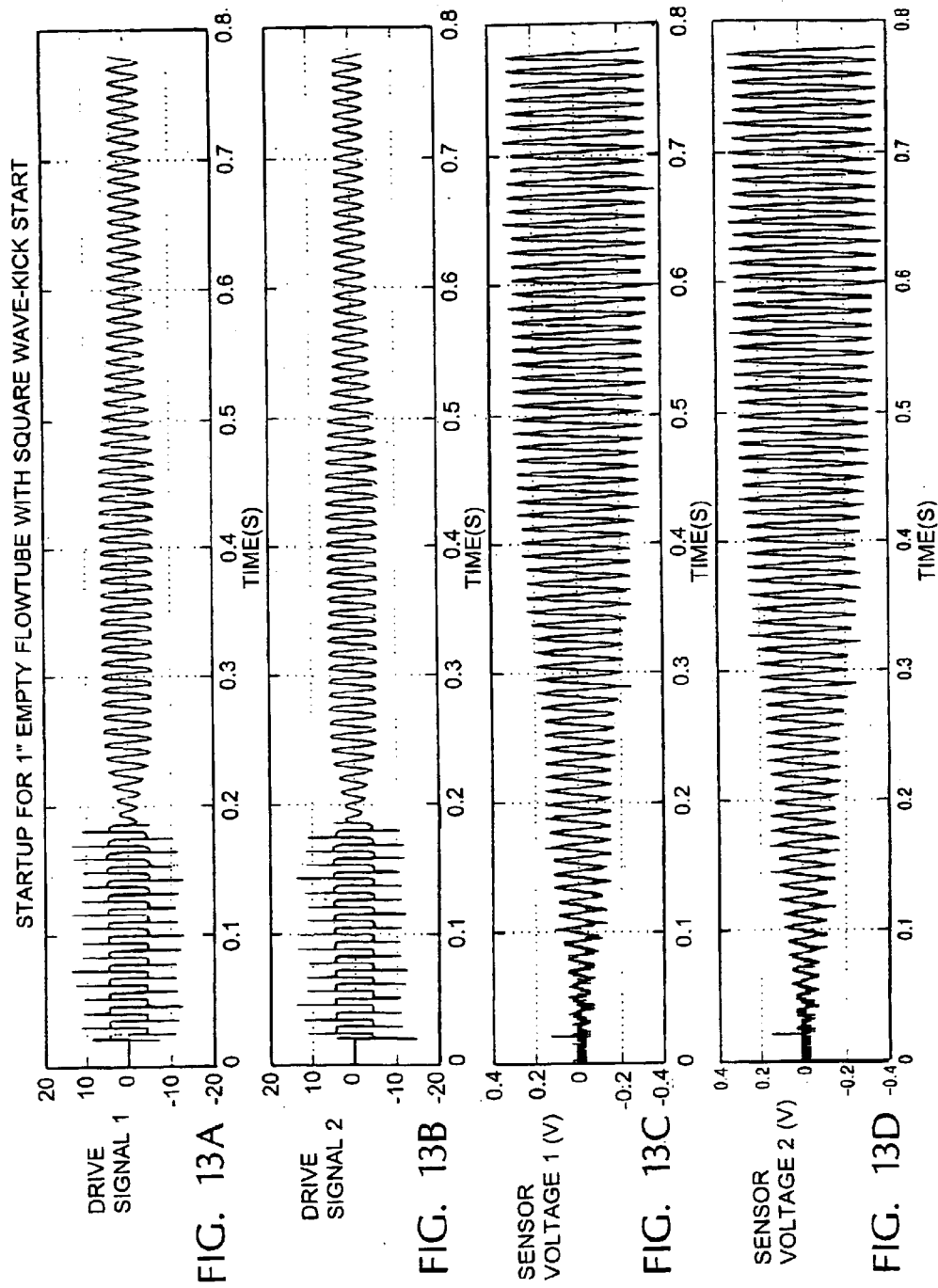

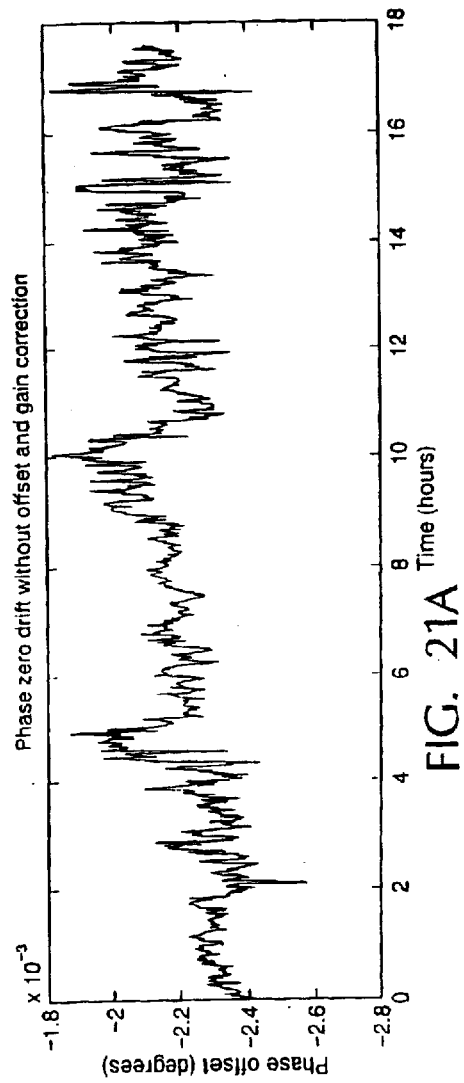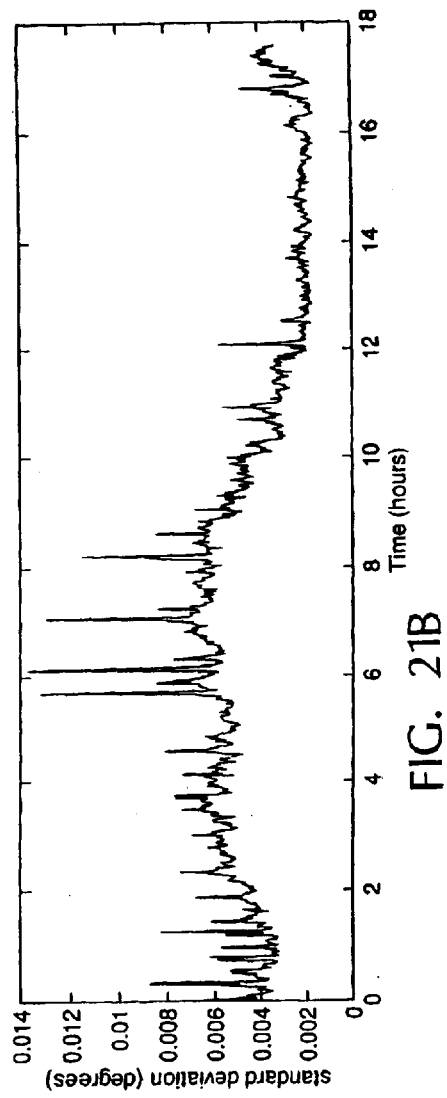

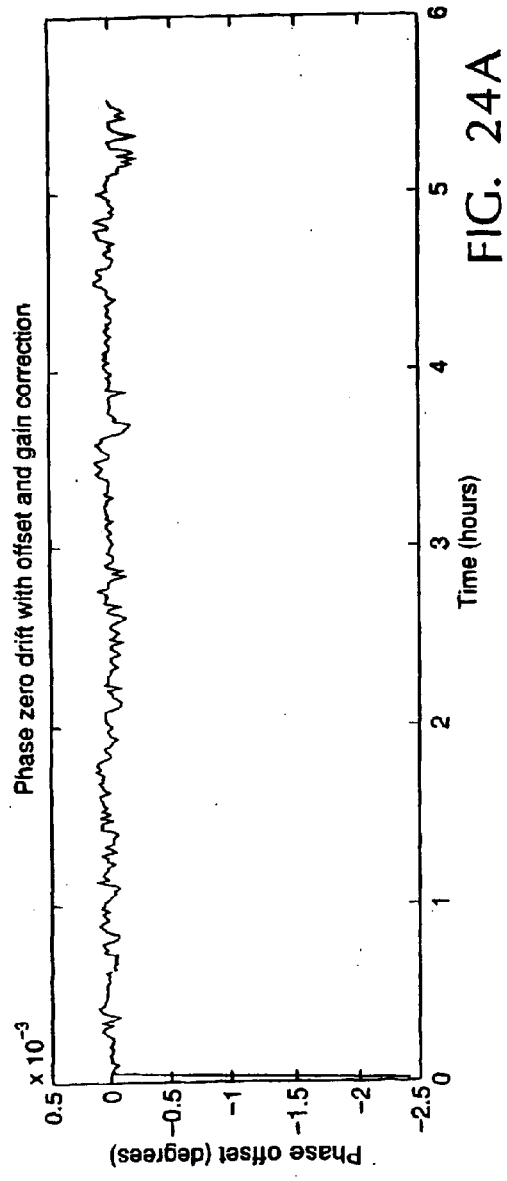
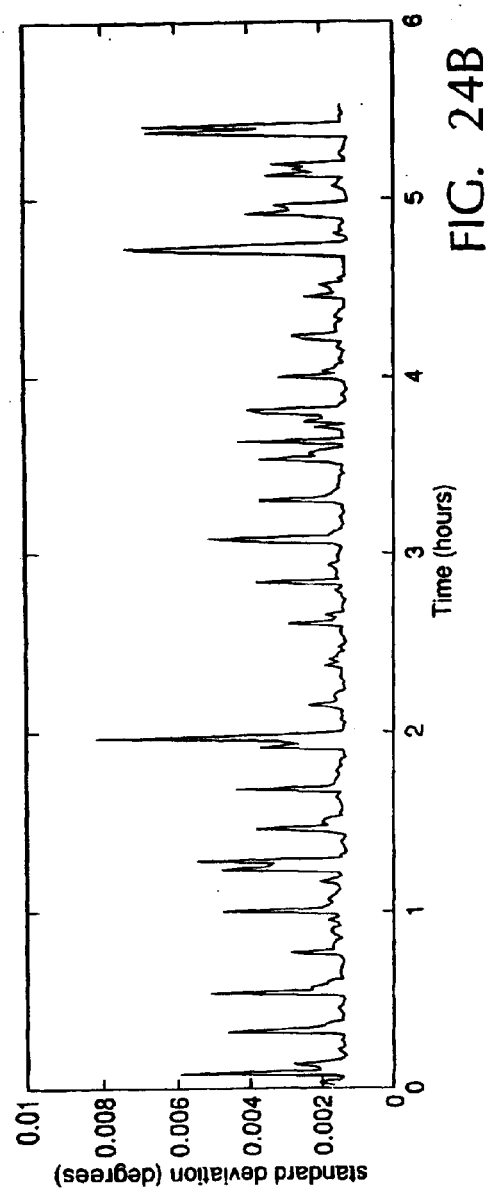

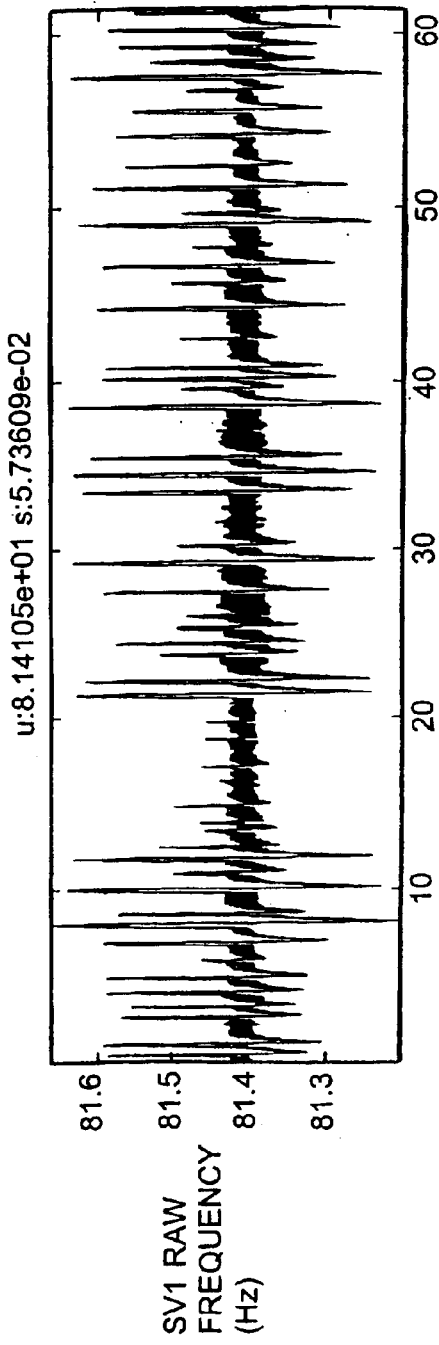
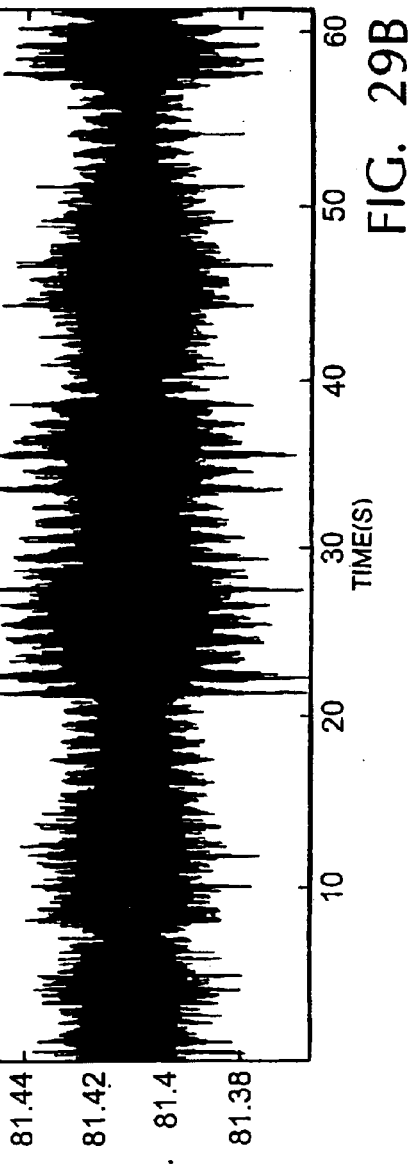
FIG. 29A
FIG. 29B

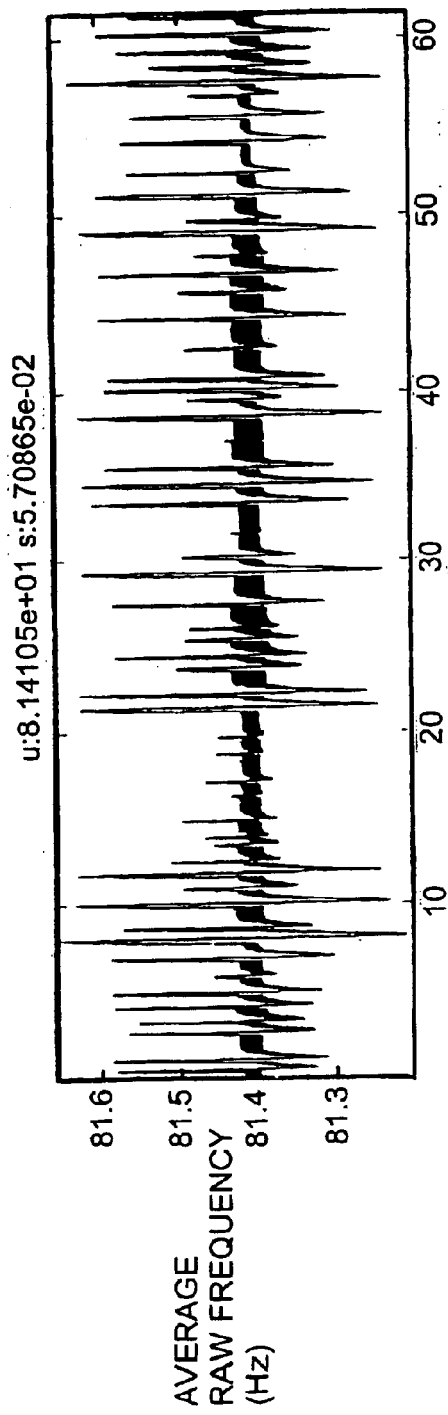
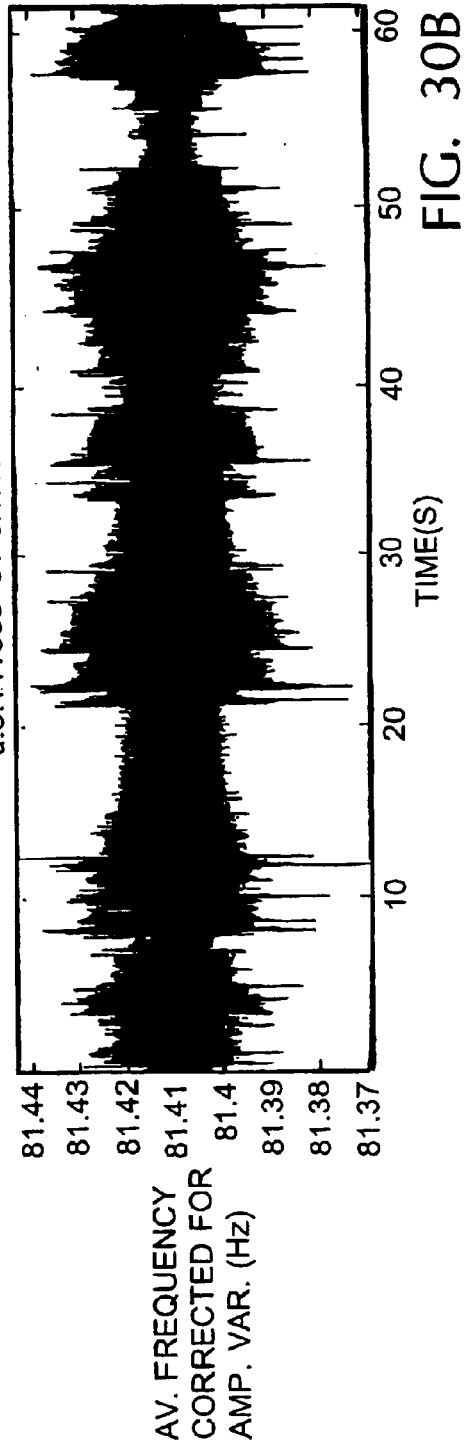
FIG. 30A
FIG. 30B

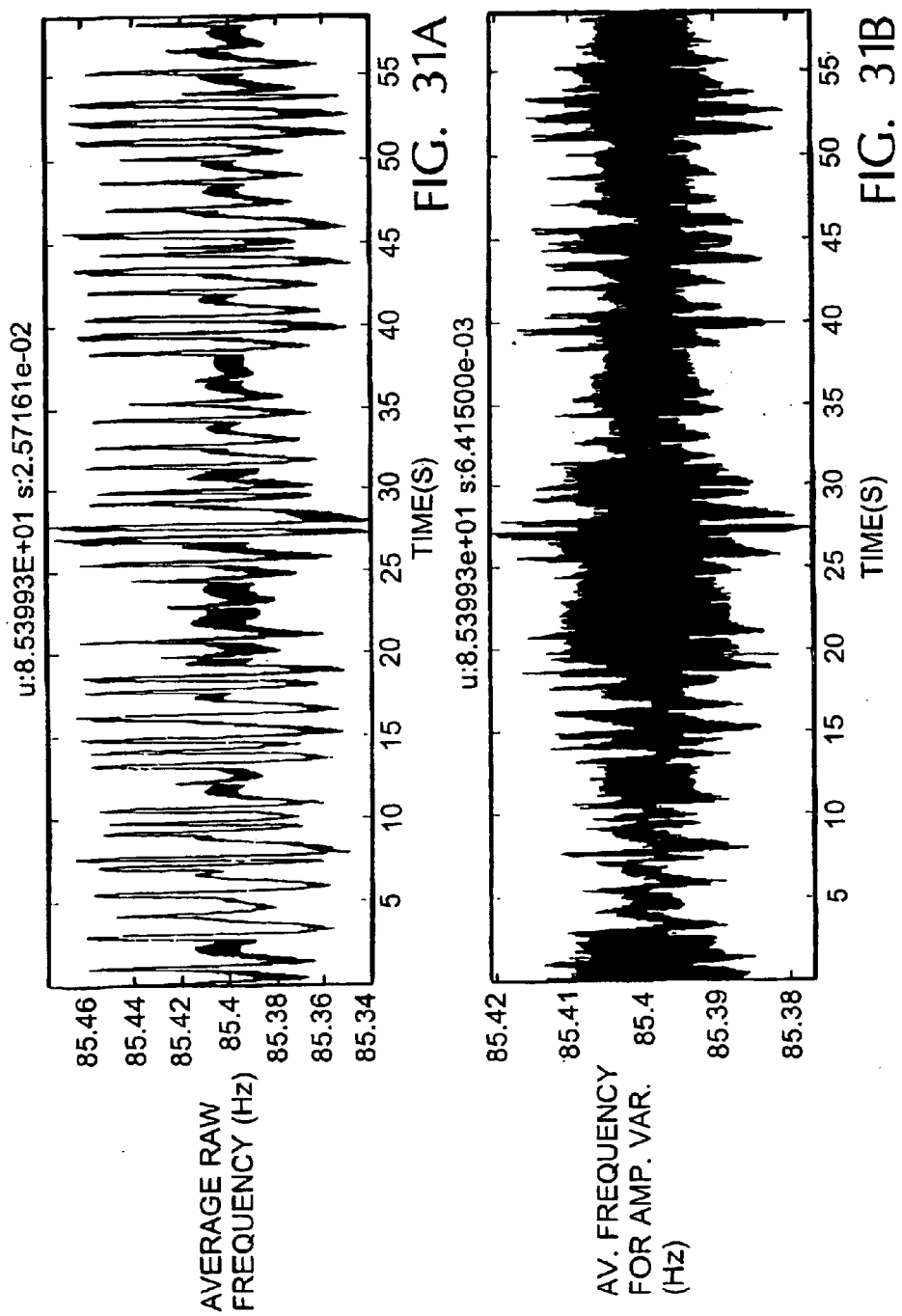

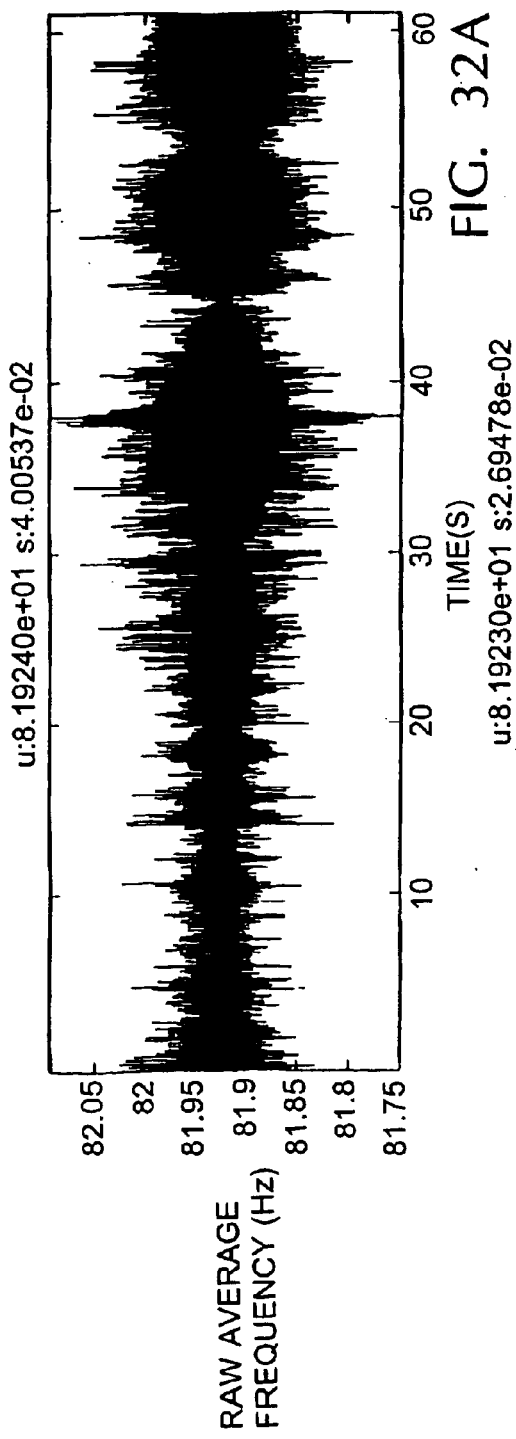
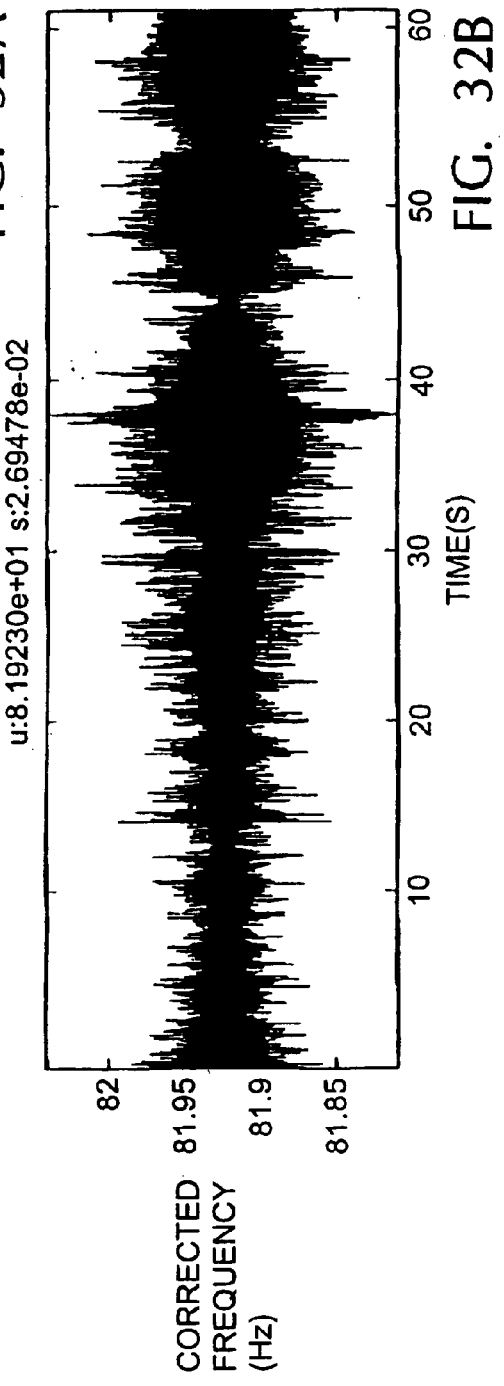
FIG. 32A
FIG. 32B

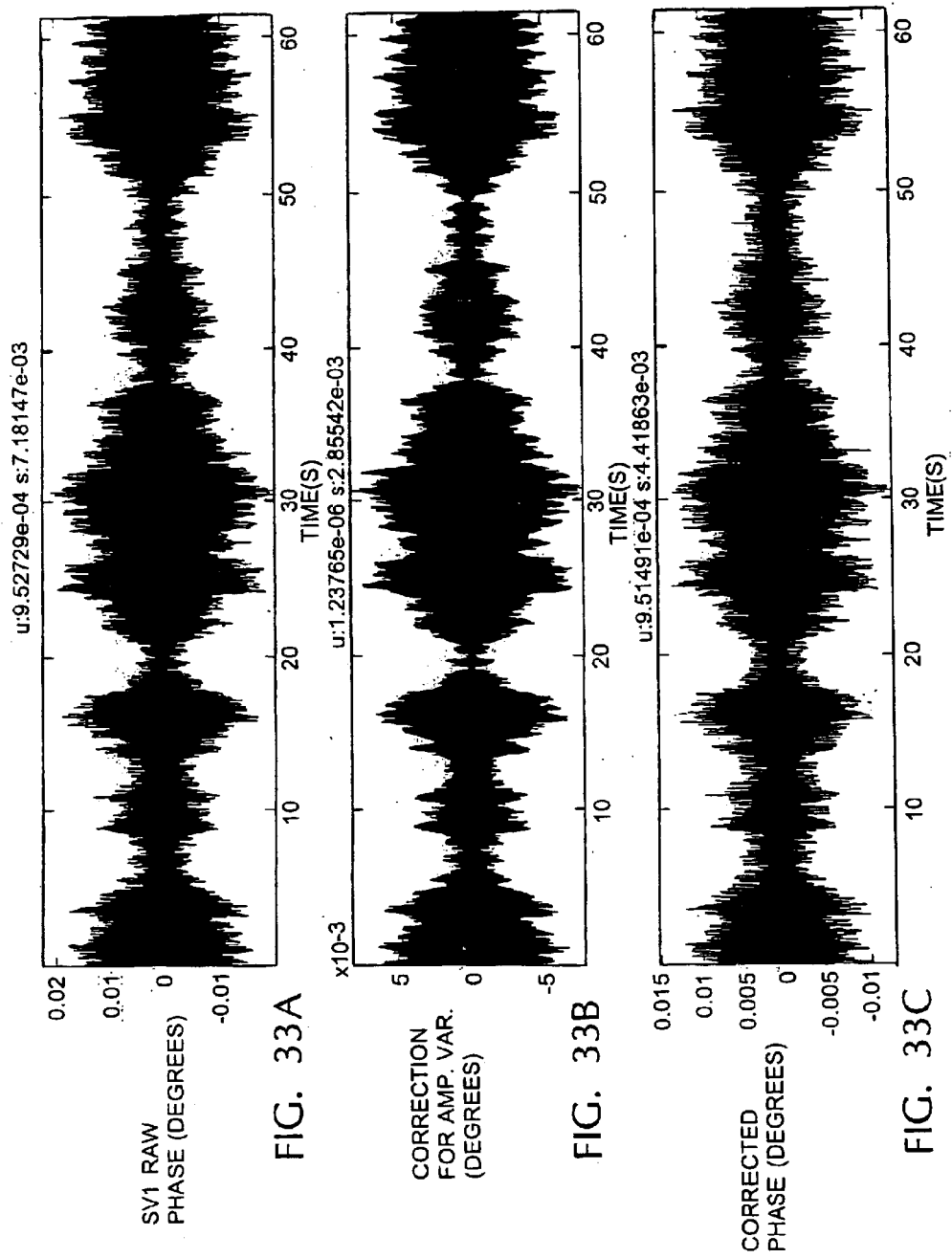

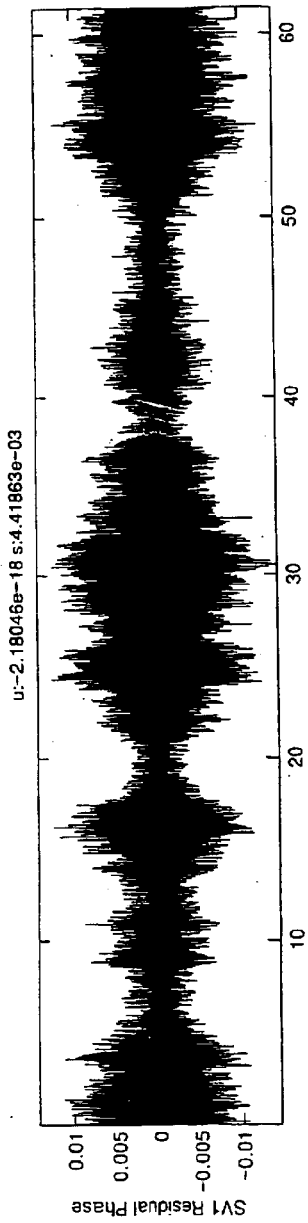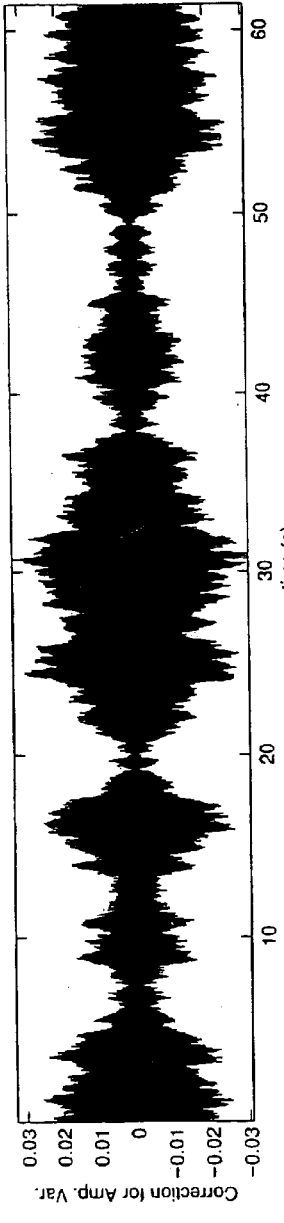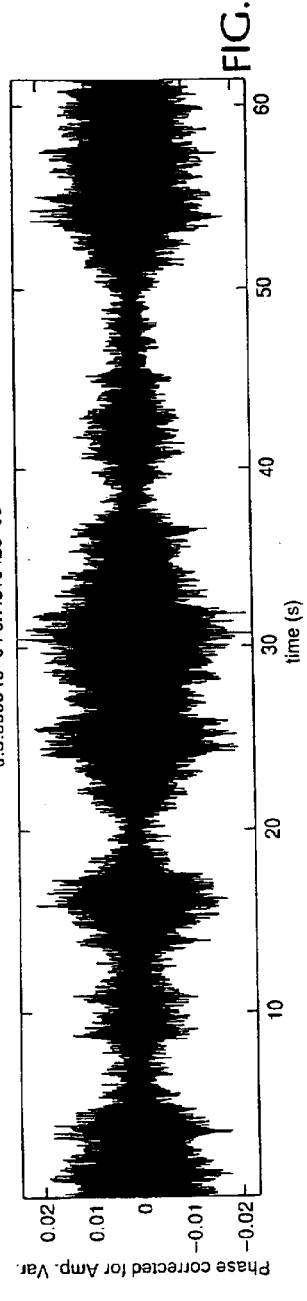

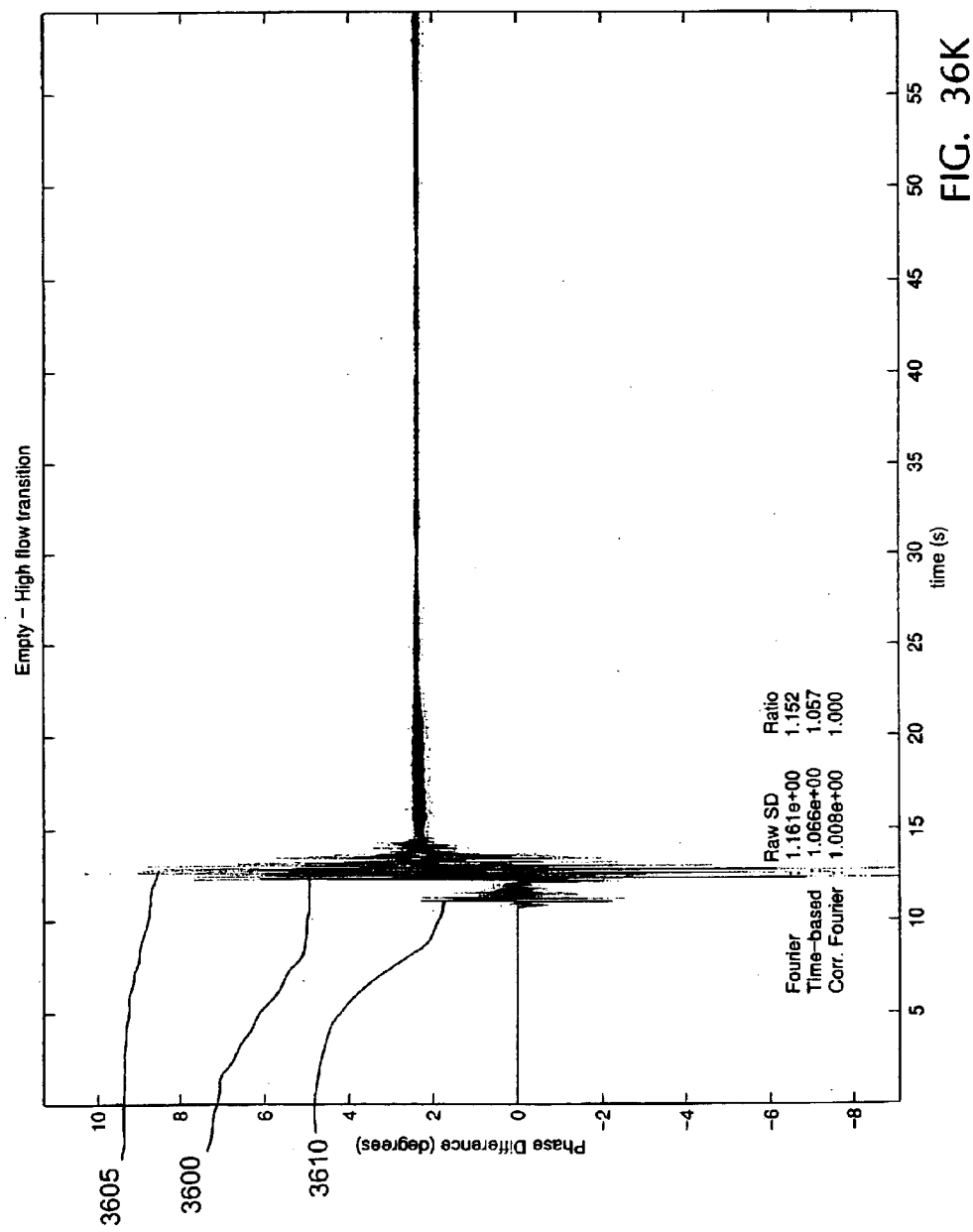

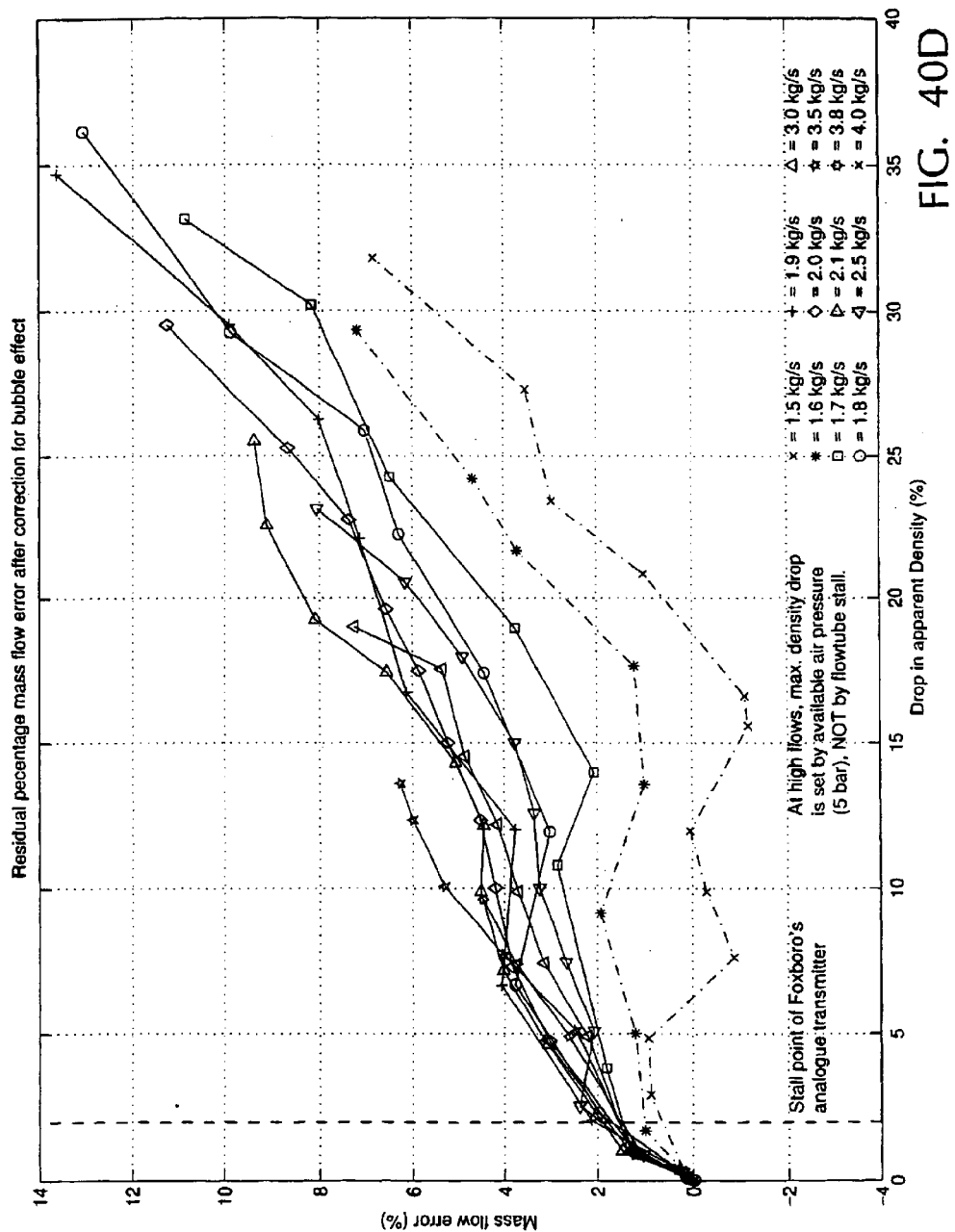

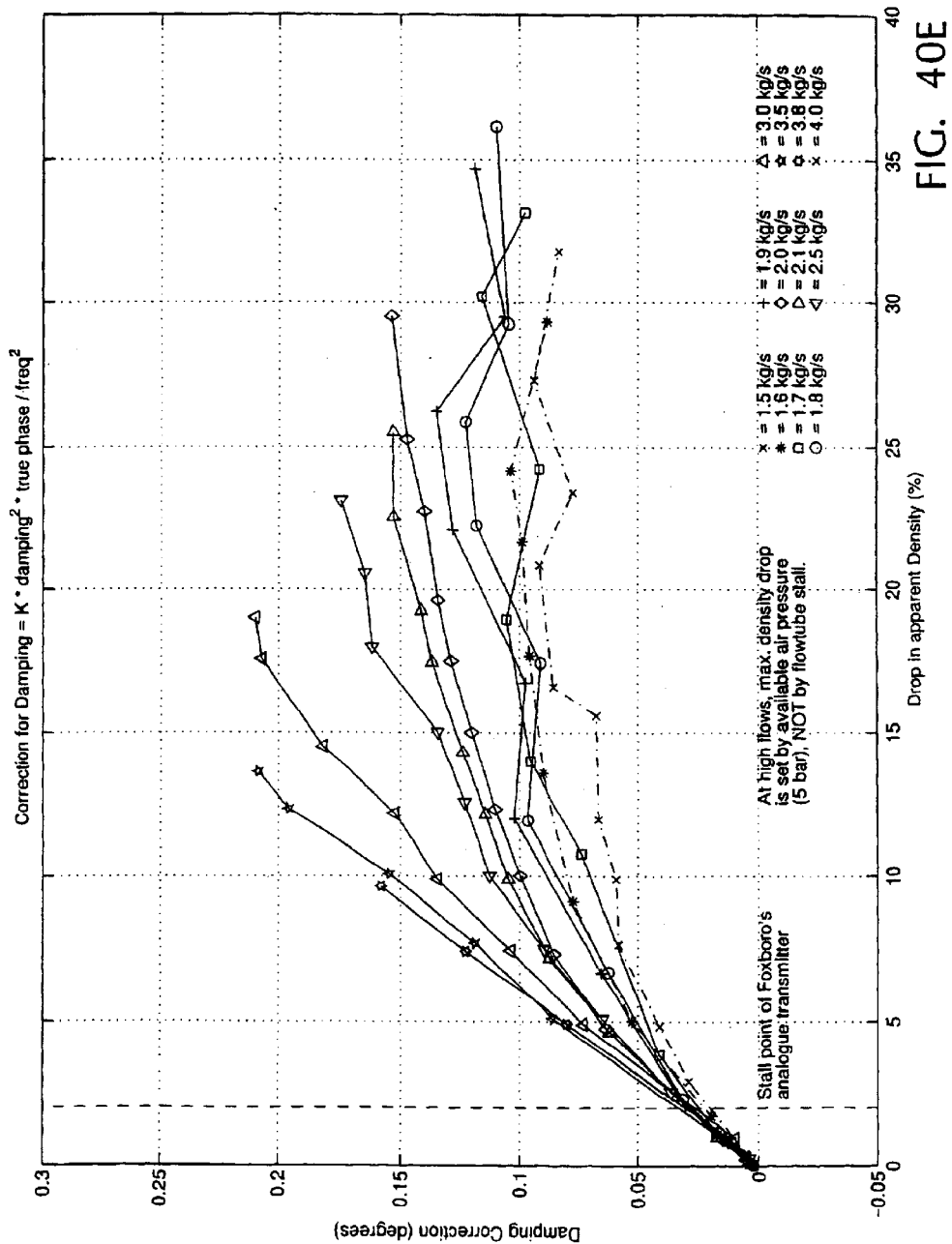

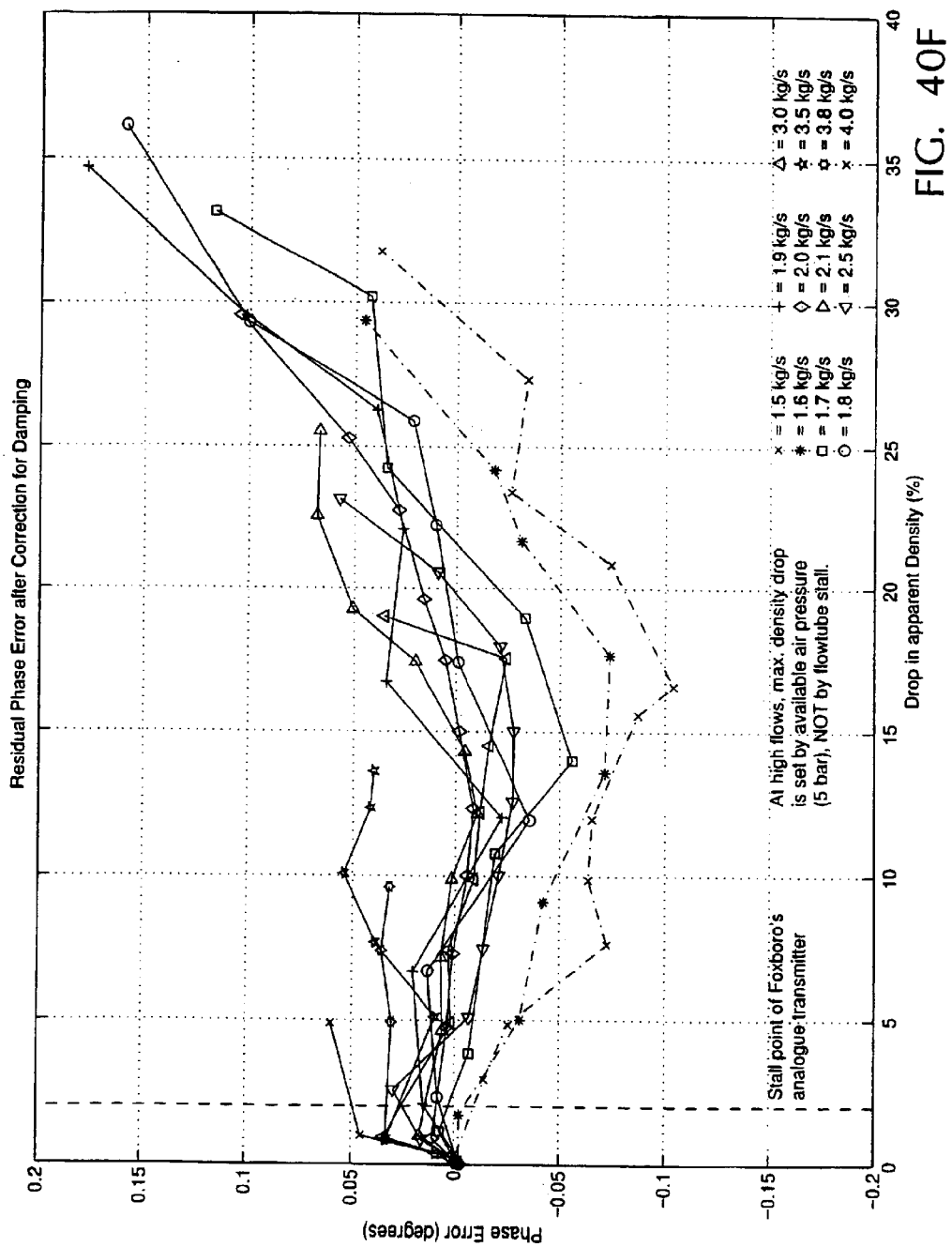

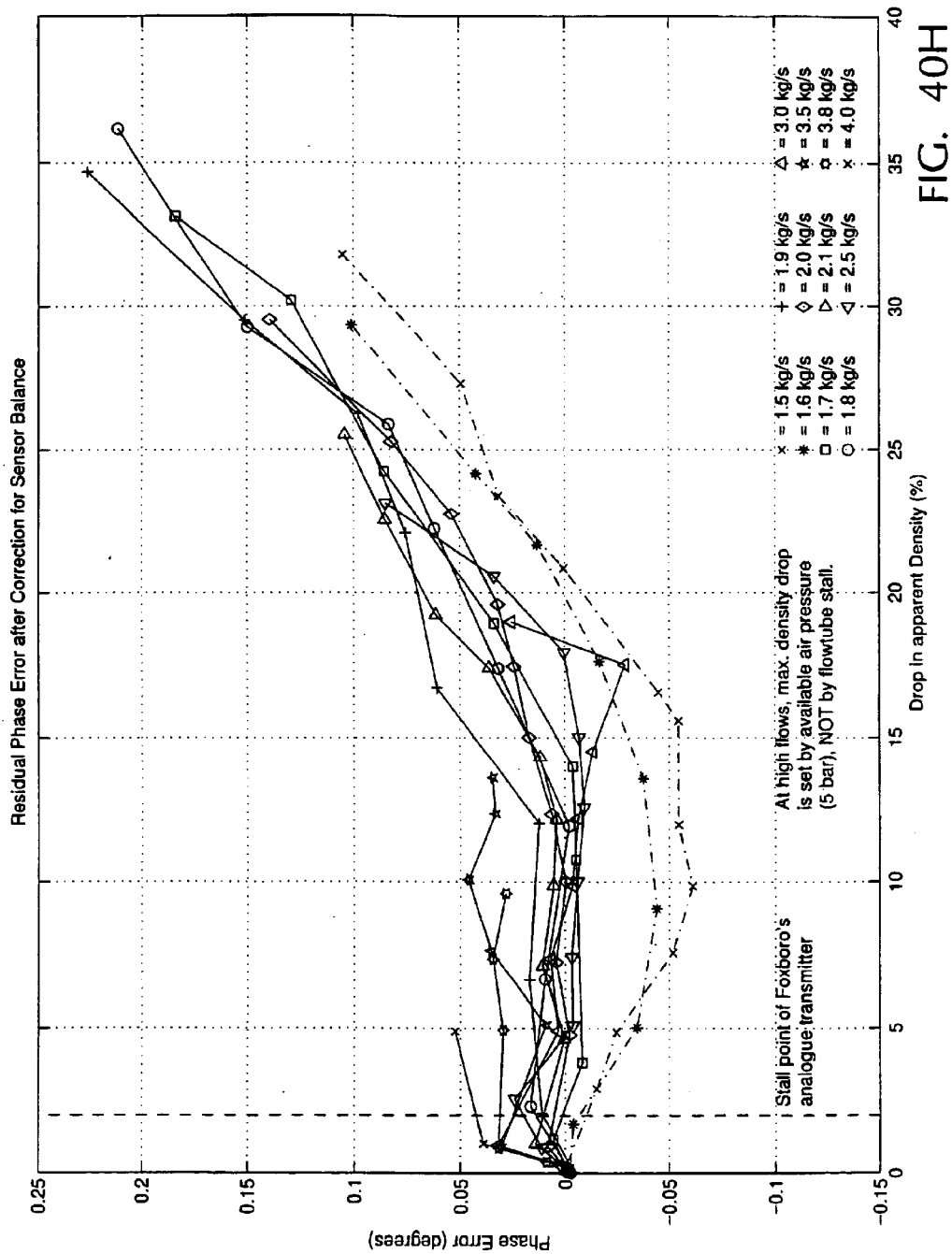

DIGITAL FLOWMETER

CROSS REFERENCE TO RELATED APPLICATIONS

This application is a continuation of U.S. application Ser. No. 09/931,057, filed Aug. 17, 2001, now U.S. Pat. No. 6,754,594 titled DIGITAL FLOWMETER, which is a continuation of U.S. application Ser. No. 09/111,739, filed Jul. 8, 1998, now U.S. Pat. No. 6,311,136, titled DIGITAL FLOWMETER, which claims priority from U.S. Provisional Application No. 60/066,554, filed Nov. 26, 1997, titled DIGITAL FLOWMETER, all of which are incorporated by reference.

TECHNICAL FIELD

The invention relates to flowmeters.

BACKGROUND

Flowmeters provide information about materials being transferred through a conduit. For example, mass flowmeters provide a direct indication of the mass of material being transferred through a conduit. Similarly, density flowmeters, or densitometers, provide an indication of the density of material flowing through a conduit. Mass flowmeters also may provide an indication of the density of the material.

Coriolis-type mass flowmeters are based on the well-known Coriolis effect, in which material flowing through a rotating conduit becomes a radially traveling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

Energy is supplied to the conduit by a driving mechanism that applies a periodic force to oscillate the conduit. One type of driving mechanism is an electromechanical driver that imparts a force proportional to an applied voltage. In an oscillating flowmeter, the applied voltage is periodic, and is generally sinusoidal. The period of the input voltage is chosen so that the motion of the conduit matches a resonant mode of vibration of the conduit. This reduces the energy needed to sustain oscillation. An oscillating flowmeter may use a feedback loop in which a sensor signal that carries instantaneous frequency and phase information related to oscillation of the conduit is amplified and fed back to the conduit using the electromechanical driver.

SUMMARY

The invention provides a digital flowmeter, such as a digital mass flowmeter, that uses a control and measurement system to control oscillation of the conduit and to generate mass flow and density measurements. Sensors connected to the conduit supply signals to the control and measurement system. The control and measurement system processes the signals to produce a measurement of mass flow and uses digital signal processing to generate a signal for driving the conduit. The drive signal then is converted to a force that induces oscillation of the conduit.

The digital mass flowmeter provides a number of advantages over traditional, analog approaches. From a control perspective, use of digital processing techniques permits the application of precise, sophisticated control algorithms that, relative to traditional analog approaches, provide greater responsiveness, accuracy and adaptability.

The digital control system also permits the use of negative gain in controlling oscillation of the conduit. Thus, drive signals that are 180° out of phase with conduit oscillation may be used to reduce the amplitude of oscillation. The practical implications of this are important, particularly in high and variable damping situations where a sudden drop in damping can cause an undesirable increase in the amplitude of oscillation. One example of a variable damping situation is when aeration occurs in the material flowing through the conduit.

The ability to provide negative feedback also is important when the amplitude of oscillation is controlled to a fixed setpoint that can be changed under user control. With negative feedback, reductions in the oscillation setpoint can be implemented as quickly as increases in the setpoint. By contrast, an analog meter that relies solely on positive feedback must set the gain to zero and wait for system damping to reduce the amplitude to the reduced setpoint.

From a measurement perspective, the digital mass flowmeter can provide high information bandwidth. For example, a digital measurement system may use analog-to-digital converters operating at eighteen bits of precision and sampling rates of 55 kHz. The digital measurement system also may use sophisticated algorithms to filter and process the data, and may do so starting with the raw data from the sensors and continuing to the final measurement data. This permits extremely high precision, such as, for example, phase precision to five nanoseconds per cycle. Digital processing starting with the raw sensor data also allows for extensions to existing measurement techniques to improve performance in non-ideal situations, such as by detecting and compensating for time-varying amplitude, frequency, and zero offset.

The control and measurement improvements interact to provide further improvements. For example, control of oscillation amplitude is dependent upon the quality of amplitude measurement. Under normal conditions, the digital mass flowmeter may maintain oscillation to within twenty parts per million of the desired setpoint. Similarly, improved control has a positive benefit on measurement. Increasing the stability of oscillation will improve measurement quality even for meters that do not require a fixed amplitude of oscillation (i.e., a fixed setpoint). For example, with improved stability, assumptions used for the measurement calculations are likely to be valid over a wider range of conditions.

The digital mass flowmeter also permits the integration of entirely new functionality (e.g., diagnostics) with the measurement and control processes. For example, algorithms for detecting the presence of process aeration can be implemented with compensatory action occurring for both measurement and control if aeration is detected.

Other advantages of the digital mass flowmeter result from the limited amount of hardware employed, which makes the meter simple to construct, debug, and repair in production and in the field. Quick repairs in the field for improved performance and to compensate for wear of the mechanical components (e.g., loops, flanges, sensors and drivers) are possible because the meter uses standardized hardware components that may be replaced with little difficulty, and because software modifications may be made with relative ease. In addition, integration of diagnostics, measurement, and control is simplified by the simplicity of the hardware and the level of functionality implemented in software. New functionality, such as low power components or components with improved performance, can be integrated without a major redesign of the overall control system.

In one general aspect, a digital flowmeter includes a vibratable conduit, a driver connected to the conduit and operable to impart motion to the conduit, and a sensor connected to the conduit and operable to sense the motion of the conduit. A control and measurement system connected to the driver and the sensor includes circuitry that receives a sensor signal from the sensor, generates a drive signal based on the sensor signal using digital signal processing, supplies the drive signal to the driver, and generates a measurement of a property of material flowing through the conduit based on the signal from the sensor.

Embodiments may include one or more of the following features. The meter may include a second sensor connected to the conduit and operable to sense the motion of the conduit. In this case, the control and measurement system is connected to the second sensor and receives a second sensor signal from the second sensor, generates the drive signal based on the first and second sensor signals, and generates the measurement of the property of material flowing through the conduit based on the first and second sensor signals. The control and measurement system may digitally combine the first and second sensor signals and generate the drive signal based on the combination of the sensor signals.

The control and measurement system may generate different drive signals for the two drivers. The drive signals may have, for example, different frequencies or amplitudes.

The digital flowmeter also may include circuitry for measuring current supplied to the driver. The circuitry may include a resistor in series with the driver and an analog-to-digital converter in parallel with the resistor and configured to measure a voltage across the resistor, to convert the measured voltage to a digital value, and to supply the digital value to the control and measurement system.

The digital flowmeter also may include a first pressure sensor connected to measure a first pressure at an inlet to the conduit and a second pressure sensor connected to measure a second pressure at an outlet of the conduit. Analog-to-digital converters may be connected and configured to convert signals produced by the first pressure sensor and the second pressure sensor to digital values and to supply the digital values to the control and measurement system. Temperature sensors may be connected to measure temperatures at the inlet and outlet of the conduit.

The control and measurement system may generate the measurement of the property by estimating a frequency of the first sensor signal, calculating a phase difference using the first sensor signal, and generating the measurement using the calculated phase difference. The control and measurement system may compensate for amplitude differences in the sensor signals by adjusting the amplitude of one of the sensor signals. For example, the control and measurement system may multiply the amplitude of one of the sensor signals by a ratio of the amplitudes of the sensor signals.

When the sensor signal is generally periodic, the control and measurement system may process the sensor signal in sets. Each set may include data for a complete cycle of the periodic sensor signal, and consecutive sets may include data for overlapping cycles of the periodic sensor signal. The control and measurement system may estimate an end point of a cycle using a frequency of a previous cycle.

The control and measurement system may analyze data for a cycle to determine whether the cycle merits further processing. For example, the system may determine that a cycle does not merit further processing when data for the cycle does not conform to expected behavior for the data, where the expected behavior may be based on one or more parameters of a previous cycle. In one implementation, the system determines that a cycle does not merit further processing when a frequency for the cycle differs from a frequency for the previous cycle by more than a threshold amount. The system may determine whether the frequencies differ by comparing values at certain points in the cycle to values that would occur if the frequency for the cycle equaled the frequency for the previous cycle.

The control and measurement system may determine a frequency of the sensor signal by detecting zero-crossings of the sensor signal and counting samples between zero crossings. The system also may determine a frequency of the sensor signal using an iterative curve fitting technique.

The control and measurement system may determine an amplitude of the sensor signal using Fourier analysis, and may use the determined amplitude in generating the drive signal.

The control and measurement system may determine a phase offset for each sensor signal and may determine the phase difference by comparing the phase offsets. The system also may determine the phase difference using Fourier analysis. The control and measurement system may determine a frequency, amplitude and phase offset for each sensor signal, and may scale the phase offsets to an average of the frequencies of the sensor signals.

The control and measurement system may calculate the phase difference using multiple approaches and may select a result of one of the approaches as the calculated phase difference.

The control and measurement system may combine the sensor signals to produce a combined signal and may generate the drive signal based on the combined signal. For example, the control and measurement system may sum the sensor signals to produce the combined signal and may generate the drive signal by applying a gain to the combined signal.

In general, the control and measurement system may initiate motion of the conduit by using a first mode of signal generation to generate the drive signal, and may sustain motion of the conduit using a second mode of signal generation to generate the drive signal. The first mode of signal generation may be synthesis of a periodic signal having a desired property, such as a desired initial frequency of conduit vibration, and the second mode of signal generation may use a feedback loop including the sensor signal.

In other instances, the first mode of signal generation may include use of a feedback loop including the sensor signal and the second mode of signal generation may include synthesis of a periodic signal having a desired property. For example, the control and measurement system may generate the drive signal by applying a large gain to the combined signal to initiate motion of the conduit and generating a periodic signal having a phase and frequency based on a phase and frequency of a sensor signal as the drive signal after motion has been initiated. The desired property of the synthesized signal may be a frequency and a phase corresponding to a frequency and a phase of the sensor signal.

The control and measurement system generates an adaptable, periodic drive signal. For example, the meter may include positive and negative direct current sources connected between the control and measurement system and the driver, and the control and measurement system may generate the drive signal by switching the current sources on and off at intervals having a phase and frequency based on the sensor signal. The control and measurement system may generate the drive signal by synthesizing a sine wave having a property corresponding to a property of the sensor signal, such as a phase and a frequency corresponding to a phase and a frequency of the sensor signal.

The control and measurement system may digitally generate a gain for use in generating the drive signal based on one or more properties of the sensor signal. For example, the control and measurement system may digitally generate the gain based on an amplitude of the sensor signal.

The driver may be operable to impart an oscillating motion to the conduit. The control and measurement system also may digitally implement a PI control algorithm to regulate the amplitude of conduit oscillation. The control and measurement system also may digitally generate the drive signal based on the sensor signal so as to maintain an amplitude of oscillation of the conduit at a user-controlled value. In support of this, the control and measurement system may generate a negative drive signal that causes the driver to resist motion of the conduit when the amplitude of oscillation exceeds the user-controlled value and a positive drive signal that causes the driver to impart motion to the conduit when the amplitude of oscillation is less than the user-controlled value.

The control and measurement system may include a controller that generates a gain signal based on the sensor signal and a multiplying digital-to-analog converter connected to the controller to receive the gain signal and generate the drive signal based on the gain signal.

When the digital flowmeter includes a second sensor connected to the conduit and operable to sense the motion of the conduit, the control and measurement system may include a controller that generates the measurement, a first analog-to-digital converter connected between the first sensor and the controller to provide a first digital sensor signal to the controller, and a second analog-to-digital converter connected between the second sensor and the controller to provide a second digital sensor signal to the controller. The controller may combine the digital sensor signals to produce a combined signal and to generate a gain signal based on the first and second digital sensor signals. The control and measurement system also may include a multiplying digital-to-analog converter connected to receive the combined signal and the gain signal from the controller to generate the drive signal as a product of the combined signal and the gain signal.

The control and measurement system may selectively apply a negative gain to the sensor signal to reduce motion of the conduit.

The control and measurement system also may compensate for zero offset in the sensor signal. The zero offset may include a component attributable to gain variation and a component attributable to gain nonlinearity, and the control and measurement system may separately compensate for the two components. The control and measurement system may compensate for zero offset by generating one or more correction factors and modifying the sensor signal using the correction factors.

The control and measurement system may calculate phase offsets for the first and second sensor signals. The phase offset may be defined as a difference between a zero-crossing point of a sensor signal and a point of zero phase for a component of the sensor signal corresponding to a fundamental frequency of the sensor signal. The control and measurement system may combine the calculated phase offsets to produce a phase difference.

The control and measurement system may generate the measurement of the property by estimating a frequency of the first sensor signal, estimating a frequency of the second sensor signal, with the frequency of the second sensor signal being different from the frequency of the first sensor signal, and calculating a phase difference between the sensor signals using the estimated frequencies.

When the sensor is a velocity sensor, the control and measurement system may estimate a frequency, amplitude, and phase of the sensor signal, and may correct the estimated frequency, amplitude, and phase to account for performance differences between a velocity sensor and an absolute position sensor. Instead of controlling the apparent amplitude of oscillation (i.e., the velocity of oscillation when the sensor is a velocity sensor), the system may control the true amplitude by dividing the sensor signal by the estimated frequency. This correction should provide improved amplitude control and noise reduction.

The control and measurement system may estimate a first parameter of the sensor signal, determine a rate of change of a second parameter, and correct the estimated first parameter based on the determined rate of change. For example, the system may correct an estimated frequency, amplitude, or phase of the sensor signal based on a determined rate of change of the frequency or amplitude of oscillation of the conduit. The system may perform separate corrections for each sensor signal.

The digital flowmeter may be a mass flowmeter and the property of material flowing through the conduit may be a mass flow rate. The digital flowmeter also may be a densitometer and the property of material flowing through the conduit may be a density of the material.

The control and measurement system may account for effects of aeration in the conduit by determining an initial mass flow rate, determining an apparent density of material flowing through the conduit, comparing the apparent density to a known density of the material to determine a density difference, and adjusting the initial mass flow rate based on the density difference to produce an adjusted mass flow rate. The system may further account for effects of aeration in the conduit by adjusting the adjusted mass flow rate to account for effects of damping. To further account for effects of aeration in the conduit, the system may adjust the adjusted mass flow rate based on differences between amplitudes of the first and second sensor signals.

The vibratable conduit may include two parallel planar loops. The sensor and driver may be connected between the loops.

The meter may include a power circuit that receives power on only a single pair of wires. The power circuit provides power to the digital control and measurement system and to the driver, and the digital control and measurement system is operable to transmit the measurement of the property of material flowing through the conduit on the single pair of wires. The power circuit may include a constant output circuit that provides power to the digital control and measurement system and drive capacitor that is charged by excess power from the two wires. The digital control and measurement system may discharge the drive capacitor to power the driver, and may monitor a charge level of the drive capacitor and discharge the drive capacitor after a charge level of the capacitor reaches a threshold level. The digital control and measurement system also may discharge the drive capacitor periodically and to perform bidirectional communications on the pair of wires.

The control and measurement system may collect a first data set for a period of the periodic signal and process the first data set to generate the drive signal and the measurement. The system may collect a second data set for a subsequent period of the sensor signal simultaneously with processing the first data set. The period corresponding to the first data set may overlap the period corresponding to the second data set.

The control and measurement system may control the drive signal to maintain an amplitude of the sensor signal at a fixed setpoint, reduce the fixed setpoint when the drive signal exceeds a first threshold level, and increase the fixed setpoint when the drive signal is less than a second threshold level and the fixed setpoint is less than a maximum permitted value for the setpoint. The first threshold level may be 95% or less of a maximum permitted drive signal.

The control and measurement system may perform an uncertainty analysis on the measurement. In this case, the control and measurement system may transmit the measurement and results of the uncertainty analysis to the control system.

The control and measurement system may use digital processing to adjust a phase of the drive signal to compensate for a time delay associated with the sensor and components connected between the sensor and the driver.

The details of one or more implementations are set forth in the accompanying drawings and the description below. Other features and advantages will be apparent from the description and drawings, and from the claims.

DESCRIPTION OF DRAWINGS

FIGS. 2A and 2B are perspective and side views of mechanical components of a mass flowmeter.

FIGS. 11A–11D, 12A–12D, and 13A–13D illustrate drive and sensor voltages at system startup.

FIGS. 21A and 21B are graphs of phase measurements.

FIGS. 23A–23C, 24A, and 24B are graphs of phase measurements.

FIGS. 27A–35E are graphs illustrating application of the procedure of FIG. 29.

FIGS. 36A–36L are graphs illustrating phase measurement.

FIGS. 40A–40H are graphs illustrating correction for aeration.

DETAILED DESCRIPTION

Figure 1:
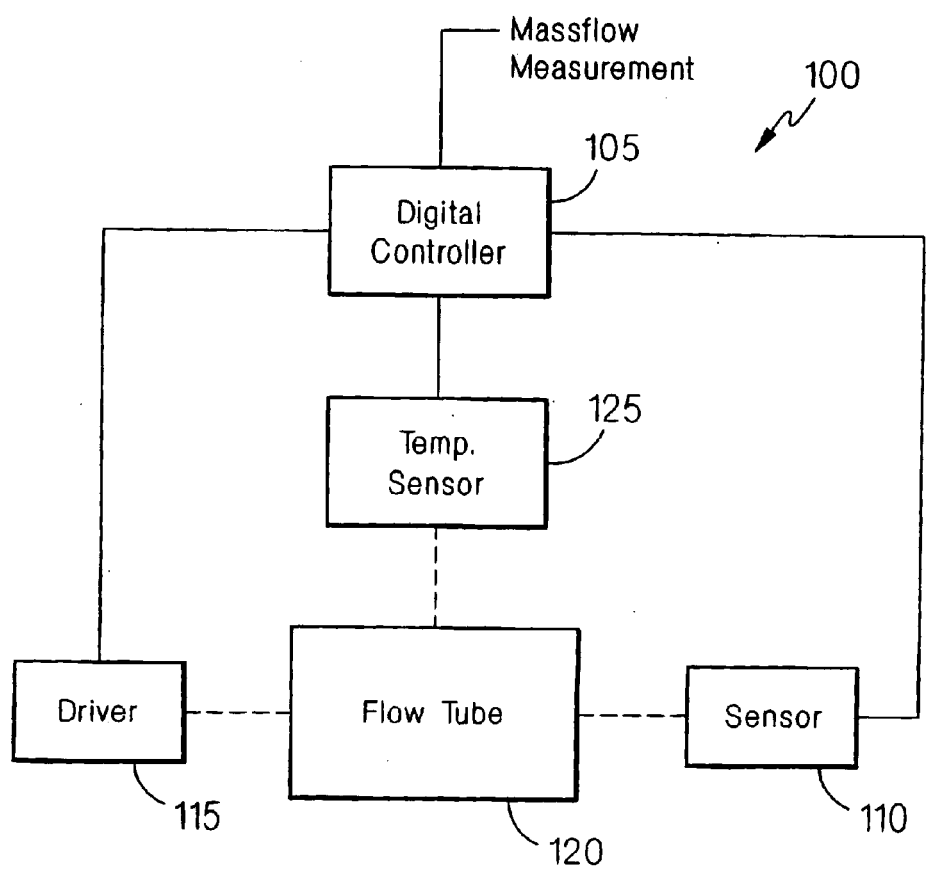
FIG. 1 is a block diagram of a digital mass flowmeter.

Referring to FIG. 1, a digital mass flowmeter 100 includes a digital controller 105, one or more motion sensors 110, one or more drivers 115, a conduit 120 (also referred to as a flowtube), and a temperature sensor 125. The digital controller 105 may be implemented using one or more of, for example, a processor, a field-programmable gate array, an ASIC, other programmable logic or gate arrays, or programmable logic with a processor core. The digital controller generates a measurement of mass flow through the conduit 120 based at least on signals received from the motion sensors 110. The digital controller also controls the drivers 115 to induce motion in the conduit 120. This motion is sensed by the motion sensors 110.

Mass flow through the conduit 120 is related to the motion induced in the conduit in response to a driving force supplied by the drivers 115. In particular, mass flow is related to the phase and frequency of the motion, as well as to the temperature of the conduit. The digital mass flowmeter also may provide a measurement of the density of material flowing through the conduit. The density is related to the frequency of the motion and the temperature of the conduit. Many of the described techniques are applicable to a densitometer that provides a measure of density rather than a measure of mass flow.

The temperature in the conduit, which is measured using the temperature sensor 125, affects certain properties of the conduit, such as its stiffness and dimensions. The digital controller compensates for these temperature effects. The temperature of the digital controller 105 affects, for example, the operating frequency of the digital controller. In general, the effects of controller temperature are sufficiently small to be considered negligible. However, in some instances, the digital controller may measure the controller temperature using a solid state device and may compensate for effects of the controller temperature.

A. Mechanical Design

Figure 2A:
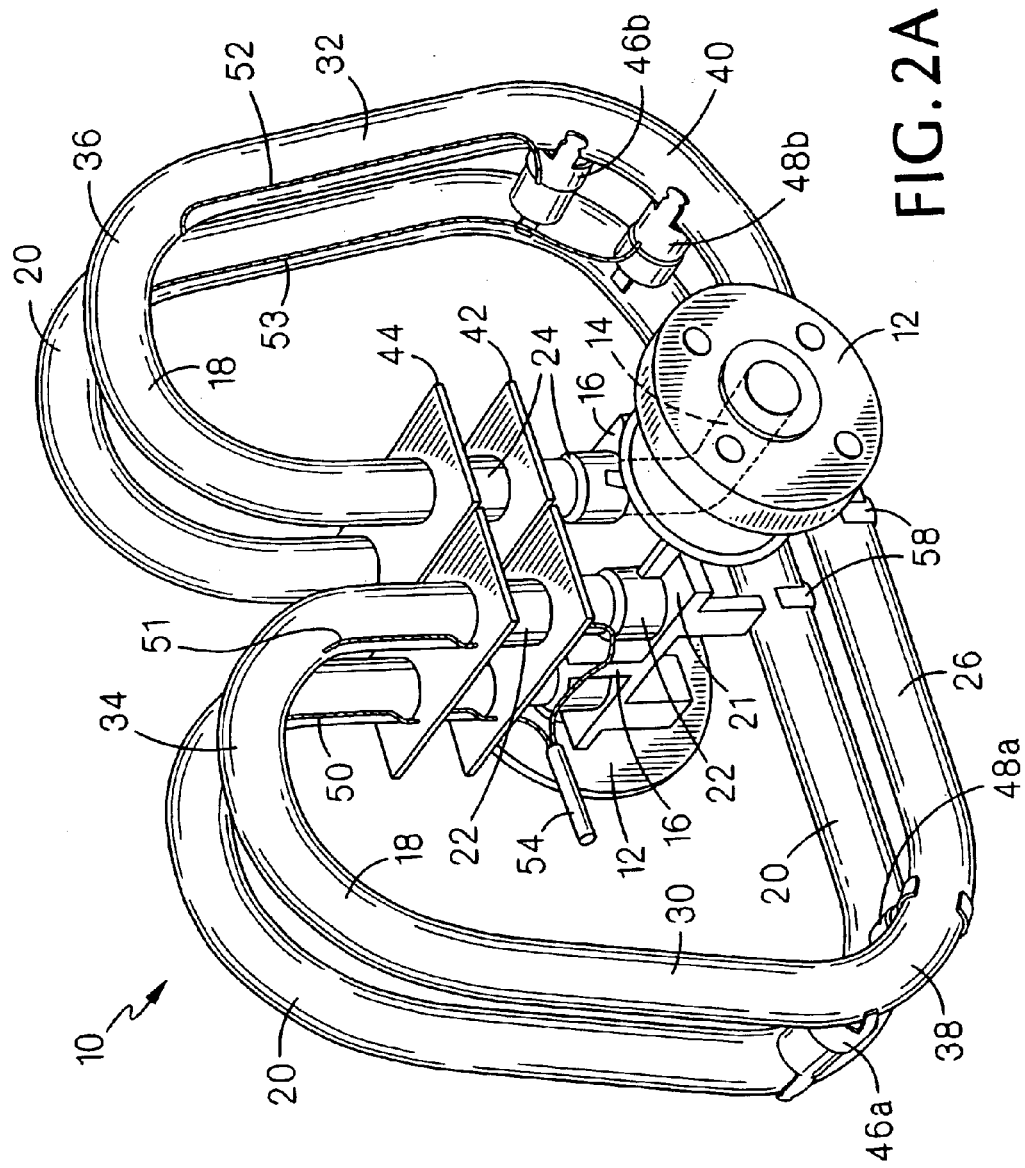

In one implementation, as illustrated in FIGS. 2A and 2B, the conduit 120 is designed to be inserted in a pipeline (not shown) having a small section removed or reserved to make room for the conduit. The conduit 120 includes mounting flanges 12 for connection to the pipeline, and a central manifold block 16 supporting two parallel planar loops 18 and 20 that are oriented perpendicularly to the pipeline. An electromagnetic driver 46 and a sensor 48 are attached between each end of loops 18 and 20. Each of the two drivers 46 corresponds to a driver 115 of FIG. 1, while each of the two sensors 48 corresponds to a sensor 120 of FIG. 1.

The drivers 46 on opposite ends of the loops are energized with current of equal magnitude but opposite sign (i.e., currents that are 180° out-of-phase) to cause straight sections 26 of the loops 18, 20 to rotate about their co-planar perpendicular bisector 56, which intersects the tube at point P (FIG. 2B). Repeatedly reversing (e.g., controlling sinusoidally) the energizing current supplied to the drivers causes each straight section 26 to undergo oscillatory motion that sweeps out a bow tie shape in the horizontal plane about line 56—56, the axis of symmetry of the loop. The entire lateral excursion of the loops at the lower rounded turns 38 and 40 is small, on the order of 1/16 of an inch for a two foot long straight section 26 of a pipe having a one inch diameter. The frequency of oscillation is typically about 80 to 90 Hertz.

B. Conduit Motion

Figure 3C:
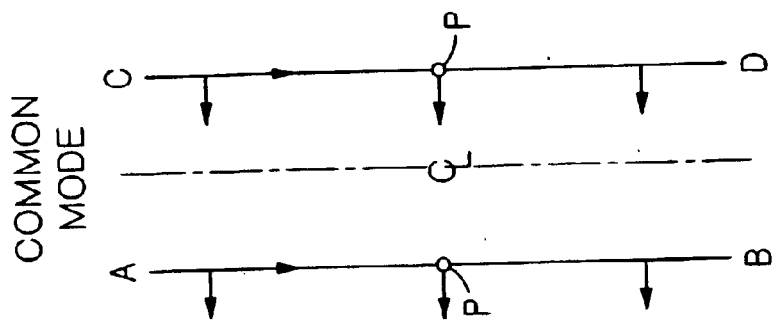
FIGS. 3A–3C are schematic representations of three modes of motion of the flowmeter of FIG. 1.
Figure 3B:
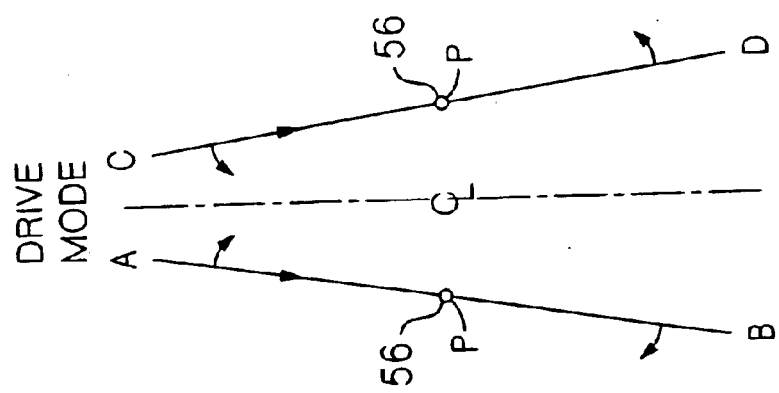
Figure 3A:
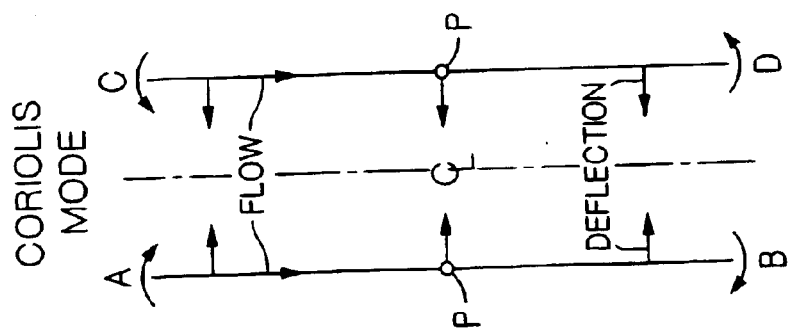

The motion of the straight sections of loops 18 and 20 are shown in three modes in FIGS. 3A, 3B and 3C. In the drive mode shown in FIG. 3B, the loops are driven 180° out-of-phase about their respective points P so that the two loops rotate synchronously but in the opposite sense. Consequently, respective ends such as A and C periodically come together and go apart.

The drive motion shown in FIG. 3B induces the Coriolis mode motion shown in FIG. 3A, which is in opposite directions between the loops and moves the straight sections 26 slightly toward (or away) from each other. The Coriolis effect is directly related to mvW, where m is the mass of material in a cross section of a loop, v is the velocity at which the mass is moving (the volumetric flow rate), W is the angular velocity of the loop (W=$W_o$ sin $\omega t$), and mv is the mass flow rate. The Coriolis effect is greatest when the two straight sections are driven sinusoidally and have a sinusoidally varying angular velocity. Under these conditions, the Coriolis effect is 90° out-of-phase with the drive signal.

FIG. 3C shows an undesirable common mode motion that deflects the loops in the same direction. This type of motion might be produced by an axial vibration in the pipeline in the embodiment of FIGS. 2A and 2B because the loops are perpendicular to the pipeline.

The type of oscillation shown in FIG. 3B is called the antisymmetrical mode, and the Coriolis mode of FIG. 3A is called the symmetrical mode. The natural frequency of oscillation in the antisymmetrical mode is a function of the torsional resilience of the legs. Ordinarily the resonant frequency of the antisymmetrical mode for conduits of the shape shown in FIGS. 2A and 2B is higher than the resonant frequency of the symmetrical mode. To reduce the noise sensitivity of the mass flow measurement, it is desirable to maximize the Coriolis force for a given mass flow rate. As noted above, the loops are driven at their resonant frequency, and the Coriolis force is directly related to the frequency at which the loops are oscillating (i.e., the angular velocity of the loops). Accordingly, the loops are driven in the antisymmetrical mode, which tends to have the higher resonant frequency.

Other implementations may include different conduit designs. For example, a single loop or a straight tube section may be employed as the conduit.

C. Electronic Design

The digital controller 105 determines the mass flow rate by processing signals produced by the sensors 48 (i.e., the motion sensors 110) located at opposite ends of the loops. The signal produced by each sensor includes a component corresponding to the relative velocity at which the loops are driven by a driver positioned next to the sensor and a component corresponding to the relative velocity of the loops due to Coriolis forces induced in the loops. The loops are driven in the antisymmetrical mode, so that the components of the sensor signals corresponding to drive velocity are equal in magnitude but opposite in sign. The resulting Coriolis force is in the symmetrical mode so that the components of the sensor signals corresponding to Coriolis velocity are equal in magnitude and sign. Thus, differencing the signals cancels out the Coriolis velocity components and results in a difference that is proportional to the drive velocity. Similarly, summing the signals cancels out the drive velocity components and results in a sum that is proportional to the Coriolis velocity, which, in turn, is proportional to the Coriolis force. This sum then may be used to determine the mass flow rate.

1. Analog Control System

Figure 4:
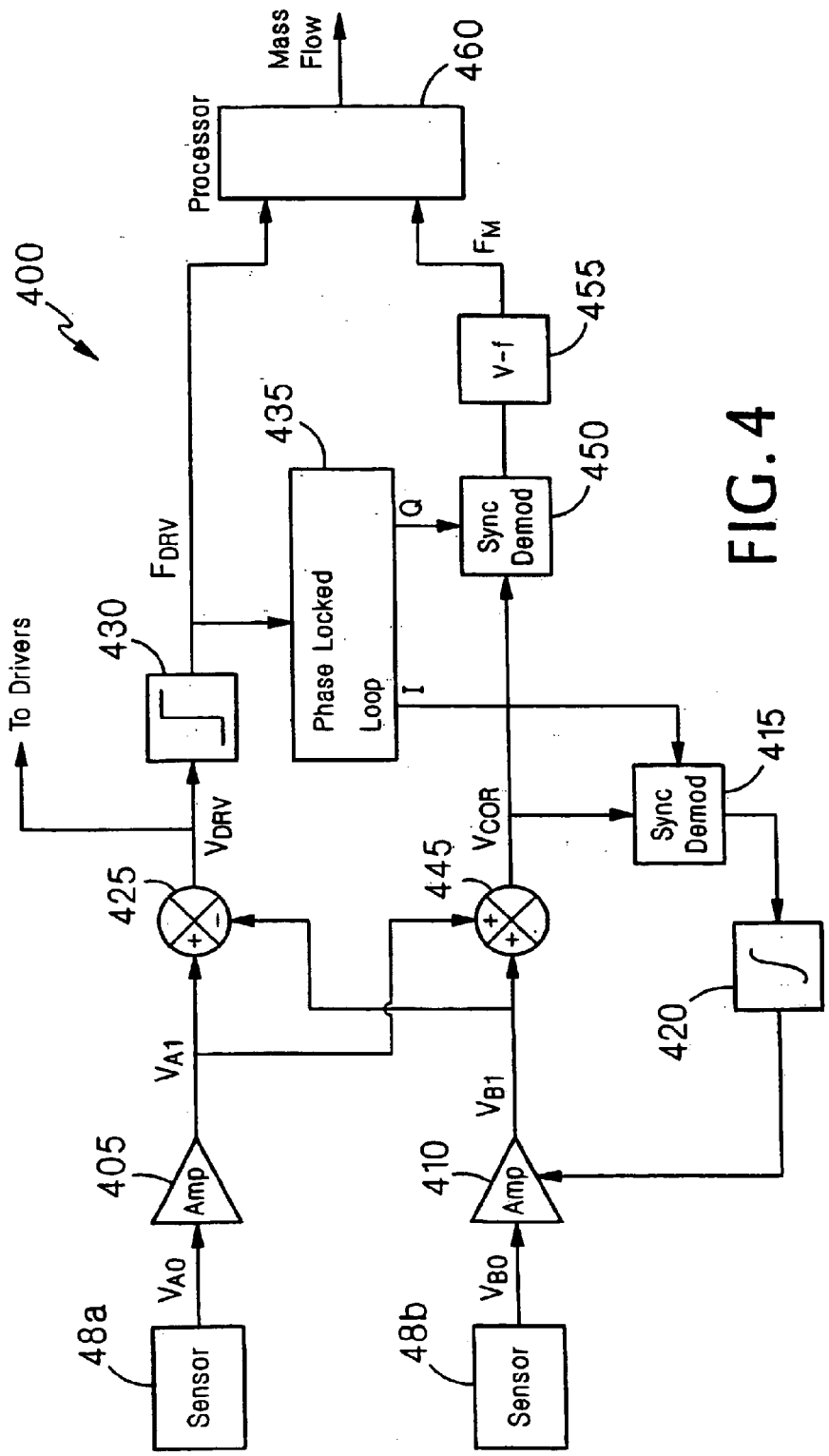
FIG. 4 is a block diagram of an analog control and measurement circuit.

The digital mass flowmeter 100 provides considerable advantages over traditional, analog mass flowmeters. For use in later discussion, FIG. 4 illustrates an analog control system 400 of a traditional mass flowmeter. The sensors 48 each produce a voltage signal, with signal $V_{A0}$ being produced by sensor 48a and signal $V_{B0}$ being produced by sensor 48b. $V_{A0}$ and $V_{B0}$ correspond to the velocity of the loops relative to each other at the positions of the sensors. Prior to processing, signals $V_{A0}$ and $V_{B0}$ are amplified at respective input amplifiers 405 and 410 to produce signals $V_{A1}$ and $V_{B1}$. To correct for imbalances in the amplifiers and the sensors, input amplifier 410 has a variable gain that is controlled by a balance signal coming from a feedback loop that contains a synchronous demodulator 415 and an integrator 420.

At the output of amplifier 405, signal $V_{A1}$ is of the form:

$$V_{A1} = V_D \sin \omega t + V_C \cos \omega t,$$

and, at the output of amplifier 410, signal $V_{B1}$ is of the form:

$$V_{B1} = -V_D \sin \omega t + V_C \cos \omega t,$$

where $V_D$ and $V_C$ are, respectively, the drive voltage and the Coriolis voltage, and $\omega$ is the drive mode angular frequency.

Voltages $V_{A1}$ and $V_{B1}$ are differenced by operational amplifier 425 to produce:

$$V_{DRV} = V_{A1} - V_{B1} = 2V_D \sin \omega t,$$

where $V_{DRV}$ corresponds to the drive motion and is used to power the drivers. In addition to powering the drivers, $V_{DRV}$ is supplied to a positive going zero crossing detector 430 that produces an output square wave $F_{DRV}$ having a frequency corresponding to that of $V_{DRV}$ ($\omega=2\pi F_{DRV}$). $F_{DRV}$ is used as the input to a digital phase locked loop circuit 435. $F_{DRV}$ also is supplied to a processor 440.

Voltages $V_{A1}$ and $V_{B1}$ are summed by operational amplifier 445 to produce:

$$V_{COR}=V_{A1}+V_{B1}=2V_C \cos \omega t,$$

where $V_{COR}$ is related to the induced Coriolis motion.

$V_{COR}$ is supplied to a synchronous demodulator 450 that produces an output voltage $V_M$ that is directly proportional to mass by rejecting the components of $V_{COR}$ that do not have the same frequency as, and are not in phase with, a gating signal Q. The phase locked loop circuit 435 produces Q, which is a quadrature reference signal that has the same frequency ($\omega$) as $V_{DRV}$ and is 90° out of phase with $V_{DRV}$ (i.e., in phase with $V_{COR}$). Accordingly, synchronous demodulator 450 rejects frequencies other than co so that $V_M$ corresponds to the amplitude of $V_{COR}$ at $\omega$. This amplitude is directly proportional to the mass in the conduit.

$V_M$ is supplied to a voltage-to-frequency converter 455 that produces a square wave signal $F_M$ having a frequency that corresponds to the amplitude of $V_M$. The processor 440 then divides $F_M$ by $F_{DRV}$ to produce a measurement of the mass flow rate.

Digital phase locked loop circuit 435 also produces a reference signal I that is in phase with $V_{DRV}$ and is used to gate the synchronous demodulator 415 in the feedback loop is controlling amplifier 410. When the gains of the input amplifiers 405 and 410 multiplied by the drive components of the corresponding input signals are equal, the summing operation at operational amplifier 445 produces zero drive component (i.e., no signal in phase with $V_{DRV}$) in the signal $V_{COR}$. When the gains of the input amplifiers 405 and 410 are not equal, a drive component exists in $V_{COR}$. This drive component is extracted by synchronous demodulator 415 and integrated by integrator 420 to generate an error voltage that corrects the gain of input amplifier 410. When the gain is too high or too low, the synchronous demodulator 415 produces an output voltage that causes the integrator to change the error voltage that modifies the gain. When the gain reaches the desired value, the output of the synchronous modulator goes to zero and the error voltage stops changing to maintain the gain at the desired value.

2. Digital Control System

Figure 5:
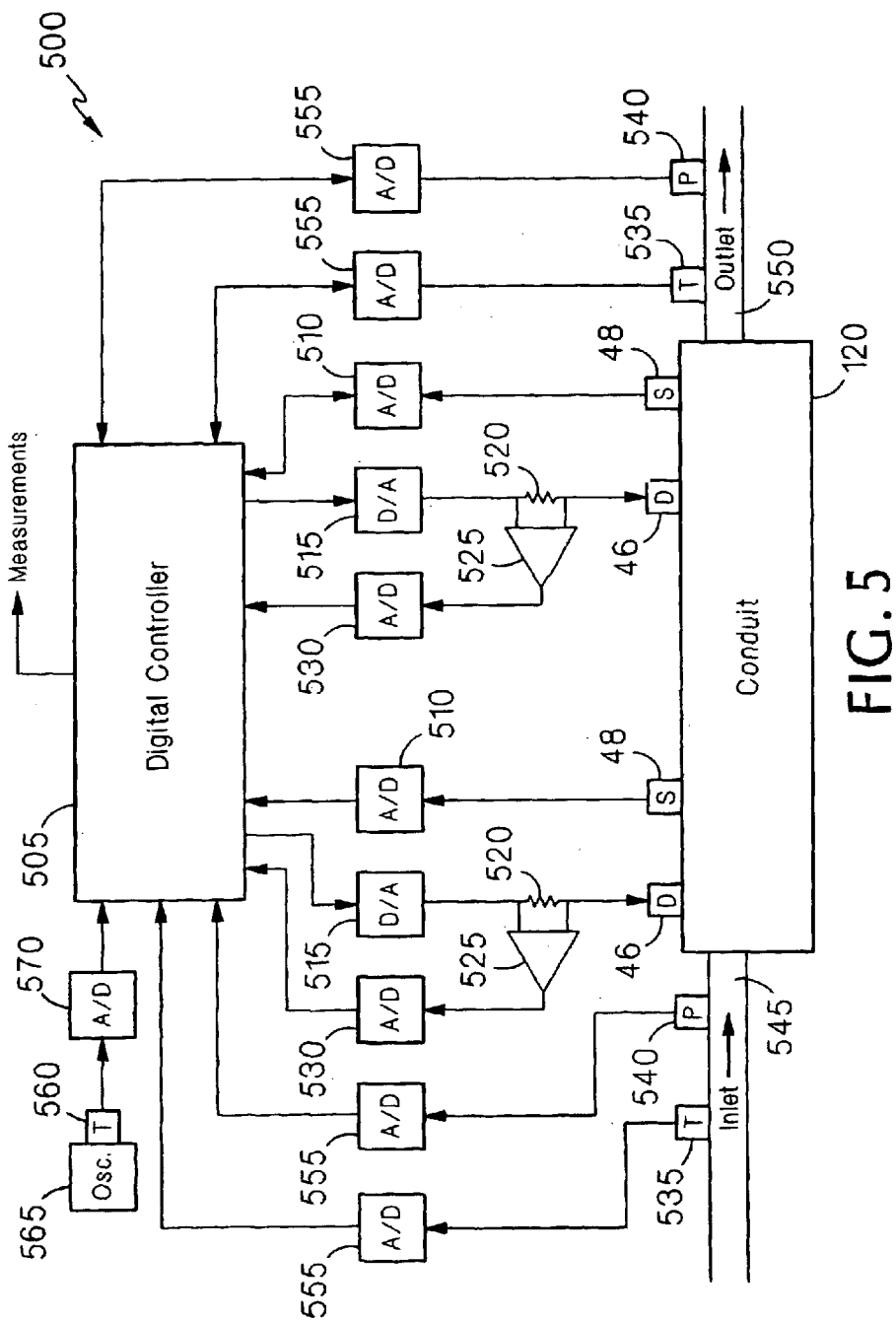
FIG. 5 is a block diagram of a digital mass flowmeter.

FIG. 5 provides a block diagram of an implementation 500 of the digital mass flowmeter 100 that includes the conduit 120, drivers 46, and sensors 48 of FIGS. 2A and 2B, along with a digital controller 505. Analog signals from the sensors 48 are converted to digital signals by analog-to-digital ("A/D") converters 510 and supplied to the controller 505. The A/D converters may be implemented as separate converters, or as separate channels of a single converter.

Digital-to-analog ("D/A") converters 515 convert digital control signals from the controller 505 to analog signals for driving the drivers 46. The use of a separate drive signal for each driver has a number of advantages. For example, the system may easily switch between symmetrical and antisymmetrical drive modes for diagnostic purposes. In other implementations, the signals produced by converters 515 may be amplified by amplifiers prior to being supplied to the drivers 46. In still other implementations, a single D/A converter may be used to produce a drive signal applied to both drivers, with the drive signal being inverted prior to being provided to one of the drivers to drive the conduit 120 in the antisymmetrical mode.

High precision resistors 520 and amplifiers 525 are used to measure the current supplied to each driver 46. A/D converters 530 convert the measured current to digital signals and supply the digital signals to controller 505. The controller 505 uses the measured currents in generating the driving signals.

Temperature sensors 535 and pressure sensors 540 measure, respectively, the temperature and the pressure at the inlet 545 and the outlet 550 of the conduit. A/D converters 555 convert the measured values to digital signals and supply the digital signals to the controller 505. The controller 505 uses the measured values in a number of ways. For example, the difference between the pressure measurements may be used to determine a back pressure in the conduit. Since the stiffness of the conduit varies with the back pressure, the controller may account for conduit stiffness based on the determined back pressure.

An additional temperature sensor 560 measures the temperature of the crystal oscillator 565 used by the A/D converters. An A/D converter 570 converts this temperature measurement to a digital signal for use by the controller 505. The input/output relationship of the A/D converters varies with the operating frequency of the converters, and the operating frequency varies with the temperature of the crystal oscillator. Accordingly, the controller uses the temperature measurement to adjust the data provided by the A/D converters, or in system calibration.

Figure 6:
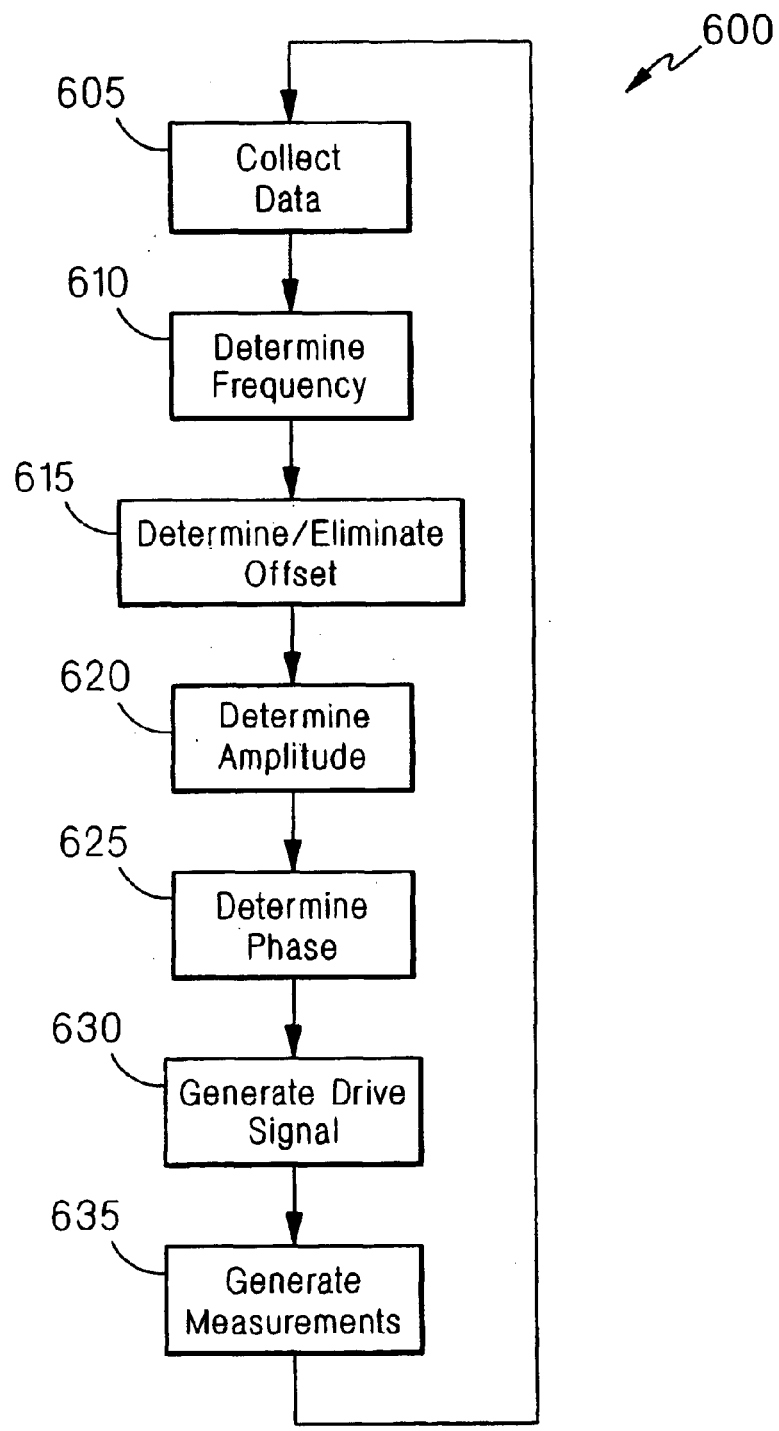
FIG. 6 is a flow chart showing operation of the meter of FIG. 5.

In the implementation of FIG. 5, the digital controller 505 processes the digitized sensor signals produced by the A/D converters 510 according to the procedure 600 illustrated in FIG. 6 to generate the mass flow measurement and the drive signal supplied to the drivers 46. Initially, the controller collects data from the sensors (step 605). Using this data, the controller determines the frequency of the sensor signals (step 610), eliminates zero offset from the sensor signals (step 615), and determines the amplitude (step 620) and phase (step 625) of the sensor signals. The controller uses these calculated values to generate the drive signal (step 630) and to generate the mass flow and other measurements (step 635). After generating the drive signals and measurements, the controller collects a new set of data and repeats the procedure. The steps of the procedure 600 may be performed serially or in parallel, and may be performed in varying order.

Because of the relationships between frequency, zero offset, amplitude, and phase, an estimate of one may be used in calculating another. This leads to repeated calculations to improve accuracy. For example, an initial frequency determination used in determining the zero offset in the sensor signals may be revised using offset-eliminated sensor signals. In addition, where appropriate, values generated for a cycle may be used as starting estimates for a following cycle.

FIG. 5 provides a general description of the hardware included in a digital flowmeter. A more detailed description of a specific hardware implementation is provided in the attached appendix, which is incorporated by reference.

a. Data Collection

For ease of discussion, the digitized signals from the two sensors will be referred to as signals $SV_1$ and $SV_2$, with signal $SV_1$ coming from sensor 48a and signal $SV_2$ coming from sensor 48b. Although new data is generated constantly, it is assumed that calculations are based upon data corresponding to one complete cycle of both sensors. With sufficient data buffering, this condition will be true so long as the average time to process data is less than the time taken to collect the data. Tasks to be carried out for a cycle include deciding that the cycle has been completed, calculating the frequency of the cycle (or the frequencies of $SV_1$ and $SV_2$), calculating the amplitudes of $SV_1$ and $SV_2$, and calculating the phase difference between $SV_1$ and $SV_2$. In some implementations, these calculations are repeated for each cycle using the end point of the previous cycle as the start for the next. In other implementations, the cycles overlap by 180° or other amounts (e.g., 90°) so that a cycle is subsumed within the cycles that precede and follow it.

Figure 7A:
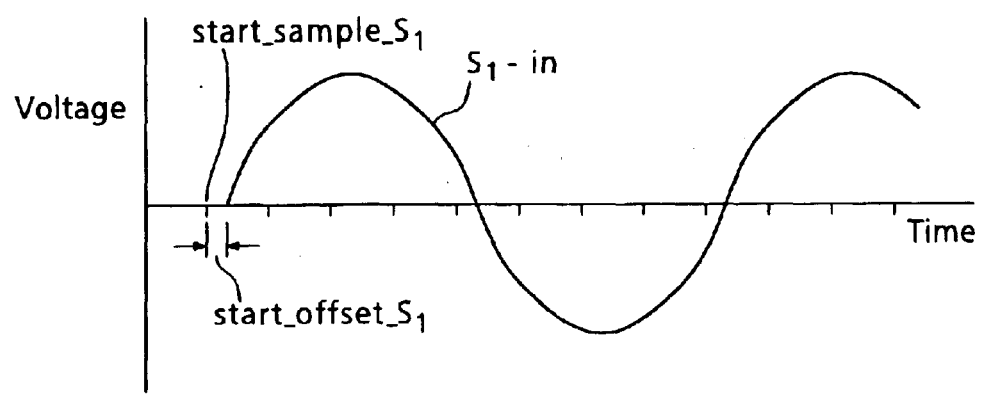
FIGS. 7A and 7B are graphs of sensor data.
Figure 7B:
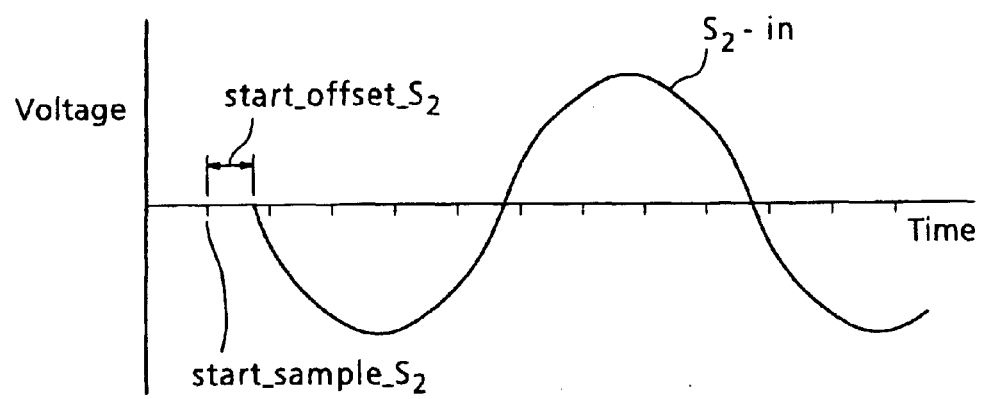

FIGS. 7A and 7B illustrate two vectors of sampled data from signals $SV_1$ and $SV_2$, which are named, respectively, sv1_in and sv2_in. The first sampling point of each vector is known, and corresponds to a zero crossing of the sine wave represented by the vector. For sv1_in, the first sampling point is the zero crossing from a negative value to a positive value, while for sv2_in the first sampling point is the zero crossing from a positive value to a negative value.

An actual starting point for a cycle (i.e., the actual zero crossing) will rarely coincide exactly with a sampling point. For this reason, the initial sampling points (start_sample_SV1 and start_sample_SV2) are the sampling points occurring just before the start of the cycle. To account for the difference between the first sampling point and the actual start of the cycle, the approach also uses the position (start_offset_SV1 or start_offset_SV2) between the starting sample and the next sample at which the cycle actually begins.

Since there is a phase offset between signals $SV_1$ and $SV_2$, sv1_in and sv2_in may start at different sampling points. If both the sample rate and the phase difference are high, there may be a difference of several samples between the start of sv1_in and the start of sv2_in. This difference provides a crude estimate of the phase offset, and may be used as a check on the calculated phase offset, which is discussed below. For example, when sampling at 55 kHz, one sample corresponds to approximately 0.5 degrees of phase shift, and one cycle corresponds to about 800 sample points.

When the controller employs functions such as the sum (A+B) and difference (A−B), with B weighted to have the same amplitude as A, additional variables (e.g., start_sample_sum and start_offset_sum) track the start of the period for each function. The sum and difference functions have a phase offset halfway between $SV_1$ and $SV_2$.

In one implementation, the data structure employed to store the data from the sensors is a circular list for each sensor, with a capacity of at least twice the maximum number of samples in a cycle. With this data structure, processing may be carried out on data for a current cycle while interrupts or other techniques are used to add data for a following cycle to the lists.

Processing is performed on data corresponding to a full cycle to avoid errors when employing approaches based on sine-waves. Accordingly, the first task in assembling data for a cycle is to determine where the cycle begins and ends. When nonoverlapping cycles are employed, the beginning of the cycle may be identified as the end of the previous cycle. When overlapping cycles are employed, and the cycles overlap by 180°, the beginning of the cycle may be identified as the midpoint of the previous cycle, or as the endpoint of the cycle preceding the previous cycle.

The end of the cycle may be first estimated based on the parameters of the previous cycle and under the assumption that the parameters will not change by more than a predetermined amount from cycle to cycle. For example, five percent may be used as the maximum permitted change from the last cycle's value, which is reasonable since, at sampling rates of 55 kHz, repeated increases or decreases of five percent in amplitude or frequency over consecutive cycles would result in changes of close to 5,000 percent in one second.

By designating five percent as the maximum permissible increase in amplitude and frequency, and allowing for a maximum phase change of 5° in consecutive cycles, a conservative estimate for the upper limit on the end of the cycle for signal $SV_1$ may be determined as:

$$\text{end\_sample\_SV1} \le \text{start\_sample\_SV1} + \frac{365}{360} * \frac{\text{sample\_rate}}{\text{est\_freq} * 0.95}$$

where start_sample_SV1 is the first sample of sv1_in, sample_rate is the sampling rate, and est_freq is the frequency from the previous cycle. The upper limit on the end of the cycle for signal $SV_2$ (end_sample_SV2) may be determined similarly.

After the end of a cycle is identified, simple checks may be made as to whether the cycle is worth processing. A cycle may not be worth processing when, for example, the conduit has stalled or the sensor waveforms are severely distorted. Processing only suitable cycles provides considerable reductions in computation.

One way to determine cycle suitability is to examine certain points of a cycle to confirm expected behavior. As noted above, the amplitudes and frequency of the last cycle give useful starting estimates of the corresponding values for the current cycle. Using these values, the points corresponding to 30°, 150°, 210° and 330° of the cycle may be examined. If the amplitude and frequency were to match exactly the amplitude and frequency for the previous cycle, these points should have values corresponding to est_amp/2, est_amp/2, −est_amp/2, and −est_amp/2, respectively, where est_amp is the estimated amplitude of a signal (i.e., the amplitude from the previous cycle). Allowing for a five percent change in both amplitude and frequency, inequalities may be generated for each quarter cycle. For the 30° point, the inequality is $$\text{sv1\_in}\left(\text{start\_sample\_SV1} + \frac{30}{360} * \frac{\text{sample\_rate}}{\text{est\_freq} * 1.05}\right) > 0.475 * \text{est\_amp\_SV}$$

The inequalities for the other points have the same form, with the degree offset term (x/360) and the sign of the est_amp_SV1 term having appropriate values. These inequalities can be used to check that the conduit has vibrated in a reasonable manner.

Measurement processing takes place on the vectors sv1_in(start:end) and sv2_in(start:end) where:

start=min (start_sample_SV1, start_sample_SV2), and
end=max (end_sample_SV1, end_sample_SV2).

The difference between the start and end points for a signal is indicative of the frequency of the signal.

b. Frequency Determination

The frequency of a discretely-sampled pure sine wave may be calculated by detecting the transition between periods (i.e., by detecting positive or negative zero-crossings) and counting the number of samples in each period. Using this method, sampling, for example, an 82.2 Hz sine wave at 55 kHz will provide an estimate of frequency with a maximum error of 0.15 percent. Greater accuracy may be achieved by estimating the fractional part of a sample at which the zero-crossing actually occurred using, for example, start_offset_SV1 and start_offset_SV2. Random noise and zero offset may reduce the accuracy of this approach.

Figure 8A:
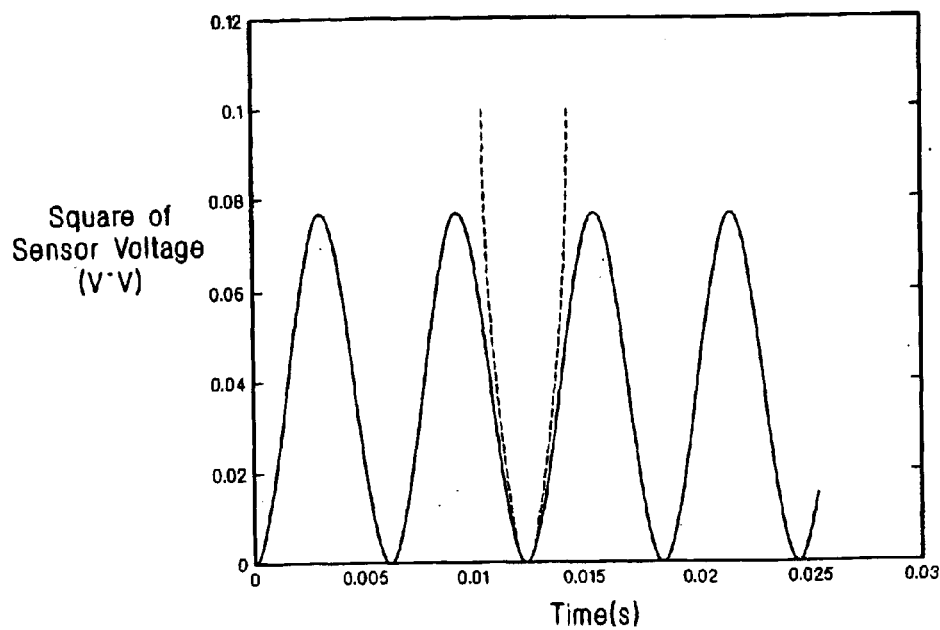
FIGS. 8A and 8B are graphs of sensor voltage relative to time.
Figure 8B:
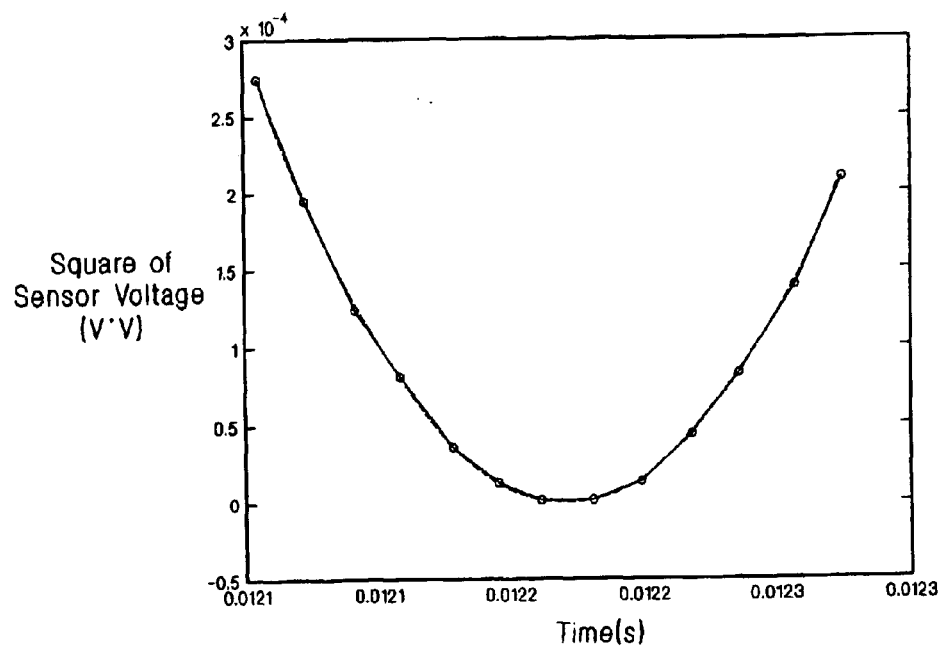

As illustrated in FIGS. 8A and 8B, a more refined method of frequency determination uses quadratic interpolation of the square of the sine wave. With this method, the square of the sine wave is calculated, a quadratic function is fitted to match the minimum point of the squared sine wave, and the zeros of the quadratic function are used to determine the frequency. If $$sv_t = A \sin x_t + \delta + \sigma \epsilon_t,$$

where $sv_t$ is the sensor voltage at time t, A is the amplitude of oscillation, $x_t$ is the radian angle at time t (i.e., $x_t = 2\pi f t$), $\delta$ is the zero offset, $\epsilon_t$ is a random variable with distribution N(0,1), and $\sigma$ is the variance of the noise, then the squared function is given by:

$$sv_t^2 = A^2 \sin^2 x_t + 2A(\delta + \sigma \epsilon_t) \sin x_t + 2\delta\sigma\epsilon_t + \delta^2 + \sigma^2 \epsilon_t^2.$$

When $x_t$ is close to $2\pi$, $\sin x_t$ and $\sin^2 x_t$ can be approximated as $x_{0t} = x_t - 2\pi$ and $x_{0t}^2$, respectively. Accordingly, for values of $x_t$ close to $2\pi$, $a_t$ can be approximated as:

$$a_t^2 \approx A^2 x_{0t}^2 + 2A(\delta + \sigma\epsilon_t)x_{0t} + 2\delta\sigma\epsilon_t + \delta^2 + \sigma^2 \epsilon_t^2$$

$$\approx (A^2 x_{0t}^2 + 2A\delta x_{0t} + \delta^2) + \sigma\epsilon_t(2Ax_{0t} + 2\delta + \sigma\epsilon_t).$$

This is a pure quadratic (with a non-zero minimum, assuming $\delta \neq 0$) plus noise, with the amplitude of the noise being dependent upon both $\sigma$ and $\delta$. Linear interpolation also could be used.

Error sources associated with this curve fitting technique are random noise, zero offset, and deviation from a true quadratic. Curve fitting is highly sensitive to the level of random noise. Zero offset in the sensor voltage increases the amplitude of noise in the sine-squared function, and illustrates the importance of zero offset elimination (discussed below). Moving away from the minimum, the square of even a pure sine wave is not entirely quadratic. The most significant extra term is of fourth order. By contrast, the most significant extra term for linear interpolation is of third order.

Degrees of freedom associated with this curve fitting technique are related to how many, and which, data points are used. The minimum is three, but more may be used (at greater computational expense) by using least-squares fitting. Such a fit is less susceptible to random noise. FIG. 8A illustrates that a quadratic approximation is good up to some 20° away from the minimum point. Using data points further away from the minimum will reduce the influence of random noise, but will increase the errors due to the non-quadratic terms (i.e., fourth order and higher) in the sine-squared function.

Figure 9:
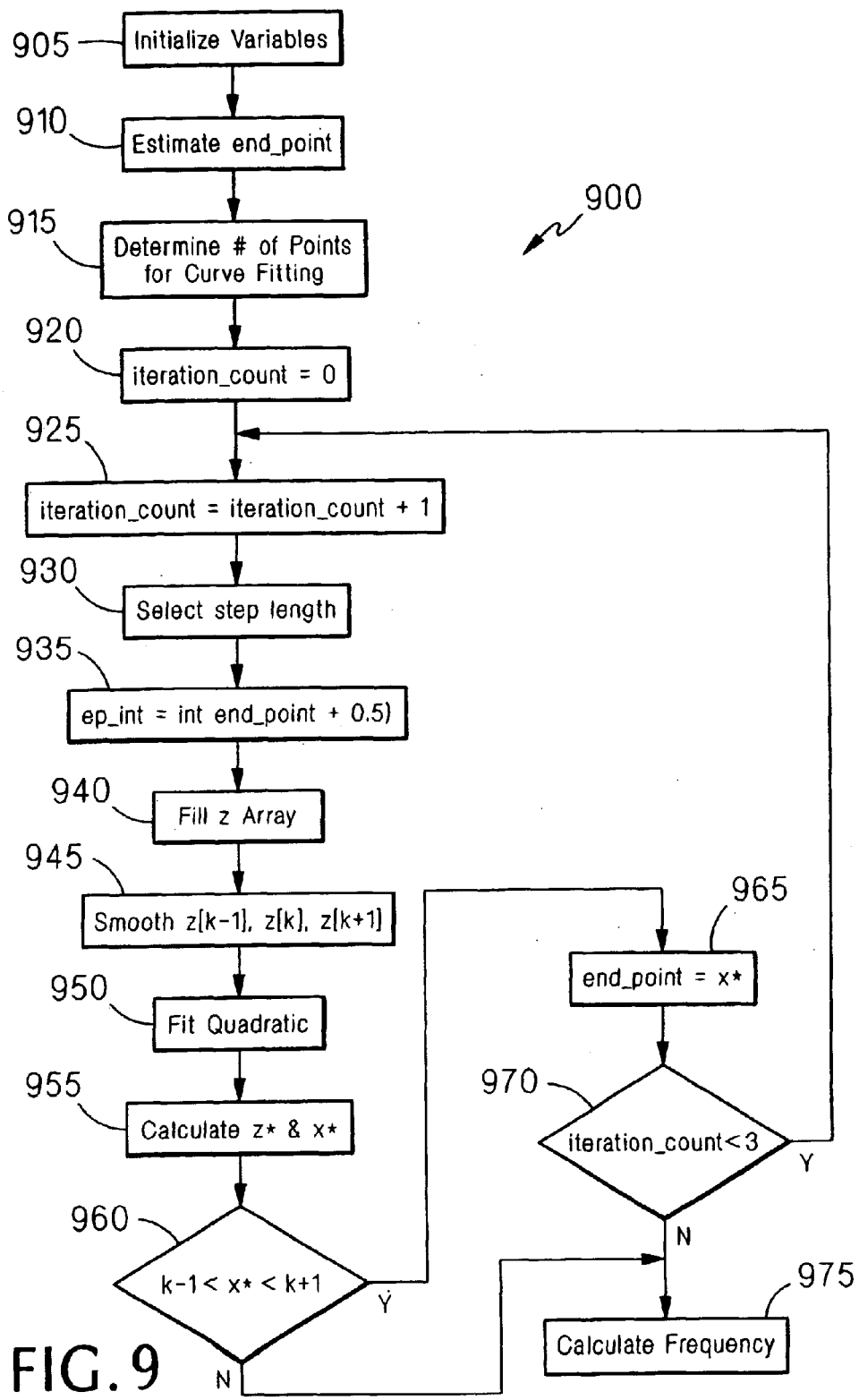
FIG. 9 is a flow chart of a curve fitting procedure.

FIG. 9 illustrates a procedure 900 for performing the curve fitting technique. As a first step, the controller initializes variables (step 905). These variables include end_point, the best estimate of the zero crossing point; ep_int, the integer value nearest to end_point; s[0 . . . i], the set of all sample points; z[k], the square of the sample point closest to end_point; z[0 . . . n−1], a set of squared sample points used to calculate end_point; n, the number of sample points used to calculate end_point (n=2k+1); step_length, the number of samples in s between consecutive values in z; and iteration_count, a count of the iterations that the controller has performed.

The controller then generates a first estimate of end_point (step 910). The controller generates this estimate by calculating an estimated zero-crossing point based on the estimated frequency from the previous cycle and searching around the estimated crossing point (forwards and backwards) to find the nearest true crossing point (i.e., the occurrence of consecutive samples with different signs). The controller then sets end_point equal to the sample point having the smaller magnitude of the samples surrounding the true crossing point.

Next, the controller sets n, the number of points for curve fitting (step 915). The controller sets n equal to 5 for a sample rate of 11 kHz, and to 21 for a sample rate of 44 kHz. The controller then sets iteration_count to 0 (step 920) and increments iteration_count (step 925) to begin the iterative portion of the procedure.

As a first step in the iterative portion of the procedure, the controller selects step_length (step 930) based on the value of iteration_count. The controller sets step_length equal to 6, 3, or 1 depending on whether iteration_count equals, respectively, 1, 2 or 3.

Next, the controller determines ep_int as the integer portion of the sum of end_point and 0.5 (step 935) and fills the z array (step 940). For example, when n equals 5, z[0]=s[ep_int−2*step_length]$^2$, z[1]=s[ep_int−step_length]$^2$, z[2]=s[ep_int]$^2$, z[3]=s[ep_int+step_length]$^2$, and z[4]=s[ep_int+2*step length]$^2$.

Next, the controller uses a filter, such as a Savitzky-Golay filter, to calculate smoothed values of z[k−1], z[k] and z[k+1] (step 945). Savitzky-Golay smoothing filters are discussed by Press et al. in *Numerical Recipes in C*, pp. 650–655 (2nd ed., Cambridge University Press, 1995), which is incorporated by reference. The controller then fits a quadratic to z[k−1], z[k] and z[k+1] (step 950), and calculates the minimum value of the quadratic (z*) and the corresponding position (x*) (step 955).

If x* is between the points corresponding to k−1 and k+1 (step 960), then the controller sets end_point equal to x* (step 965). Thereafter, if iteration_count is less than 3 (step 970), the controller increments iteration_count (step 925) and repeats the iterative portion of the procedure.

If x* is not between the points corresponding to k−1 and k+1 (step 960), or if iteration_count equals 3 (step 970), the controller exits the iterative portion of the procedure. The controller then calculates the frequency based on the difference between end-point and the starting point for the cycle, which is known (step 975).

In essence, the procedure 900 causes the controller to make three attempts to home in on end_point, using smaller step_lengths in each attempt. If the resulting minimum for any attempt falls outside of the points used to fit the curve (i.e., there has been extrapolation rather than interpolation), this indicates that either the previous or new estimate is poor, and that a reduction in step size is unwarranted.

The procedure 900 may be applied to at least three different sine waves produced by the sensors. These include signals $SV_1$ and $SV_2$ and the weighted sum of the two. Moreover, assuming that zero offset is eliminated, the frequency estimates produced for these signals are independent. This is clearly true for signals $SV_1$ and $SV_2$, as the errors on each are independent. It is also true, however, for the weighted sum, as long as the mass flow and the corresponding phase difference between signals $SV_1$ and $SV_2$ are large enough for the calculation of frequency to be based on different samples in each case. When this is true, the random errors in the frequency estimates also should be independent.

The three independent estimates of frequency can be combined to provide an improved estimate. This combined estimate is simply the mean of the three frequency estimates.

c. Zero Offset Compensation

An important error source in a Coriolis transmitter is zero offset in each of the sensor voltages. Zero offset is introduced into a sensor voltage signal by drift in the pre-amplification circuitry and the analog-to-digital converter. The zero offset effect may be worsened by slight differences in the pre-amplification gains for positive and negative voltages due to the use of differential circuitry. Each error source varies between transmitters, and will vary with transmitter temperature and more generally over time with component wear.

An example of the zero offset compensation technique employed by the controller is discussed in detail below. In general, the controller uses the frequency estimate and an integration technique to determine the zero offset in each of the sensor signals. The controller then eliminates the zero offset from those signals. After eliminating zero offset from signals $SV_1$ and $SV_2$, the controller may recalculate the frequency of those signals to provide an improved estimate of the frequency.

d. Amplitude Determination

The amplitude of oscillation has a variety of potential uses. These include regulating conduit oscillation via feedback, balancing contributions of sensor voltages when synthesizing driver waveforms, calculating sums and differences for phase measurement, and calculating an amplitude rate of change for measurement correction purposes.

In one implementation, the controller uses the estimated amplitudes of signals $SV_1$ and $SV_2$ to calculate the sum and difference of signals $SV_1$ and $SV_2$, and the product of the sum and difference. Prior to determining the sum and difference, the controller compensates one of the signals to account for differences between the gains of the two sensors. For example, the controller may compensate the data for signal $SV_2$ based on the ratio of the amplitude of signal $SV_1$ to the amplitude of signal $SV_2$ so that both signals have the same amplitude.

The controller may produce an additional estimate of the frequency based on the calculated sum. This estimate may be averaged with previous frequency estimates to produce a refined estimate of the frequency of the signals, or may replace the previous estimates.

The controller may calculate the amplitude according to a Fourier-based technique to eliminate the effects of higher harmonics. A sensor voltage $x(t)$ over a period $T$ (as identified using zero crossing techniques) can be represented by an offset and a series of harmonic terms as:

$$x(t) = a_0/2 + a_1\cos(\omega t) + a_2\cos(2\omega t) + a_3\cos(3\omega t) + \ldots +$$
$$b_1\sin(\omega t) + b_2\sin(2\omega t) + \ldots$$

With this representation, a non-zero offset $a_0$ will result in non-zero cosine terms $a_n$. Though the amplitude of interest is the amplitude of the fundamental component (i.e., the amplitude at frequency $\omega$), monitoring the amplitudes of higher harmonic components (i.e., at frequencies $k\omega$, where $k$ is greater than 1) may be of value for diagnostic purposes. The values of $a_n$ and $b_n$ may be calculated as:

$$a_n = \frac{2}{T}\int_0^T x(t)\cos n\omega t\, dt,$$

and $$b_n = \frac{2}{T}\int_0^T x(t)\sin n\omega t\, dt.$$

The amplitude, $A_n$, of each harmonic is given by:

$$A_n = \sqrt{a_n^2 + b_n^2}.$$

The integrals are calculated using Simpson's method with quadratic correction (described below). The chief computational expense of the method is calculating the pure sine and cosine functions.

e. Phase Determination

The controller may use a number of approaches to calculate the phase difference between signals $SV_1$ and $SV_2$. For example, the controller may determine the phase offset of each harmonic, relative to the starting time at t=0, as:

$$\varphi_n = \tan^{-1}\frac{a_n}{b_n}.$$

The phase offset is interpreted in the context of a single waveform as being the difference between the start of the cycle (i.e., the zero-crossing point) and the point of zero phase for the component of SV(t) of frequency co. Since the phase offset is an average over the entire waveform, it may be used as the phase offset from the midpoint of the cycle. Ideally, with no zero offset and constant amplitude of oscillation, the phase offset should be zero every cycle. The controller may determine the phase difference by comparing the phase offset of each sensor voltage over the same time period.

The amplitude and phase may be generated using a Fourier method that eliminates the effects of higher harmonics. This method has the advantage that it does not assume that both ends of the conduits are oscillating at the same frequency. As a first step in the method, a frequency estimate is produced using the zero crossings to measure the time between the start and end of the cycle. If linear variation in frequency is assumed, this estimate equals the time-averaged frequency over the period. Using the estimated, and assumed time-invariant, frequency $\omega$ of the cycle, the controller calculates:

$$I_1 = \frac{2\omega}{\pi}\int_0^{\frac{2\pi}{\omega}} SV(t)\sin(\omega t)\,dt, \text{ and}$$

$$I_2 = \frac{2\omega}{\pi}\int_0^{\frac{2\pi}{\omega}} SV(t)\cos(\omega t)\,dt,$$

where SV(t) is the sensor voltage waveform (i.e., $SV_1(t)$ or $SV_2(t)$). The controller then determines the estimates of the amplitude and phase:

$$\text{Amp} = \sqrt{I_1^2 + I_2^2}, \text{ and}$$

$$\text{Phase} = \tan^{-1}\frac{I_2}{I_1}.$$

The controller then calculates a phase difference, assuming that the average phase and frequency of each sensor signal is representative of the entire waveform. Since these frequencies are different for $SV_1$ and $SV_2$, the corresponding phases are scaled to the average frequency. In addition, the phases are shifted to the same starting point (i.e., the midpoint of the cycle on $SV_1$). After scaling, they are subtracted to provide the phase difference:

$$\text{scaled\_phase\_SV}_1 = \text{phase\_SV}_1 \frac{\text{av\_freq}}{\text{freq\_SV}_1},$$

$$\text{scaled\_shift\_SV}_2 = \frac{(\text{midpoint\_SV}_2 - \text{midpoint\_SV}_1)h\,\text{freq\_SV}_2}{360}, \text{ and}$$

$$\text{scaled\_phase\_SV}_2 = (\text{phase\_SV}_2 + \text{scale\_shift\_SV}_2) \frac{\text{av\_freq}}{\text{freq\_SV}_2},$$

where h is the sample length and the midpoints are defined in terms of samples:

$$\text{midpoint\_SV}_x = \frac{(\text{startpoint\_SV}_x + \text{endpoint\_SV}_x)}{2}$$

In general, phase and amplitude are not calculated over the same time-frame for the two sensors. When the flow rate is zero, the two cycle mid-points are coincident. However, they diverge at high flow rates so that the calculations are based on sample sets that are not coincident in time. This leads to increased phase noise in conditions of changing mass flow. At full flow rate, a phase shift of 4° (out of 360°) means that only 99% of the samples in the $SV_1$ and $SV_2$ data sets are coincident. Far greater phase shifts may be observed under aerated conditions, which may lead to even lower rates of overlap.

Figure 10:
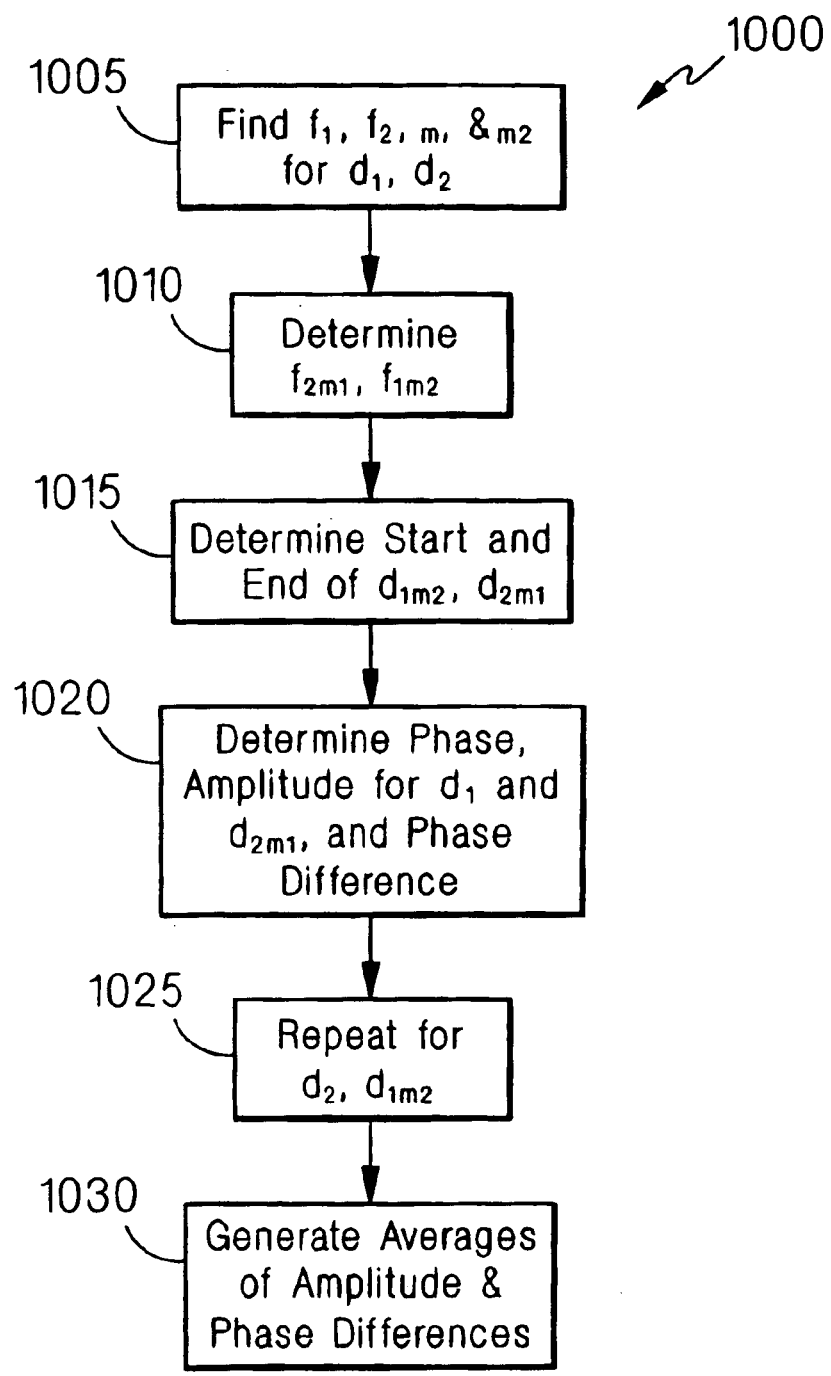
FIG. 10 is a flow chart of a procedure for generating phase differences.

FIG. 10 illustrates a modified approach 1000 that addresses this issue. First, the controller finds the frequencies ($f_1$, $f_2$) and the mid-points ($m_1$, $m_2$) of the $SV_1$ and $SV_2$ data sets ($d_1$, $d_2$) (step 1005). Assuming linear shift in frequency from the last cycle, the controller calculates the frequency of $SV_2$ at the midpoint of $SV_1$ ($f_{2m1}$) and the frequency of $SV_1$ at the midpoint of $SV_2$ ($f_{1m2}$) (step 1010).

The controller then calculates the starting and ending points of new data sets ($d_{1m2}$ and $d_{2m1}$) with mid-points $m_2$ and $m_1$ respectively, and assuming frequencies of $f_{1m2}$ and $f_{2m1}$ (step 1015). These end points do not necessarily coincide with zero crossing points. However, this is not a requirement for Fourier-based calculations.

The controller then carries out the Fourier calculations of phase and amplitude on the sets $d_1$ and $d_{2m1}$, and the phase difference calculations outlined above (step 1020). Since the mid-points of $d_1$ and $d_{2m1}$ are identical, scale-shift_$SV_2$ is always zero and can be ignored. The controller repeats these calculations for the data sets $d_2$ and $d_{1m2}$ (step 1025). The controller then generates averages of the calculated amplitude and phase difference for use in measurement generation (step 1030). When there is sufficient separation between the mid points $m_1$ and $m_2$, the controller also may use the two sets of results to provide local estimates of the rates of change of phase and amplitude.

The controller also may use a difference-amplitude method that involves calculating a difference between $SV_1$ and $SV_2$, squaring the calculated difference, and integrating the result. According to another approach, the controller synthesizes a sine wave, multiplies the sine wave by the difference between signals $SV_1$ and $SV_2$, and integrates the result. The controller also may integrate the product of signals $SV_1$ and $SV_2$, which is a sine wave having a frequency 2f (where f is the average frequency of signals $SV_1$ and $SV_2$), or may square the product and integrate the result. The controller also may synthesize a cosine wave comparable to the product sine wave and multiply the synthesized cosine wave by the product sine wave to produce a sine wave of frequency 4f that the controller then integrates. The controller also may use multiple ones of these approaches to produce separate phase measurements, and then may calculate a mean value of the separate measurements as the final phase measurement.

The difference-amplitude method starts with:

$$SV_1(t) = A_1 \sin\left(2\pi ft + \frac{\varphi}{2}\right) \text{ and } SV_2(t) = A_2 \sin\left(2\pi ft - \frac{\varphi}{2}\right),$$

where φ is the phase difference between the sensors. Basic trigonometric identities may be used to define the sum (Sum) and difference (Diff) between the signals as:

$$Sum \equiv SV_1(t) + \frac{A_1}{A_2} SV_2(t) = 2A_1 \cos\frac{\varphi}{2} \cdot \sin 2\pi ft, \text{ and}$$

$$Diff \equiv SV_1(t) - \frac{A_1}{A_2} SV_2(t) = 2A_1 \sin\frac{\varphi}{2} \cdot \cos 2\pi ft.$$

These functions have amplitudes of $2A_1 \cos((\varphi 2)$ and $2A_1 \sin((\varphi 2)$, respectively. The controller calculates data sets for Sum and Diff from the data for $SV_1$ and $SV_2$, and then uses one or more of the methods described above to calculate the amplitude of the signals represented by those data sets. The controller then uses the calculated amplitudes to calculate the phase difference, φ.

As an alternative, the phase difference may be calculated using the function Prod, defined as:

$$Prod \equiv SumxDiff = 4A_1^2 \cos\frac{\varphi}{2} \cdot \sin\frac{\varphi}{2} \cdot \cos 2\pi ft \cdot \sin 2\pi ft$$

$$= A_1^2 \sin\varphi \cdot \sin 4\pi ft,$$

which is a function with amplitude $A^2 \sin\varphi$ and frequency 2f. Prod can be generated sample by sample, and φ may be calculated from the amplitude of the resulting sine wave.

The calculation of phase is particularly dependent upon the accuracy of previous calculations (i.e., the calculation of the frequencies and amplitudes of $SV_1$ and $SV_2$). The controller may use multiple methods to provide separate (if not entirely independent) estimates of the phase, which may be combined to give an improved estimate.

f. Drive Signal Generation

The controller generates the drive signal by applying a gain to the difference between signals $SV_1$ and $SV_2$. The controller may apply either a positive gain (resulting in positive feedback) or a negative gain (resulting in negative feedback).

In general, the Q of the conduit is high enough that the conduit will resonate only at certain discrete frequencies. For example, the lowest resonant frequency for some conduits is between 65 Hz and 95 Hz, depending on the density of the process fluid, and irrespective of the drive frequency. As such, it is desirable to drive the conduit at the resonant frequency to minimize cycle-to-cycle energy loss. Feeding back the sensor voltage to the drivers permits the drive frequency to migrate to the resonant frequency.

As an alternative to using feedback to generate the drive signal, pure sine waves having phases and frequencies determined as described above may be synthesized and sent to the drivers. This approach offers the advantage of eliminating undesirable high frequency components, such as harmonics of the resonant frequency. This approach also permits compensation for time delays introduced by the analog-to-digital converters, processing, and digital-to-analog converters to ensure that the phase of the drive signal corresponds to the mid-point of the phases of the sensor signals. This compensation may be provided by determining the time delay of the system components and introducing a phase shift corresponding to the time delay.

Another approach to driving the conduit is to use square wave pulses. This is another synthesis method, with fixed (positive and negative) direct current sources being switched on and off at timed intervals to provide the required energy. The switching is synchronized with the sensor voltage phase. Advantageously, this approach does not require digital-to-analog converters.

In general, the amplitude of vibration of the conduit should rapidly achieve a desired value at startup, so as to quickly provide the measurement function, but should do so without significant overshoot, which may damage the meter. The desired rapid startup may be achieved by setting a very high gain so that the presence of random noise and the high Q of the conduit are sufficient to initiate motion of the conduit. In one implementation, high gain and positive feedback are used to initiate motion of the conduit. Once stable operation is attained, the system switches to a synthesis approach for generating the drive signals.

Referring to FIGS. 11A–13D, synthesis methods also may be used to initiate conduit motion when high gain is unable to do so. For example, if the DC voltage offset of the sensor voltages is significantly larger than random noise, the application of a high gain will not induce oscillatory motion. This condition is shown in FIGS. 11A–11D, in which a high gain is applied at approximately 0.3 seconds. As shown in FIGS. 11A and 11B, application of the high gain causes one of the drive signals to assume a large positive value (FIG. 11A) and the other to assume a large negative value (FIG. 11B). The magnitudes of the drive signals vary with noise in the sensor signals (FIGS. 11C and 11D). However, the amplified noise is insufficient to vary the sign of the drive signals so as to induce oscillation.

Figure 12A:
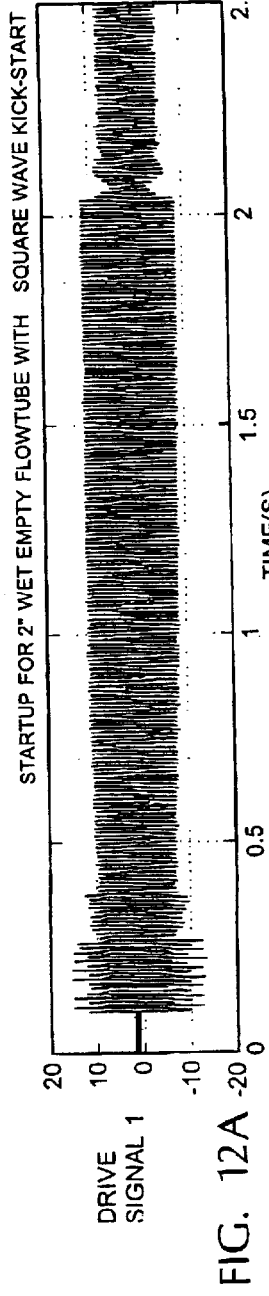
Figure 12B:
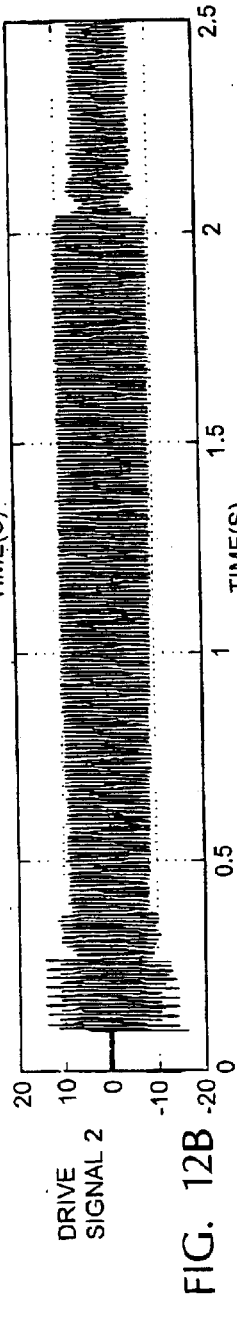
Figure 12C:
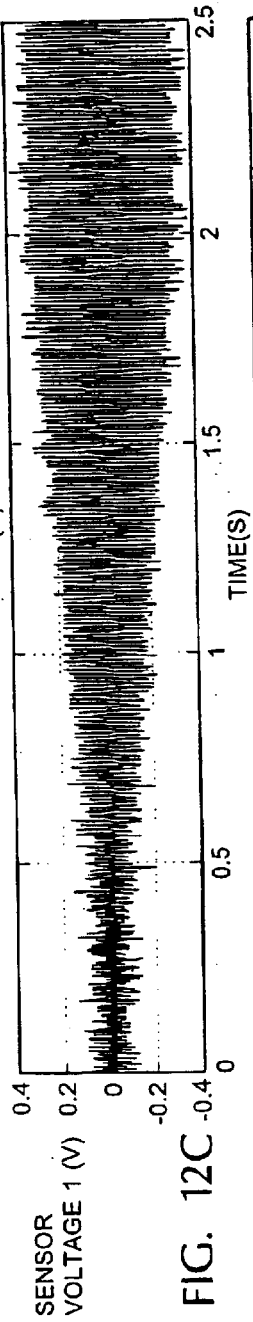
Figure 12D:
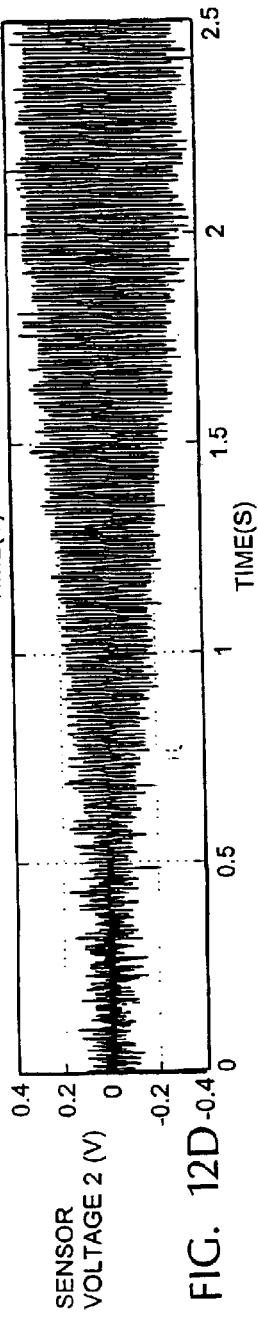

FIGS. 12A–12D illustrate that imposition of a square wave over several cycles can reliably cause a rapid startup of oscillation. Oscillation of a conduit having a two inch diameter may be established in approximately two seconds. The establishment of conduit oscillation is indicated by the reduction in the amplitude of the drive signals, as shown in FIGS. 12A and 12B. FIGS. 13A–13D illustrate that oscillation of a one inch conduit may be established in approximately half a second.

A square wave also may be used during operation to correct conduit oscillation problems. For example, in some circumstances, flow meter conduits have been known to begin oscillating at harmonics of the resonant frequency of the conduit, such as frequencies on the order of 1.5 kHz. When such high frequency oscillations are detected, a square wave having a more desirable frequency may be used to return the conduit oscillation to the resonant frequency.

g. Measurement Generation

The controller digitally generates the mass flow measurement in a manner similar to the approach used by the analog controller. The controller also may generate other measurements, such as density.

In one implementation, the controller calculates the mass flow based on the phase difference in degrees between the two sensor signals (phase_diff), the frequency of oscillation of the conduit (freq), and the process temperature (temp):

$T_z$=temp-$T_c$, noneu_mf=tan ($\pi$*phase_diff/180), and massflow=16 $(MF_1*T_z^2+MF_2*T_z+MF_3)$*noneu_mf/freq, where $T_c$ is a calibration temperature, $MF_1$–$MF_3$ are calibration constants calculated during a calibration procedure, and noneu_mf is the mass flow in non-engineering units.

The controller calculates the density based on the frequency of oscillation of the conduit and the process temperature:

$T_z$=temp-$T_c$, $c_2$=freq$^2$, and density=$(D_1*T_z^2+D_2*T_z+D_3)/c_2+D_4*T_z^2$, where $D_1$–$D_4$ are calibration constants generated during a calibration procedure.

D. Integration Techniques

Many integration techniques are available, with different techniques requiring different levels of computational effort and providing different levels of accuracy. In the described implementation, variants of Simpson's method are used. The basic technique may be expressed as:

$$\int_{t_n}^{t_{n+2}} y\, dt \approx \frac{h}{3}(y_n + 4y_{n+1} + y_{n+2}),$$

where $t_k$ is the time at sample k, $y_k$ is the corresponding function value, and h is the step length. This rule can be applied repeatedly to any data vector with an odd number of data points (i.e., three or more points), and is equivalent to fitting and integrating a cubic spline to the data points. If the number of data points happens to be even, then the so-called ⅜ths rule can be applied at one end of the interval:

$$\int_{t_n}^{t_{n+3}} y\, dt \approx \frac{3h}{8}(y_n + 3y_{n+1} + 3y_{n+2} + y_{n+3}).$$

As stated earlier, each cycle begins and ends at some offset (e.g., start_offset_SV1) from a sampling point. The accuracy of the integration techniques are improved considerably by taking these offsets into account. For example, in an integration of a half cycle sine wave, the areas corresponding to partial samples must be included in the calculations to avoid a consistent underestimate in the result.

Two types of function are integrated in the described calculations: either sine or sine-squared functions. Both are easily approximated close to zero where the end points occur. At the end points, the sine wave is approximately linear and the sine-squared function is approximately quadratic.

In view of these two types of functions, three different integration methods have been evaluated. These are Simpson's method with no end correction, Simpson's method with linear end correction, and Simpson's method with quadratic correction.

The integration methods were tested by generating and sampling pure sine and sine-squared functions, without simulating any analog-to-digital truncation error. Integrals were calculated and the results were compared to the true amplitudes of the signals. The only source of error in these calculations was due to the integration techniques. The results obtained are illustrated in tables A and B.

TABLE A

Integration of a sine function

| % err r (based on 1000 simulati ns) | Av. Err rs (%) | S.D. Error (%) | Max. Error (%) |
|---|---|---|---|
| Simpson Only | −3.73e−3 | 1.33e−3 | 6.17e−3 |
| Simpson + linear correction | 3.16e−8 | 4.89e−8 | 1.56e−7 |
| Simpson + quadratic correction | 2.00e−4 | 2.19e−2 | 5.18e−1 |

TABLE B

Integration of a sine-squared function

| % error (based on 1000 simulations | Av. Errors (%) | S.D. Error (%) | Max. Error (%) |
|---|---|---|---|
| Simpson Only | −2.21e−6 | 1.10e−6 | 4.39e−3 |
| Simpson + linear correction | 2.21e−6 | 6.93e−7 | 2.52e−6 |
| Simpson + quadratic correction | 2.15e−11 | 6.83e−11 | 1.88e−10 |

For sine functions, Simpson's method with linear correction was unbiased with the smallest standard deviation, while Simpson's method without correction was biased to a negative error and Simpson's method with quadratic correction had a relatively high standard deviation. For sine-squared functions, the errors were generally reduced, with the quadratic correction providing the best result. Based on these evaluations, linear correction is used when integrating sine functions and quadratic correction is used when integrating sine-squared functions.

E. Synchronous Modulation Technique

Figure 14:
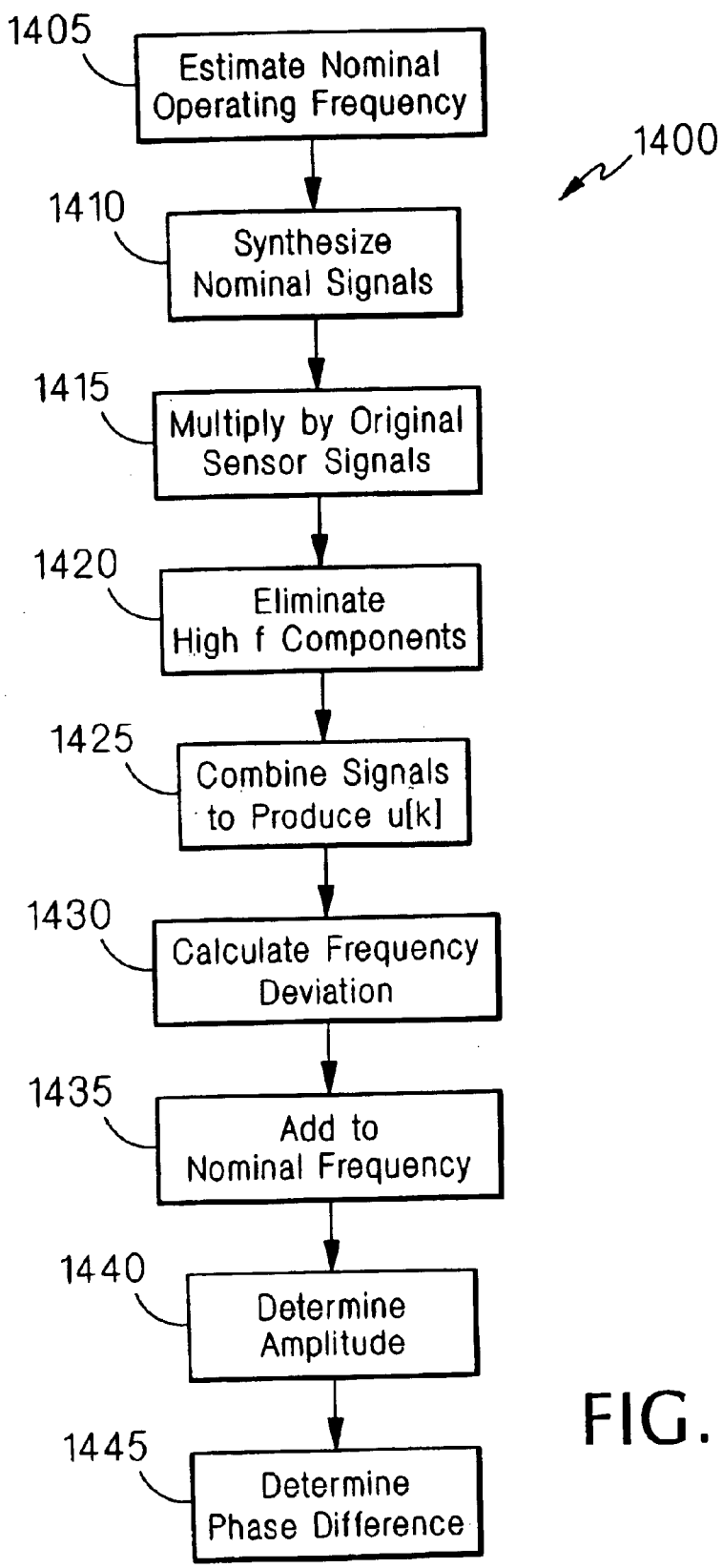
FIG. 14 is a flow chart of a procedure for measuring frequency, amplitude, and phase of sensor data using a synchronous modulation technique.

FIG. 14 illustrates an alternative procedure 1400 for processing the sensor signals. Procedure 1400 is based on synchronous modulation, such as is described by Denys et al., in "Measurement of Voltage Phase for the French Future Defence Plan Against Losses of Synchronism", IEEE Transactions on Power Delivery, 7(1), 62–69, 1992 and by Begovic et al. in "Frequency Tracking in Power Networks in the Presence of Harmonics", IEEE Transactions on Power Delivery, 8(2), 480–486, 1993, both of which are incorporated by reference.

First, the controller generates an initial estimate of the nominal operating frequency of the system (step 1405). The controller then attempts to measure the deviation of the frequency of a signal $x[k]$ (e.g., $SV_1$) from this nominal frequency:

$$x[k] = A \sin[(\omega_0 + \Delta\omega)kh + \Phi] + \epsilon(k),$$

where $A$ is the amplitude of the sine wave portion of the signal, $\omega_0$ is the nominal frequency (e.g., 88 Hz), $\Delta\omega$ is the deviation from the nominal frequency, $h$ is the sampling interval, $\Phi$ is the phase shift, and $\epsilon(k)$ corresponds to the added noise and harmonics.

To generate this measurement, the controller synthesizes two signals that oscillate at the nominal frequency (step 1410). The signals are phase shifted by 0 and $\pi/2$ and have amplitude of unity. The controller multiplies each of these signals by the original signal to produce signals $y_1$ and $y_2$ (step 1415):

$$y_1 = x[k]\cos(\omega_0 kh) = \frac{A}{2}\sin[(2\omega_0 + \Delta\omega)kh + \Phi] + \frac{A}{2}\sin(\Delta\omega kh + \Phi), \text{ and}$$

$$y_2 = x[k]\sin(\omega_0 kh) = \frac{A}{2}\cos[(2\omega_0 + \Delta\omega)kh + \Phi] + \frac{A}{2}\cos(\Delta\omega kh + \Phi),$$

where the first terms of $y_1$ and $y_2$ are high frequency (e.g., 176 Hz) components and the second terms are low frequency (e.g., 0 Hz) components. The controller then eliminates the high frequency components using a low pass filter (step 1420):

$$y'_1 = \frac{A}{2}\sin(\Delta\omega kh + \Phi) + \varepsilon_1[k], \text{ and}$$

$$y'_1 = \frac{A}{2}\cos(\Delta\omega kh + \Phi) + \varepsilon_2[k],$$

where $\epsilon_1[k]$ and $\epsilon_2[k]$ represent the filtered noise from the original signals. The controller combines these signals to produce $u[k]$ (step 1425):

$$u[k] = (y'_1[k] + jy'_2[k])(y'_1[k-1] + jy'_2[k-1])$$
$$= u_1[k] + ju_2[k]$$
$$= \frac{A^2}{4}\cos(\Delta\omega h) + j\frac{A^2}{4}\sin(\Delta\omega h),$$

which carries the essential information about the frequency deviation. As shown, $u_1[k]$ represents the real component of $u[k]$, while $u_2[k]$ represents the imaginary component.

The controller uses the real and imaginary components of $u[k]$ to calculate the frequency deviation, $\Delta f$ (step 1430):

$$\Delta f = \frac{1}{h}\arctan\frac{u_2[k]}{u_1[k]}.$$

The controller then adds the frequency deviation to the nominal frequency (step 1435) to give the actual frequency:

$$f = \Delta f + f_0.$$

The controller also uses the real and imaginary components of $u[k]$ to determine the amplitude of the original signal. In particular, the controller determines the amplitude as (step 1440):

$$A^2 = 4\sqrt{u_1^2[k] + u_2^2[k]}.$$

Next, the controller determines the phase difference between the two sensor signals (step 1445). Assuming that any noise ($\epsilon_1[k]$ and $\epsilon_2[k]$) remaining after application of the low pass filter described below will be negligible, noise free versions of $y_1[k]$ and $y_2[k]$ ($y_1^*[k]$ and $y_2[k]$) may be expressed as:

$$y_1^*[k] = \frac{A}{2}\sin(\Delta\omega kh + \Phi), \text{ and}$$

$$y_2^*[k] = \frac{A}{2}\cos(\Delta\omega kh - \Phi).$$

Multiplying these signals together gives:

$$v = y_1^* y_2^* = \frac{A^2}{8}[\sin(2\Phi) + \sin(2\Delta\omega kh)].$$

Filtering this signal by a low pass filter having a cutoff frequency near 0 Hz removes the unwanted component and leaves:

$$v' = \frac{A^2}{8}\sin(2\Phi),$$

from which the phase difference can be calculated as:

$$\Phi = \frac{1}{2}\arcsin\frac{8v'}{A^2}.$$

This procedure relies on the accuracy with which the operating frequency is initially estimated, as the procedure measures only the deviation from this frequency. If a good estimate is given, a very narrow filter can be used, which makes the procedure very accurate. For typical flowmeters, the operating frequencies are around 95 Hz (empty) and 82 Hz (full). A first approximation of half range (88 Hz) is used, which allows a low-pass filter cut-off of 13 Hz. Care must be taken in selecting the cut-off frequency as a very small cut-off frequency can attenuate the amplitude of the sine wave.

The accuracy of measurement also depends on the filtering characteristics employed. The attenuation of the filter in the dead-band determines the amount of harmonics rejection, while a smaller cutoff frequency improves the noise rejection.

F. Meter with PI Control

Figure 15A:
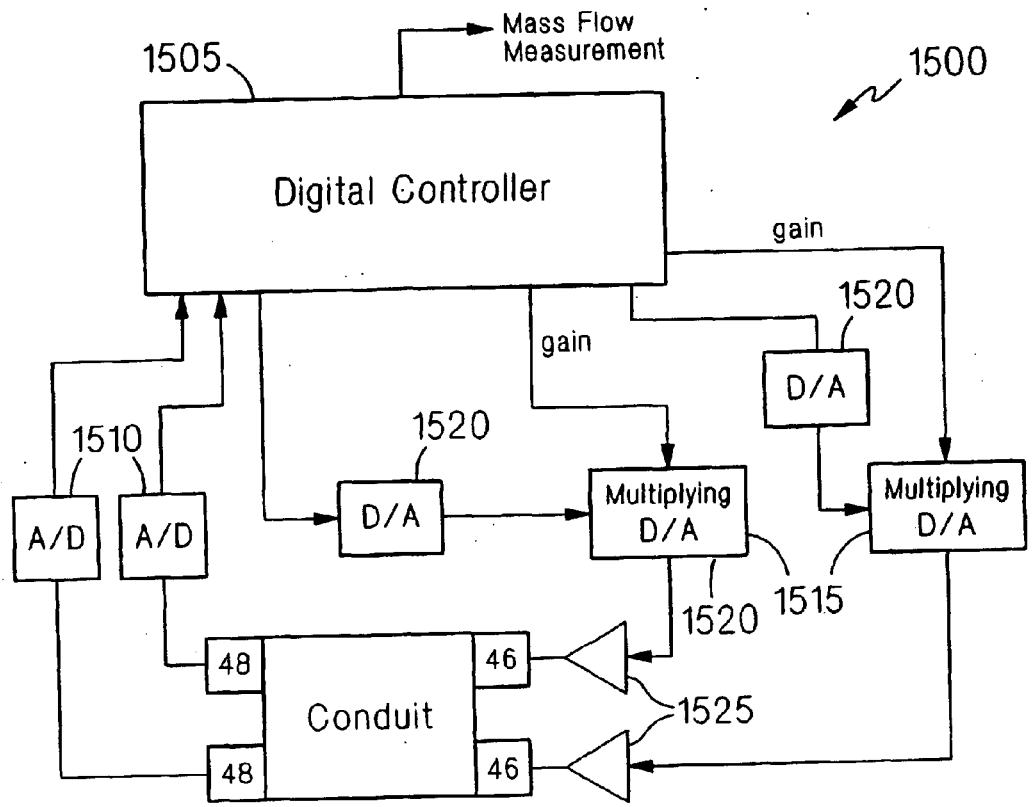
FIGS. 15A and 15B are block diagrams of a mass flowmeter.
Figure 15B:
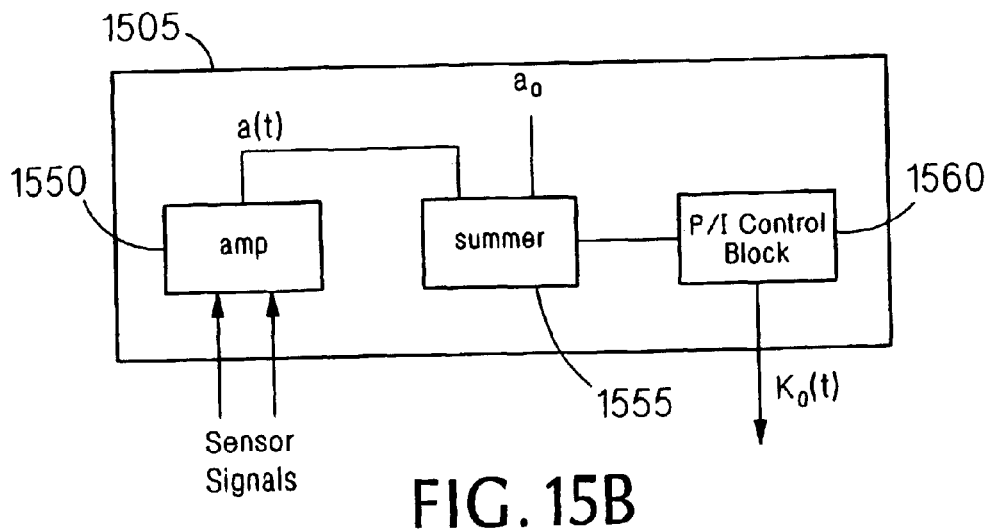

FIGS. 15A and 15B illustrate a meter 1500 having a controller 1505 that uses another technique to generate the signals supplied to the drivers. Analog-to-digital converters 1510 digitize signals from the sensors 48 and provide the digitized signals to the controller 1505. The controller 1505 uses the digitized signals to calculate gains for each driver, with the gains being suitable for generating desired oscillations in the conduit. The gains may be either positive or negative. The controller 1505 then supplies the gains to multiplying digital-to-analog converters 1515. In other implementations, two or more multiplying digital-to-analog converters arranged in series may be used to implement a single, more sensitive multiplying digital-to-analog converter.

The controller 1505 also generates drive signals using the digitized sensor signals. The controller 1505 provides these drive signals to digital-to-analog converters 1520 that convert the signals to analog signals that are supplied to the multiplying digital-to-analog converters 1515.

The multiplying digital-to-analog converters 1515 multiply the analog signals by the gains from the controller 1505 to produce signals for driving the conduit. Amplifiers 1525 then amplify these signals and supply them to the drivers 46. Similar results could be obtained by having the controller 1505 perform the multiplication performed by the multiplying digital-to-analog converter, at which point the multiplying digital-to-analog converter could be replaced by a standard digital-to-analog converter.

FIG. 15B illustrates the control approach in more detail. Within the controller 1505, the digitized sensor signals are provided to an amplitude detector 1550, which determines a measure, a(t), of the amplitude of motion of the conduit using, for example, the technique described above. A summer 1555 then uses the amplitude a(t) and a desired amplitude $a_0$ to calculate an error e(t) as:

$e(t)=a_o-a(t).$

The error e(t) is used by a proportional-integral ("PI") control block 1560 to generate a gain $K_0(t)$. This gain is multiplied by the difference of the sensor signals to generate the drive signal. The PI control block permits high speed response to changing conditions. The amplitude detector 1550, summer 1555, and PI control block 1560 may be implemented as software processed by the controller 1505, or as separate circuitry.

1. Control Procedure

Figure 16:
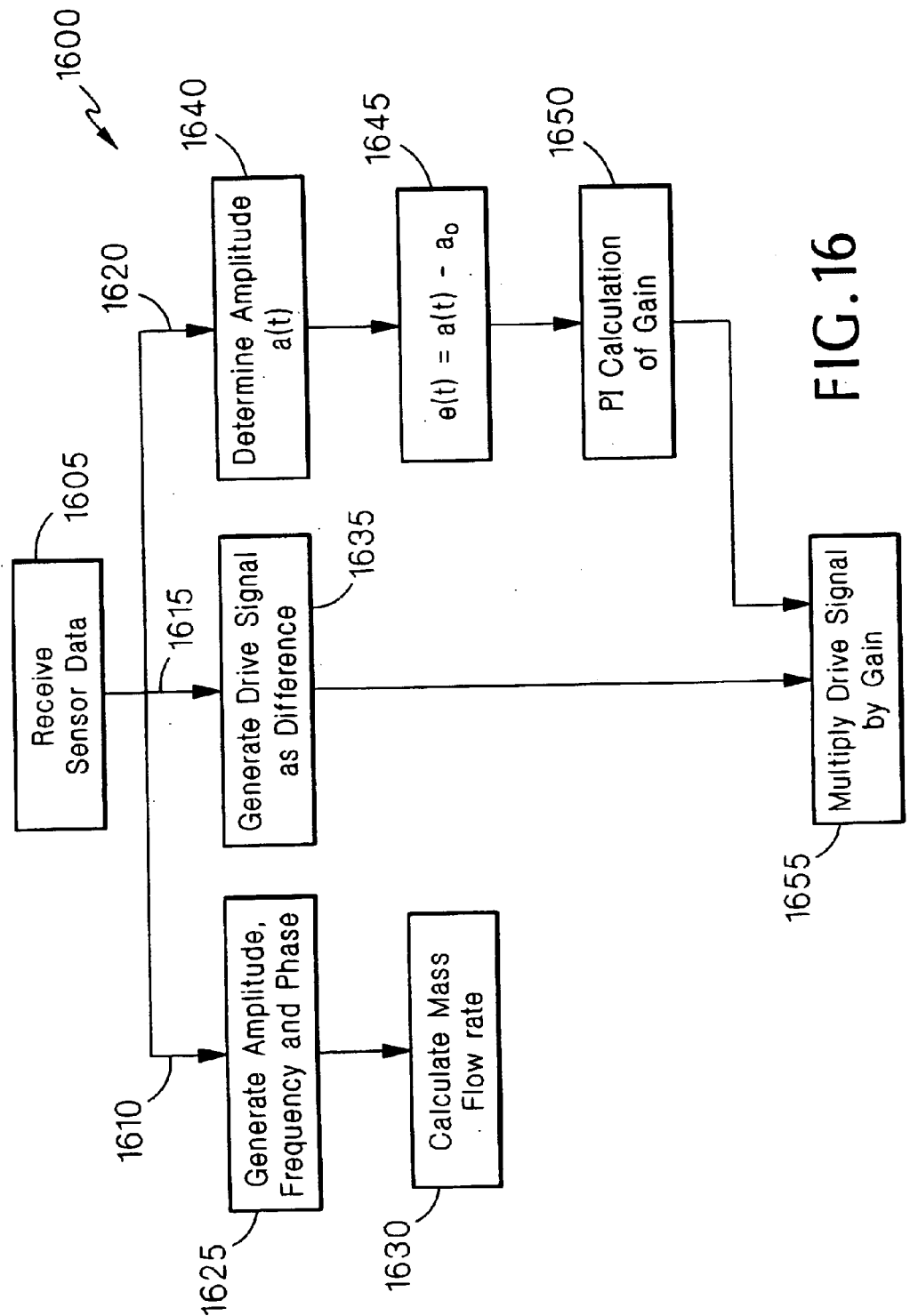
FIG. 16 is a flow chart of a procedure implemented by the meter of FIGS. 15A and 15B.

The meter 1500 operates according to the procedure 1600 illustrated in FIG. 16. Initially, the controller receives digitized data from the sensors (step 1605). Thereafter, the procedure 1600 includes three parallel branches: a measurement branch 1610, a drive signal is generation branch 1615, and a gain generation branch 1620.

In the measurement branch 1610, the digitized sensor data is used to generate measurements of amplitude, frequency, and phase, as described above (step 1625). These measurements then are used to calculate the mass flow rate (step 1630) and other process variables. In general, the controller 1505 implements the measurement branch 1610.

In the drive signal generation branch 1615, the digitized signals from the two sensors are differenced to generate the signal (step 1635) that is multiplied by the gain to produce the drive signal. As described above, this differencing operation is performed by the controller 1505. In general, the differencing operation produces a weighted difference that accounts for amplitude differences between the sensor signals.

In the gain generation branch 1620, the gain is calculated using the proportional-integral control block. As noted above, the amplitude, a(t), of motion of the conduit is determined (step 1640) and subtracted from the desired amplitude $a_o$ (step 1645) to calculate the error e(t). Though illustrated as a separate step, generation of the amplitude, a(t), may correspond to generation of the amplitude in the measurement generation step 1625. Finally, the PI control block uses the error e(t) to calculate the gain (step 1650).

The calculated gain is multiplied by the difference signal to generate the drive signal supplied to the drivers (step 1655). As described above, this multiplication operation is performed by the multiplying D/A converter or may be performed by the controller.

2. PI Control Block

The objective of the PI control block is to sustain in the conduit pure sinusoidal oscillations having an amplitude $a_0$. The behavior of the conduit may be modeled as a simple mass-spring system that may be expressed as:

$\ddot{x}+2\zeta\omega_n\dot{x}+\omega_n^2x=0,$ where x is a function of time and the displacement of the mass from equilibrium, $\omega_n$ is the natural frequency, and $\zeta$ is a damping factor, which is assumed to be small (e.g., 0.001). The solution to this force equation as a function of an output y(t) and an input i(t) is analogous to an electrical network in which the transfer function between a supplied current, i(s), and a sensed output voltage, y(s), is:

$$\frac{y(s)}{i(s)} = \frac{ks}{s^2+2\zeta\omega_ns+\omega_n^2}.$$

To achieve the desired oscillation in the conduit, a positive-feedback loop having the gain $K_0(t)$ is automatically adjusted by a 'slow' outer loop to give:

$\ddot{x}+(2\zeta\omega_n-kK_0(t))\dot{x}+\omega_n^2x=0.$

The system is assumed to have a "two-time-scales" property, which means that variations in $K_0(t)$ are slow enough that solutions to the equation for x provided above can be obtained by assuming constant damping.

A two-term PI control block that gives zero steady-state error may be expressed as:

$$K_0(t) = K_p e(t) + K_i \int_0^t e(t)\,dt,$$

where the error, e(t) (i.e., $a_0 - a(t)$), is the input to the PI control block, and $K_p$ and $K_i$ are constants. In one implementation, with $a_0 = 10$, controller constants of $K_p = 0.02$ and $K_i = 0.0005$ provide a response in which oscillations build up quickly. However, this PI control block is nonlinear, which may result in design and operational difficulties.

A linear model of the behavior of the oscillation amplitude may be derived by assuming that x(t) equals $Ae^{j\omega t}$, which results in:

$$\dot{x} = \dot{A}e^{j\omega t} + j\omega e^{j\omega t}, \text{ and}$$

$$\ddot{x} = [\ddot{A} - \omega^2 A]e^{j\omega t} + 2j\omega \dot{A}e^{j\omega t}.$$

Substituting these expressions into the expression for oscillation of the loop, and separating into real and imaginary terms, gives:

$$j\omega\{2\dot{A} + (2\zeta\omega_n - kK_0)A\} = 0, \text{ and}$$

$$\ddot{A} + (2\zeta\omega_n - kK_0)\dot{A} + (\omega_n^2 - \omega^2)A = 0.$$

A(t) also may be expressed as:

$$\frac{\dot{A}}{A} = -\zeta\omega_n + \frac{kK_0}{2}t.$$

A solution of this equation is:

$$\log A(t) = \left(-\zeta\omega_n + \frac{kK_0}{2}\right)t.$$

Figure 17:
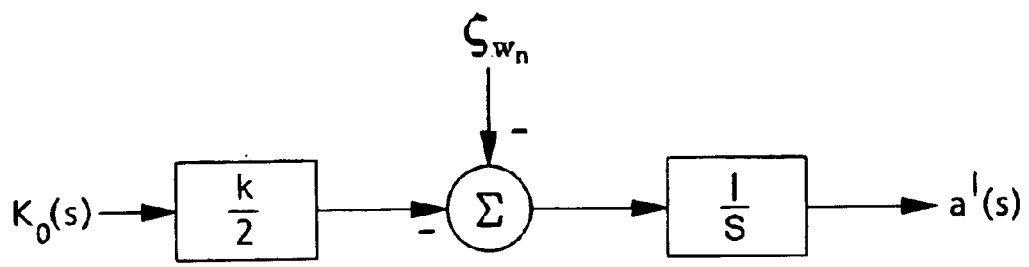
FIG. 17 illustrates log-amplitude control of a transfer function.

Transforming variables by defining a(t) as being equal to log A(t), the equation for A(t) can be written as:

$$\frac{da}{dt} = -\zeta\omega_n + \frac{kK_0(t)}{2},$$

where $K_o$ is now explicitly dependent on time. Taking Laplace transforms results in:

$$a(s) = \frac{-\zeta\omega_n - kK_0(s)/2}{s},$$

which can be interpreted in terms of transfer-functions as in FIG. 17. This figure is of particular significance for the design of controllers, as it is linear for all $K_o$ and a, with the only assumption being the two-time-scales property. The performance of the closed-loop is robust with respect to this assumption so that fast responses which are attainable in practice can be readily designed.

From FIG. 17, the term $\zeta\omega_n$ is a "load disturbance" that needs to be eliminated by the controller (i.e., $kK_o/2$ must equal $\zeta\omega_n$, for a(t) to be constant). For zero steady-state error this implies that the outer-loop controller must have an integrator (or very large gain). As such, an appropriate PI controller, C(s), may be assumed to be $K_p(1+1/sT_i)$, where $T_i$ is a constant. The proportional term is required for stability. The term $\zeta\omega_n$, however, does not affect stability or controller design, which is based instead on the open-loop transfer function:

$$C(s)G(s) = \frac{a(s)}{e(s)} = \frac{kK_p(1+sT_i)}{2s^2T_i} = \frac{kK_p/2(s+1/T_i)}{s^2}.$$

Figure 18:
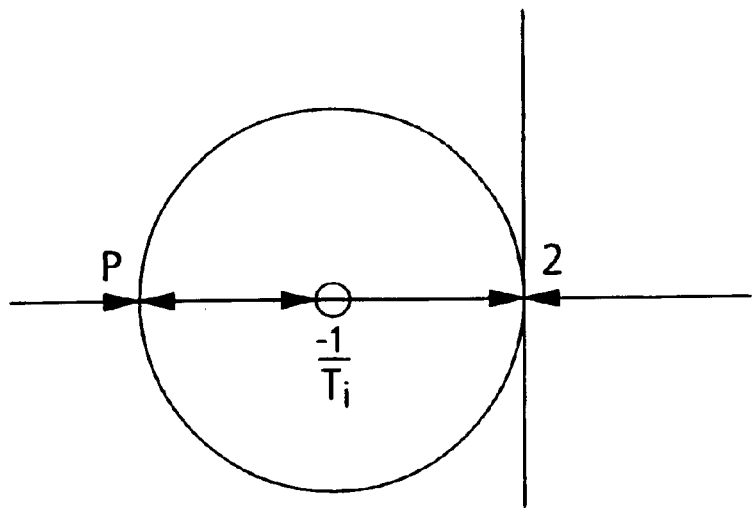
FIG. 18 is a root locus diagram.
Figure 19A:
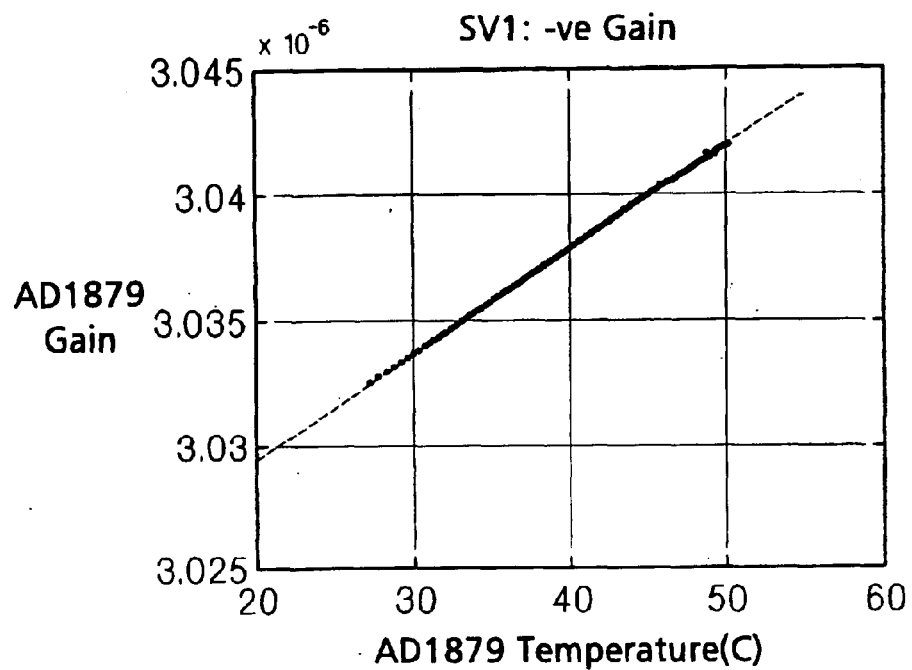
FIGS. 19A–19D are graphs of analog-to-digital converter performance relative to temperature.
Figure 19B:
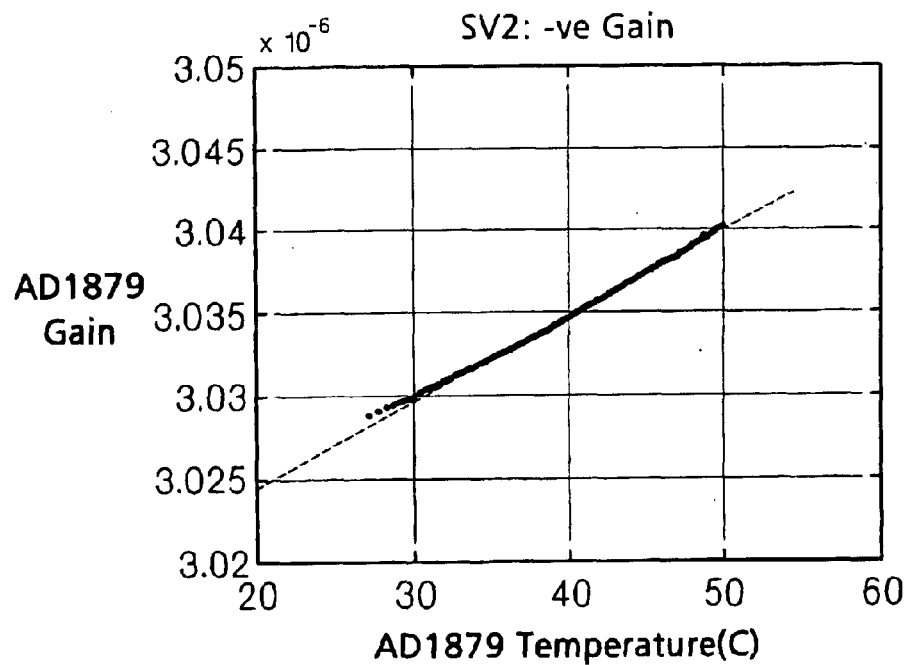
Figure 19C:
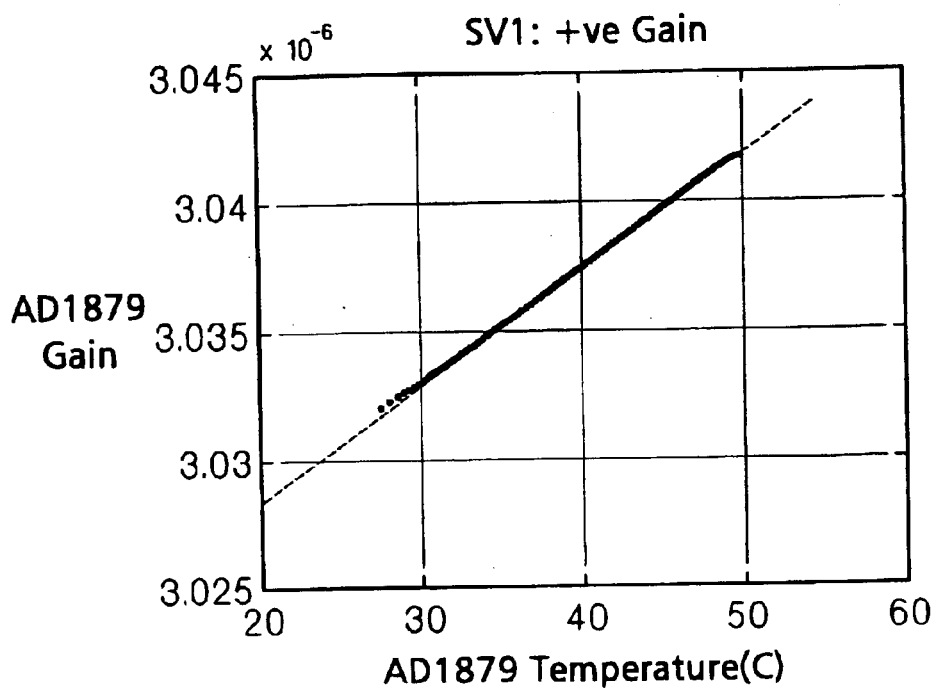
Figure 19D:
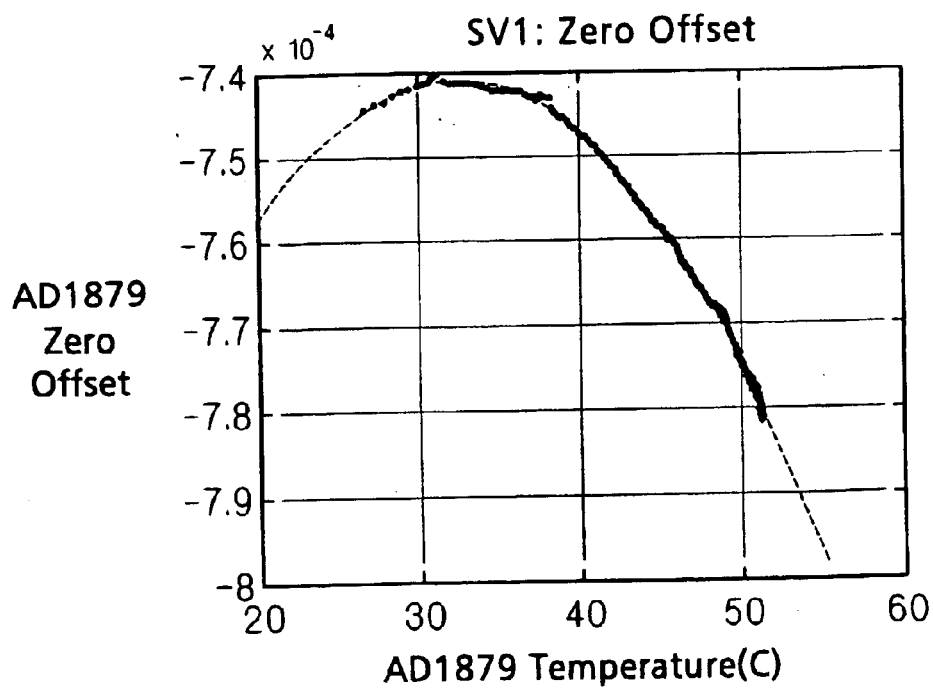

The root locus for varying $K_p$ is shown in FIG. 18. For small $K_p$, there are slow underdamped roots. As $K_p$ increases, the roots become real at the point P for which the controller gain is $K_p = 8/(kT_i)$. Note in particular that the theory does not place any restriction upon the choice of $T_i$. Hence the response can, in principle, be made critically damped and as fast as desired by appropriate choices of $K_p$ and $T_i$.

Although the poles are purely real at point P, this does not mean there is no overshoot in the closed-loop step response. This is most easily seen by inspecting the transfer function between the desired value, $a_0$, and the error e:

$$\frac{e(s)}{a_0(s)} = \frac{s^2}{s^2 + 0.5kK_p(s+1/T_i)} = \frac{s^2}{p_2(s)},$$

where $p_2$ is a second-order polynomial. With a step input, $a_o(s) = \alpha/s$, the response can be written as $\alpha p'(t)$, where p(t) is the inverse transform of $1/p_2(s)$ and equals $a_1 \exp(-\lambda_1 t) + a_2\exp(-\lambda_2 t)$. The signal p(t) increases and then decays to zero so that e(t), which is proportional to p', must change sign, implying overshoot in a(t). The set-point $a_o$ may be prefiltered to give a pseudo set-point $a_o^*$:

$$a_0^*(s) = \frac{1}{1+sT_i}a_0(s),$$

where $T_i$ is the known controller parameter. With this prefilter, real controller poles should provide overshoot-free step responses. This feature is useful as there may be physical constraints on overshoot (e.g., mechanical interference or overstressing of components).

The root locus of FIG. 18 assumes that the only dynamics are from the inner-loop's gain/log-amplitude transfer function (FIG. 16) and the outer-loop's PI controller C(s) (i.e., that the log-amplitude a=log A is measured instantaneously). However, A is the amplitude of an oscillation which might be growing or decaying and hence cannot in general be measured without taking into account the underlying sinusoid. There are several possible methods for measuring A, in addition to those discussed above. Some are more suitable for use in quasi-steady conditions. For example, a phase-locked loop in which a sinusoidal signal $s(t) = \sin(\omega_n t + \Phi_0)$ locks onto the measured waveform $y(t) = A(t) \sin(\omega_n t + \Phi_1)$ may be employed. Thus, a measure of the amplitude a=log A is given by dividing these signals (with appropriate safeguards and filters). This method is perhaps satisfactory near the steady-state but not for start-up conditions before there is a lock.

Another approach uses a peak-follower that includes a zero-crossing detector together with a peak-following algorithm implemented in the controller. Zero-crossing methods, however, can be susceptible to noise. In addition, results from a peak-follower are available only every half-cycle and thereby dictate the sample interval for controller updates.

Finally, an AM detector may be employed. Given a sine wave $y(t) = A \sin \omega_n t$, an estimate of A may be obtained from $\hat{A}_1 0.5\pi F\{abs(y)\}$, where F{ } is a suitable low-pass filter with unity DC gain. The AM detector is the simplest approach. Moreover, it does not presume that there are oscillations of any particular frequency, and hence is usable during startup conditions. It suffers from a disadvantage that there is a leakage of harmonics into the inner loop which will affect the spectrum of the resultant oscillations. In addition, the filter adds extra dynamics into the outer loop such that compromises need to be made between speed of response and spectral purity. In particular, an effect of the filter is to constrain the choice of the best $T_i$.

The Fourier series for abs(y) is known to be:

$$A \text{ abs}(\sin\omega_n t) = \frac{2A}{\pi}\left[1 + \frac{2}{3}\cos 2\omega_n t - \frac{2}{15}\cos 4\omega_n t + \frac{2}{35}\cos 6\omega_n t + \ldots\right].$$

As such, the output has to be scaled by $\pi/2$ to give the correct DC output A, and the (even) harmonic terms $a_k \cos 2k\omega_n t$ have to be filtered out. As all the filter needs to do is to pass the DC component through and reduce all other frequencies, a "brick-wall" filter with a cut-off below $2\omega_n$ is sufficient. However, the dynamics of the filter will affect the behavior of the closed-loop. A common choice of filter is in the Butterworth form. For example, the third-order low-pass filter with a design break-point frequency $\omega_b$ is:

$$F(s) = \frac{1}{1 + 2s/\omega_b + 2s^2/\omega_b^2 + s^3/\omega_b^3}.$$

At the design frequency the response is 3 dB down; at $2\omega_b$, it is −18 dB (0.12), and at $4\omega_b$ it is −36 dB (0.015) down. Higher-order Butterworth filters have a steeper roll-off, but most of their poles are complex and may affect negatively the control-loop's root locus.

G. Zero Offset Compensation

As noted above, zero offset may be introduced into a sensor voltage signal by drift in the pre-amplification circuitry and by the analog-to-digital converter. Slight differences in the pre-amplification gains for positive and negative voltages due to the use of differential circuitry may worsen the zero offset effect. The errors vary between transmitters, and with transmitter temperature and component wear.

Audio quality (i.e., relatively low cost) analog-to-digital converters may be employed for economic reasons. These devices are not designed with DC offset and amplitude stability as high priorities. FIGS. 19A–19D show how offset and positive and negative gains vary with chip operating temperature for one such converter (the AD 1879 converter). The repeatability of the illustrated trends is poor, and even allowing for temperature compensation based on the trends, residual zero offset and positive/negative gain mismatch remain.

Figure 20A:
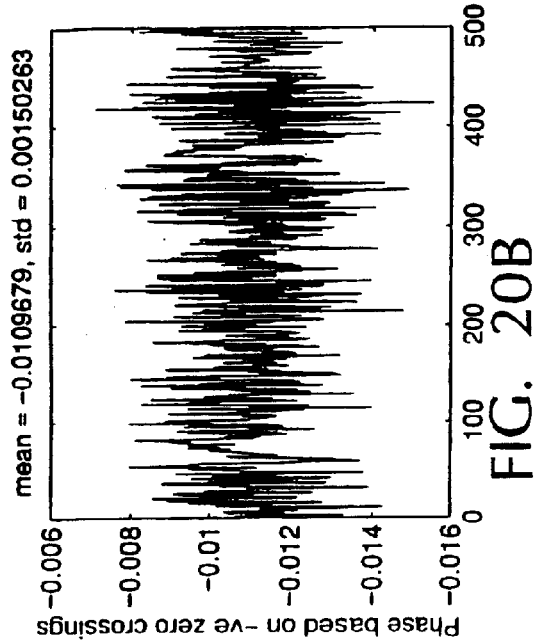
FIGS. 20A–20C are graphs of phase measurements.
Figure 20B:
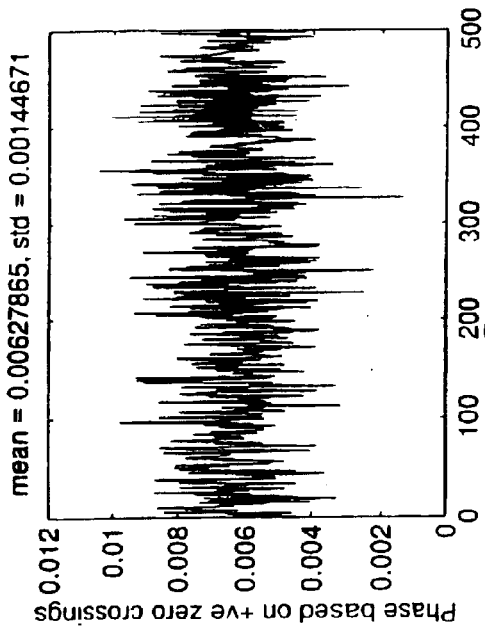
Figure 20C:
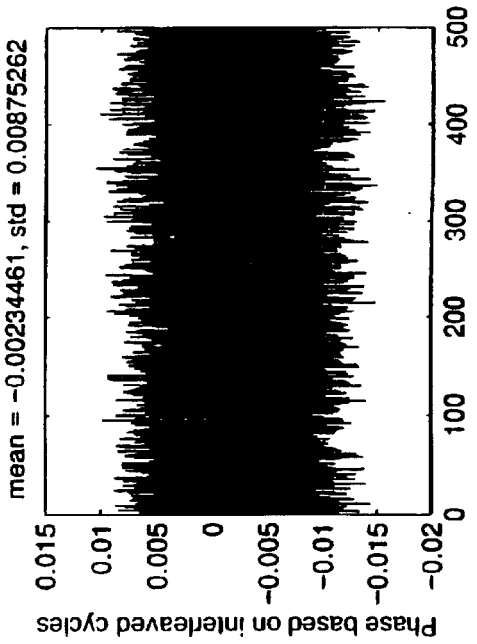

If phase is calculated using the time difference between zero crossing points on the two sensor voltages, DC offset may lead to phase errors. This effect is illustrated by FIGS. 20A–20C. Each graph shows the calculated phase offset as measured by the digital transmitter when the true phase offset is zero (i.e., at zero flow).

FIG. 20A shows phase calculated based on whole cycles starting with positive zero-crossings. The mean value is 0.00627 degrees.

FIG. 20B shows phase calculated starting with negative zero-crossings. The mean value is 0.0109 degrees.

FIG. 20C shows phase calculated every half-cycle. FIG. 20C interleaves the data from FIGS. 20A and 20B. The average phase (−0.00234) is closer to zero than in FIGS. 20A and 20B, but the standard deviation of the signal is about six times higher.

More sophisticated phase measurement techniques, such as those based on Fourier methods, are immune to DC offset. However, it is desirable to eliminate zero offset even when those techniques are used, since data is processed in whole-cycle packets delineated by zero crossing points. This allows simpler analysis of the effects of, for example, amplitude modulation on apparent phase and frequency. In addition, gain mismatch between positive and negative voltages will introduce errors into any measurement technique.

The zero-crossing technique of phase detection may be used to demonstrate the impact of zero offset and gain mismatch error, and their consequent removal. FIGS. 21A and 21B illustrate the long term drift in phase with zero flow. Each point represents an average over one minute of live data. FIG. 21A shows the average phase, and FIG. 21B shows the standard deviation in phase. Over several hours, the drift is significant. Thus, even if the meter were zeroed every day, which in many applications would be considered an excessive maintenance requirement, there would still be considerable phase drift.

1. Compensation Technique

A technique for dealing with voltage offset and gain mismatch uses the computational capabilities of the digital transmitter and does not require a zero flow condition. The technique uses a set of calculations each cycle which, when averaged over a reasonable period (e.g., 10,000 cycles), and excluding regions of major change (e.g., set point change, onset of aeration), converge on the desired zero offset and gain mismatch compensations.

Assuming the presence of up to three higher harmonics, the desired waveform for a sensor voltage SV(t) is of the form:

$$SV(t) = A_1 \sin(\omega t) + A_2 \sin(2\omega t) + A_3 \sin(3\omega t) + A_4 \sin(4\omega t)$$

where $A_1$ designates the amplitude of the fundamental frequency component and $A_2$–$A_4$ designate the amplitudes of the three harmonic components. However, in practice, the actual waveform is adulterated with zero offset $Z_o$ (which has a value close to zero) and mismatch between the negative and positive gains $G_n$ and $G_p$. Without any loss of generality, it can be assumed that $G_p$ equals one and that $G_n$ is given by:

$$G_n = 1 + \epsilon_G,$$

where $\epsilon_G$ represents the gain mismatch.

The technique assumes that the amplitudes $A_i$ and the frequency $\omega$ are constant. This is justified because estimates of $Z_o$ and $\epsilon_G$ are based on averages taken over many cycles (e.g., 10,000 interleaved cycles occurring in about 1 minute of operation). When implementing the technique, the controller tests for the presence of significant changes in frequency and amplitude to ensure the validity of the analysis. The presence of the higher harmonics leads to the use of Fourier techniques for extracting phase and amplitude information for specific harmonics. This entails integrating SV(t) and multiplying by a modulating sine or cosine function.

The zero offset impacts the integral limits, as well as the functional form. Because there is a zero offset, the starting point for calculation of amplitude and phase will not be at the zero phase point of the periodic waveform SV(t). For zero offset $Z_o$, the corresponding phase offset is, approximately, $$\varphi_{Z_0} = -\sin\left(\frac{Z_0}{A_1}\right)$$

For small phase, $$\varphi_{Z_0} = -\frac{Z_0}{A_1},$$

with corresponding time delay $$t_{Z_0} = \frac{\varphi_{Z_0}}{\omega}.$$

The integrals are scaled so that the limiting value (i.e., as $Z_o$ and $\omega_G$ approach zero) equals the amplitude of the relevant harmonic. The first two integrals of interest are:

$$I_{1Ps} = \frac{2\omega}{\pi}\int_{t_{Z_0}}^{\frac{\pi}{\omega}+t_{Z_0}} (SV(t) + Z_0) \cdot \sin[\omega(t - t_{Z_0})]\, dt,\ \text{and}$$

$$I_{1Ns} = \frac{2\omega}{\pi}(1 + \varepsilon_G)\int_{\frac{\pi}{\omega}t_{Z_0}}^{2\frac{\pi}{\omega}+t_{Z_0}} (SV(t) + Z_0) \cdot \sin[\omega(t - t_{Z_0})]\, dt.$$

These integrals represent what in practice is calculated during a normal Fourier analysis of the sensor voltage data. The subscript 1 indicates the first harmonic, N and P indicate, respectively, the negative or positive half cycle, and s and c indicate, respectively, whether a sine or a cosine modulating function has been used.

Strictly speaking, the mid-zero crossing point, and hence the corresponding integral limits, should be given by $\pi/\omega - t_{Z_o}$, rather than $\pi/\omega + t_{Z_o}$. However, the use of the exact mid-point rather than the exact zero crossing point leads to an easier analysis, and better numerical behavior (due principally to errors in the location of the zero crossing point). The only error introduced by using the exact mid-point is that a small section of each of the above integrals is multiplied by the wrong gain (1 instead of $1+\epsilon_G$ and vice versa). However, these errors are of order $Z_o^2 \epsilon_G$ and are considered negligible.

Using computer algebra and assuming small $Z_o$ and $\epsilon_G$, first order estimates for the integrals may be derived as:

$$I_{1Ps\_est} = A_1 + \frac{4}{\pi}Z_0\left[1 + \frac{2}{3}\frac{A_2}{A_1} + \frac{4}{15}\frac{A_4}{A_1}\right],\ \text{and}$$

$$I_{1Ns\_est} = (1 + \varepsilon_G)\left[A_1 - \frac{4}{\pi}Z_0\left[1 + \frac{2}{3}\frac{A_2}{A_1} + \frac{4}{15}\frac{A_4}{A_1}\right]\right].$$

Useful related functions including the sum, difference, and ratio of the integrals and their estimates may be determined. The sum of the integrals may be expressed as:

$$\text{Sum}_{1s} = (I_{1Ps} + I_{1Ns}),$$

while the sum of the estimates equals:

$$\text{Sum}_{1s\_est} = A_1(2 + \varepsilon_G) - \frac{4}{\pi}Z_0\varepsilon_G\left[1 + \frac{2}{3}\frac{A_2}{A_1} + \frac{4}{15}\frac{A_4}{A_1}\right].$$

Similarly, the difference of the integrals may be expressed as:

$$\text{Diff}_{1s} = I_{1Ps} - I_{1Ns},$$

while the difference of the estimates is:

$$\text{Diff}_{1s\_est} = A_1\varepsilon_G + \frac{4}{\pi}Z_0(2 + \varepsilon_G)\left[1 + \frac{2}{3}\frac{A_2}{A_1} + \frac{4}{15}\frac{A_4}{A_1}\right].$$

Finally, the ratio of the integrals is:

$$\text{Ratio}_{1s} = \frac{I_{1Ps}}{I_{1Ns}},$$

while the ratio of the estimates is:

$$\text{Ratio}_{1s\_est} = \frac{1}{1 + \varepsilon_G}\left[1 + Z_0\left[\frac{8}{15}\frac{15A_1 + 10A_2 + 4A_4}{\pi A_1^2}\right]\right].$$

Corresponding cosine integrals are defined as:

$$I_{1Pc} = \frac{2\omega}{\pi}\int_{t_{Z_0}}^{\frac{\pi}{\omega}+t_{Z_0}}(SV(t) + Z_0)\cos[\omega(t - t_{Z_0})]\, dt,\ \text{and}$$

$$I_{1Nc} = \frac{2\omega}{\pi}(1 + \varepsilon_G)\int_{\frac{\pi}{\omega}t_{Z_0}}^{\frac{2\pi}{\omega}+t_{Z_0}}(SV(t) + Z_0)\cos[\omega(t - t_{Z_0})]\, dt,$$

with estimates:

$$I_{1Pc\_est} = -Z_0 + \frac{40A_2 + 16A_4}{15\pi},\ \text{and}$$

$$I_{1Nc\_est} = (1 + \varepsilon_G)\left[Z_0 + \frac{40A_2 + 16A_4}{15\pi}\right],$$

and sums:

$$\text{Sum}_{1C} = I_{1Pc} + I_{1Nc},\ \text{and}$$

$$\text{Sum}_{1C\_est} = \varepsilon_G\left[Z_0 + \frac{40A_2 + 16A_4}{15\pi}\right].$$

Second harmonic integrals are:

$$I_{2Ps} = \frac{2\omega}{\pi}\int_{\frac{\pi}{\omega}t_{Z_0}}^{\frac{\pi}{\omega}+t_{Z_0}}(SV(t) + Z_0)\sin[2\omega(t - t_{Z_0})]\, dt,\ \text{and}$$

$$I_{2Ns} = \frac{2\omega}{\pi}(1 + \varepsilon_G)\int_{\frac{\pi}{\omega}t_{Z_0}}^{\frac{2\pi}{\omega}+t_{Z_0}}(SV(t) + Z_0)\sin[2\omega(t - t_{Z_0})]\, dt,$$

with estimates:

$$I_{2Ps\_est} = A_2 + \frac{8}{15\pi}Z_0\left[-5 + 9\frac{A_3}{A_1}\right],\ \text{and}$$

$$I_{2Ps\_est} = (1 + \varepsilon_G)\left[A_2 - \frac{8}{15\pi}Z_0\left[-5 + 9\frac{A_3}{A_1}\right]\right],$$

and sums:

$$\text{Sum}_{2s} = I_{2Ps} + I_{2Ns},\ \text{and}$$

$$\text{Sum}_{2Ps\_est} = A_2(2 + \varepsilon_G) - \frac{8}{15\pi}\varepsilon_G Z_0\left[-5 + 9\frac{A_3}{A_1}\right].$$

The integrals can be calculated numerically every cycle. As discussed below, the equations estimating the values of the integrals in terms of various amplitudes and the zero offset and gain values are rearranged to give estimates of the zero offset and gain terms based on the calculated integrals.

2. Example

The accuracy of the estimation equations may be illustrated with an example. For each basic integral, three values are provided: the "true" value of the integral (calculated within Mathcad using Romberg integration), the value using the estimation equation, and the value calculated by the digital transmitter operating in simulation mode, using Simpson's method with end correction.

Thus, for example, the value for $I_{1Ps}$ calculated according to:

$$I_{1Ps} = \frac{2\omega}{\pi} \int_{t_{z_0}}^{\frac{\pi}{\omega}+t_{z_0}} (SV(t)+Z_0)\sin[\omega(t-t_{z_0})]dt$$

is 0.101353, while the estimated value ($I_{1Ps\_est}$) calculated as:

$$I_{1Ps\_est} = A_1 + \frac{4}{\pi}Z_0\left[1 + \frac{2}{3}\frac{A_2}{A_1} + \frac{4}{15}\frac{A_4}{A_1}\right]$$

is 0.101358. The value calculated using the digital transmitter in simulation mode is 0.101340. These calculations use the parameter values illustrated in Table C.

TABLE C

| Parameter | Value | Comment |
| --- | --- | --- |
| ω | 160π | This corresponds to frequency = 80 Hz, a typical value. |
| $A_1$ | 0.1 | This more typically is 0.3, but it could be smaller with aeration. |
| $A_2$ | 0.01 | This more typically is 0.005, but it could be larger with aeration. |
| $A_3$ and $A_4$ | 0.0 | The digital Coriolis simulation mode only offers two harmonics, so these higher harmonics are ignored. However, they are small (<0.002). |
| $Z_0$ | 0.001 | Experience suggests that this is a large value for zero offset. |
| $\epsilon_G$ | 0.001 | Experience suggests this is a large value for gain mismatch. |

The exact, estimate and simulation results from using these parameter values are illustrated in Table D.

TABLE D

| Integral | 'Exact' Value | Estimate | Digital Coriolis Simulation |
| --- | --- | --- | --- |
| $I_{1Ps}$ | 0.101353 | 0.101358 | 0.101340 |
| $I_{1Ns}$ | 0.098735 | 0.098740 | 0.098751 |
| $I_{1Pc}$ | 0.007487 | 0.007488 | 0.007500 |
| $I_{1Nc}$ | 0.009496 | −0.009498 | −0.009531 |
| $I_{2Ps}$ | 0.009149 | 0.009151 | 0.009118 |
| $I_{2Ns}$ | 0.010857 | 0.010859 | 0.010885 |

Thus, at least for the particular values selected, the estimates given by the first order equations are extremely accurate. As $Z_o$ and $\epsilon_G$ approach zero, the errors in both the estimate and the simulation approach zero.

3. Implementation

The first order estimates for the integrals define a series of non-linear equations in terms of the amplitudes of the harmonics, the zero offset, and the gain mismatch. As the equations are non-linear, an exact solution is not readily available. However, an approximation followed by corrective iterations provides reasonable convergence with limited computational overhead.

Conduit-specific ratios may be assumed for $A_1$–$A_4$. As such, no attempt is made to calculate all of the amplitudes $A_1$–$A_4$. Instead, only $A_1$ and $A_2$ are estimated using the integral equations defined above. Based on experience of the relative amplitudes, $A_3$ may be approximated as $A_2/2$, and $A_4$ may be approximated as $A_2/10$.

Figure 22:
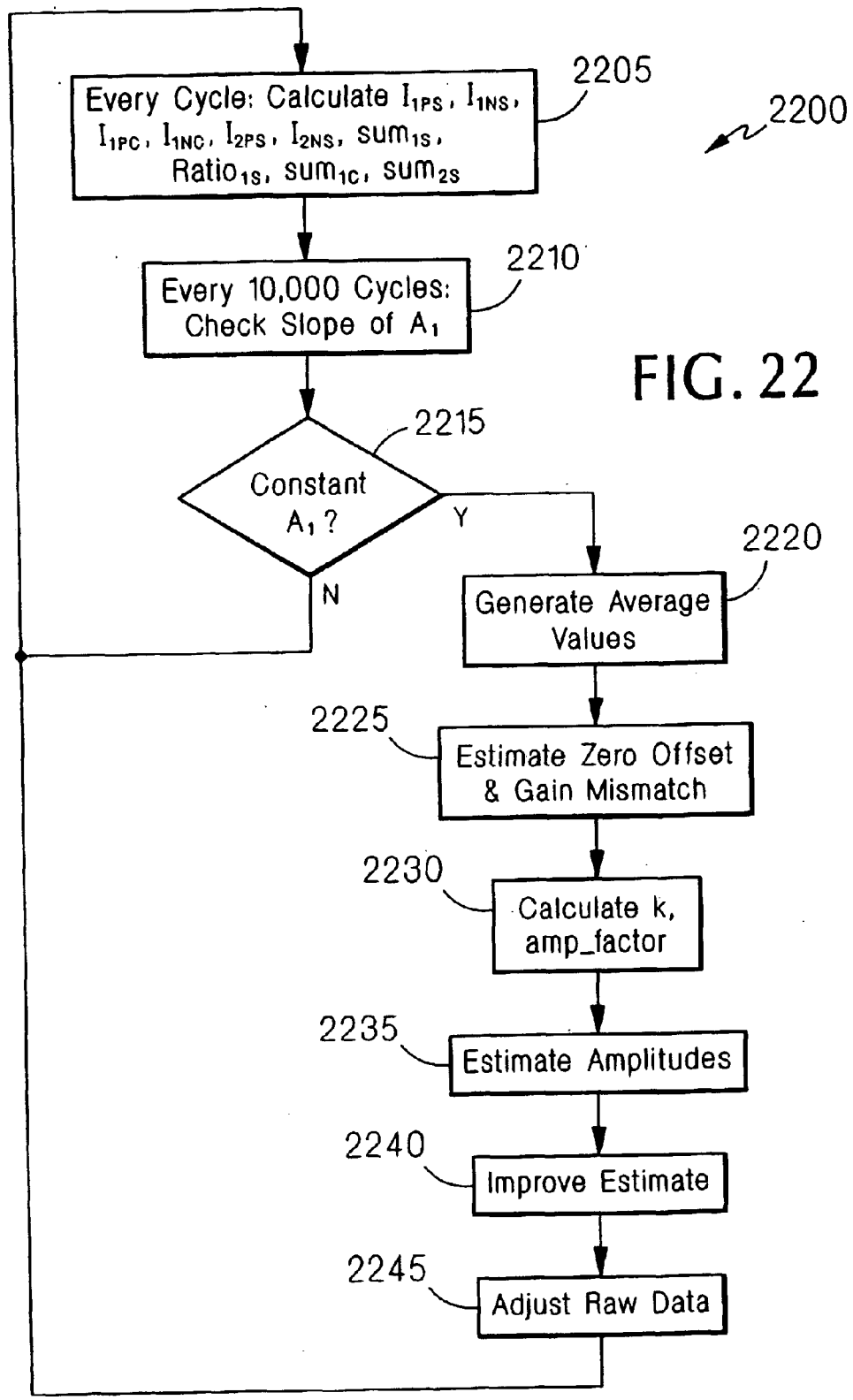
FIG. 22 is a flow chart of a zero offset compensation procedure.

The zero offset compensation technique may be implemented according to the procedure 2200 illustrated in FIG. 22. During each cycle, the controller calculates the integrals $I_{1Ps}$, $I_{1Ns}$, $I_{1Pc}$, $I_{1Nc}$, $I_{2Ps}$, $I_{2Ns}$ and related functions $sum_{1s}$, $ration_{1s}$, $sum_{1c}$ and $sum_{2s}$ (step 2205). This requires minimal additional calculation beyond the conventional Fourier calculations used to determine frequency, amplitude and phase.

Every 10,000 cycles, the controller checks on the slope of the sensor voltage amplitude $A_1$, using a conventional rate-of-change estimation technique (step 2210). If the amplitude is constant (step 2215), then the controller proceeds with calculations for zero offset and gain mismatch. This check may be extended to test for frequency stability.

To perform the calculations, the controller generates average values for the functions (e.g., $sum_{1s}$,) over the last 10,000 cycles. The controller then makes a first estimation of zero offset and gain mismatch (step 2225):

$Z_0 = -Sum_{1c}/2$, and $\epsilon_G = 1/Ratio_{1s} - 1$

Using these values, the controller calculates an inverse gain factor (k) and amplitude factor (amp_factor) (step 2230):

$k = 1.0/(1.0+0.5*\epsilon_G)$, and $amp\_factor = 1+50/75*Sum_{2s}/Sum_{1s}$

The controller uses the inverse gain factor and amplitude factor to make a first estimation of the amplitudes (step 2235):

$A_1 = k*[Sum_{1s}/2 + 2/\pi*Z_o*\epsilon_G*amp\_factor]$, and $A_2 = k*[Sum_{2s}/2 - 4/(3*\pi)*Z_o*\epsilon_G$ The controller then improves the estimate by the following calculations, iterating as required (step 2240):

$x_1 = Z_o$, $x_2 = \epsilon_G$, $\epsilon_G = [1 + 8/\pi*x_1/A_1*amp\_factor]/Ratio_{1s} - 1.0$, $Z_o = -Sum_{1c}/2 + x_2*(x_1 + 2.773/\pi*A_2)/2$, $A_1 = k*[Sum_{1s}/2 + 2/\pi*x_1*x_2*amp\_factor]$, $A_2 = k*[Sum_{2s}/2 - 4/(15*\pi)*x_1*x_2*(5-4.5*A_2)]$.

The controller uses standard techniques to test for convergence of the values of $Z_o$ and $\epsilon_G$. In practice the corrections are small after the first iteration, and experience suggests that three iterations are adequate.

Finally, the controller adjusts the raw data to eliminate $Z_o$ and $\epsilon_G$ (step 2245). The controller then repeats the procedure. Once zero offset and gain mismatch have been eliminated from the raw data, the functions (i.e., $sum_{1s}$) used in generating subsequent values for $Z_o$ and $\epsilon_G$ are based on corrected data. Accordingly, these subsequent values for $Z_o$ and $\epsilon_G$ reflect residual zero offset and gain mismatch, and are summed with previously generated values to produce the actual zero offset and gain mismatch. In one approach to adjusting the raw data, the controller generates adjustment parameters (e.g., S1_off and S2_off) that are used in converting the analog signals from the sensors to digital data.

Figure 23A:
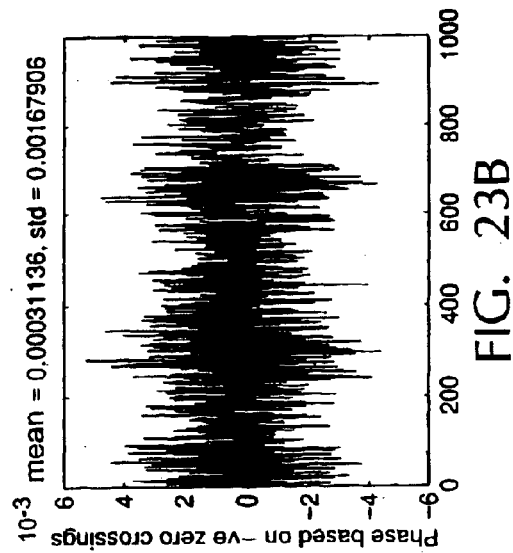
Figure 23B:
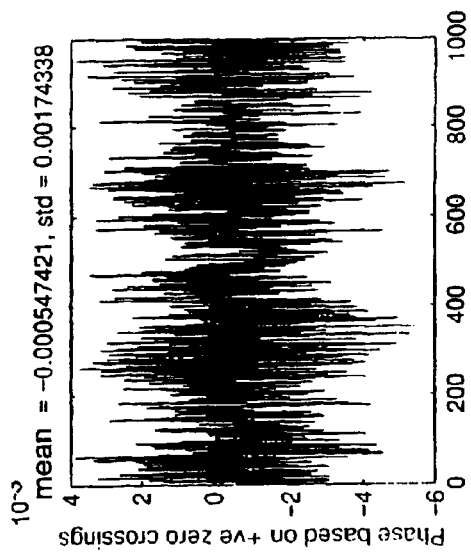
Figure 23C:
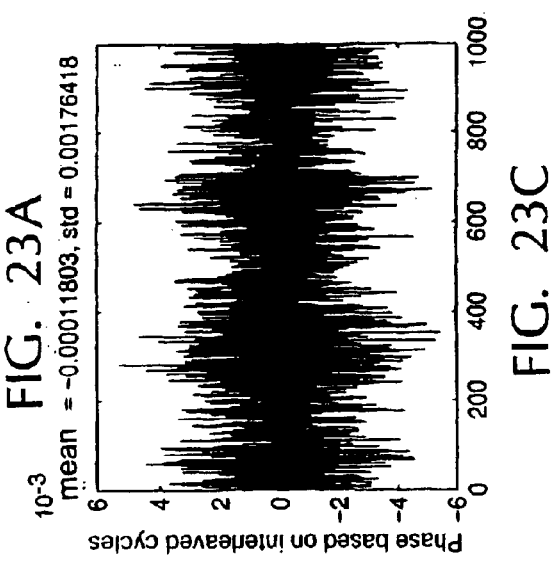

FIGS. 23A–23C, 24A and 24B show results obtained using the procedure 2200. The short-term behavior is illustrated in FIGS. 23A–23C. This shows consecutive phase estimates obtained five minutes after startup to allow time for the procedure to begin affecting the output. Phase is shown based on positive zero-crossings, negative zero-crossings, and both.

The difference between the positive and negative mean values has been reduced by a factor of 20, with a corresponding reduction in mean zero offset in the interleaved data set. The corresponding standard deviation has been reduced by a factor of approximately 6.

Longer term behavior is shown in FIGS. 24A and 24B. The initial large zero offset is rapidly corrected, and then the phase offset is kept close to zero over many hours. The average phase offset, excluding the first few values, is $6.14e^{-6}$, which strongly suggests that the procedure is successful in compensating for changes in voltage offset and gain imbalance.

Typical values for $Z_o$ and $\epsilon_G$ for the digital Coriolis meter are $Z_o=-7.923e^{-4}$ and $\epsilon_G=-1.754e^{-5}$ for signal $SV_1$, and $Z_o=-8.038e^{-4}$ and $\epsilon_G=+6.93e^{-4}$ for signal $SV_2$.

H. Dynamic Analysis

In general, conventional measurement calculations for Coriolis meters assume that the frequency and amplitude of oscillation on each side of the conduit are constant, and that the frequency on each side of the conduit is identical and equal to the so-called resonant frequency. Phases generally are not measured separately for each side of the conduit, and the phase difference between the two sides is assumed to be constant for the duration of the measurement process. Precise measurements of frequency, phase and amplitude every half-cycle using the digital meter demonstrate that these assumptions are only valid when parameter values are averaged over a time period on the order of seconds. Viewed at 100 Hz or higher frequencies, these parameters exhibit considerable variation. For example, during normal operation, the frequency and amplitude values of $SV_1$ may exhibit strong negative correlation with the corresponding $SV_2$ values. Accordingly, conventional measurement algorithms are subject to noise attributable to these dynamic variations. The noise becomes more significant as the measurement calculation rate increases. Other noise terms may be introduced by physical factors, such as flowtube dynamics, dynamic non-linearities (e.g. flowtube stiffness varying with amplitude), or the dynamic consequences of the sensor voltages providing velocity data rather than absolute position data.

The described techniques exploit the high precision of the digital meter to monitor and compensate for dynamic conduit behavior to reduce noise so as to provide more precise measurements of process variables such as mass flow and density. This is achieved by monitoring and compensating for such effects as the rates of change of frequency, phase and amplitude, flowtube dynamics, and dynamic physical non-idealities. A phase difference calculation which does not assume the same frequency on each side has already been described above. Other compensation techniques are described below.

Monitoring and compensation for dynamic effects may take place at the individual sensor level to provide corrected estimates of phase, frequency, amplitude or other parameters. Further compensation may also take place at the conduit level, where data from both sensors are combined, for example in the calculation of phase difference and average frequency. These two levels may be used together to provide comprehensive compensation.

Thus, instantaneous mass flow and density measurements by the flowmeter may be improved by modeling and accounting for dynamic effects of flowmeter operation. In general, 80% or more of phase noise in a Coriolis flowmeter may be attributed to flowtube dynamics (sometimes referred to as "ringing"), rather than to process conditions being measured. The application of a dynamic model can reduce phase noise by a factor of 4 to 10, leading to significantly improved flow measurement performance. A single model is effective for all flow rates and amplitudes of oscillation. Generally, computational requirements are negligible.

The dynamic analysis may be performed on each of the sensor signals in isolation from the other. This avoids, or at least delays, modeling the dynamic interaction between the two sides of the conduit, which is likely to be far more complex than the dynamics at each sensor. Also, analyzing the individual sensor signals is more likely to be successful in circumstances such as batch startup and aeration where the two sides of the conduit are subject to different forces from the process fluid.

In general, the dynamic analysis considers the impact of time-varying amplitude, frequency and phase on the calculated values for these parameters. While the frequency and amplitude are easily defined for the individual sensor voltages, phase is conventionally defined in terms of the difference between the sensor voltages. However, when a Fourier analysis is used, phase for the individual sensor may be defined in terms of the difference between the midpoint of the cycle and the average 180° phase point.

Three types of dynamic effects are measurement error and the so-called "feedback" and "velocity" effects. Measurement error results because the algorithms for calculating amplitude and phase assume that frequency, amplitude, and phase are constant over the time interval of interest. Performance of the measurement algorithms may be improved by correcting for variations in these parameters.

The feedback effect results from supplying energy to the conduit to make up for energy loss from the conduit so as to maintain a constant amplitude of oscillation. The need to add energy to the conduit is only recognized after the amplitude of oscillation begins to deviate from a desired setpoint. As a result, the damping term in the equation of motion for the oscillating conduit is not zero, and, instead, constantly dithers around zero. Although the natural frequency of the conduit does not change, it is obscured by shifts in the zero-crossings (i.e., phase variations) associated with these small changes in amplitude.

The velocity effect results because the sensor voltages observe conduit velocity, but are analyzed as being representative of conduit position. A consequence of this is that the rate of change of amplitude has an impact on the apparent frequency and phase, even if the true values of these parameters are constant.

1. Sensor-Level Compensation for Amplitude Modulation

Figure 25:
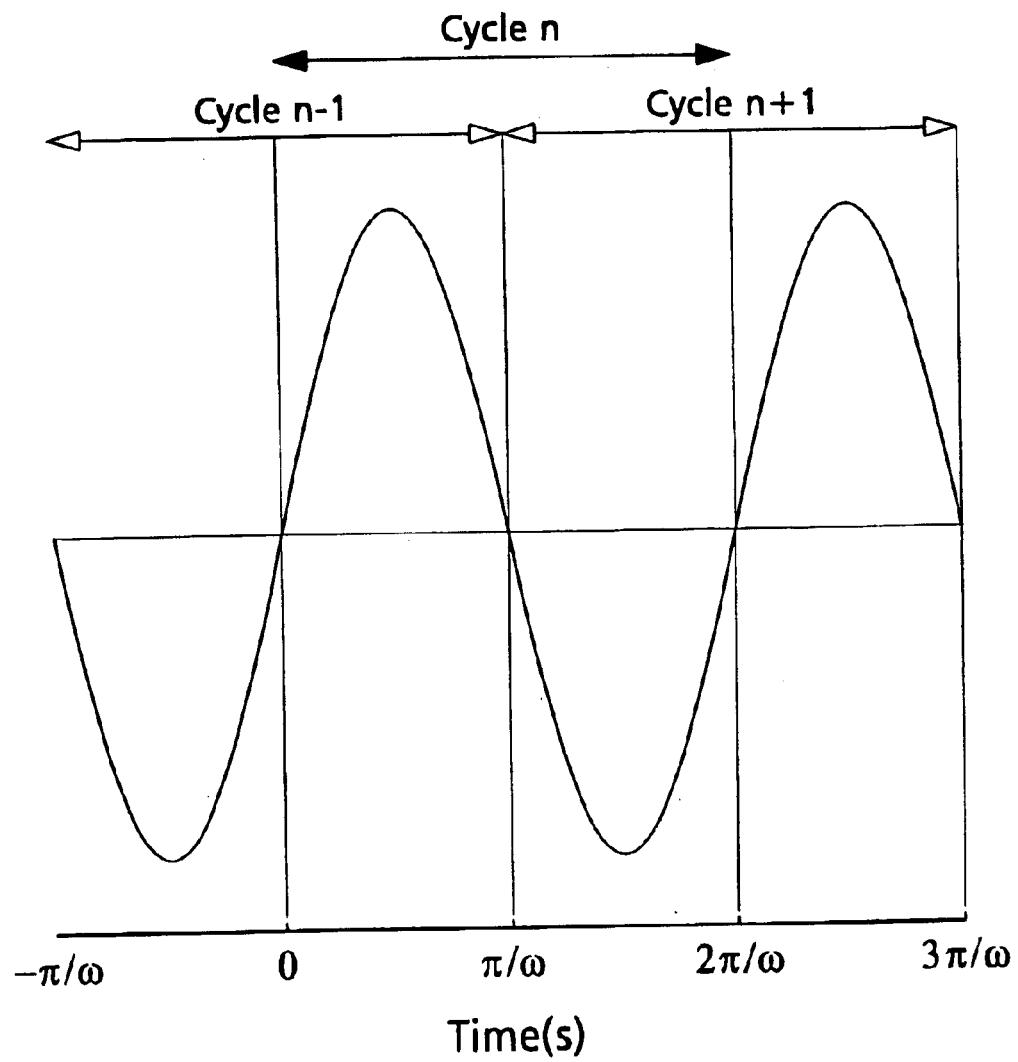
FIG. 25 is a graph of sensor voltage.

One approach to correcting for dynamic effects monitors the amplitudes of the sensor signals and makes adjustments based on variations in the amplitudes. For purposes of analyzing dynamic effects, it is assumed that estimates of phase, frequency and amplitude may be determined for each sensor voltage during each cycle. As shown in FIG. 25, calculations are based on complete but overlapping cycles.

Each cycle starts at a zero crossing point, halfway through the previous cycle. Positive cycles begin with positive voltages immediately after the initial zero-crossing, while negative cycles begin with negative voltages. Thus cycle n is positive, while cycles n−1 and n+1 are negative. It is assumed that zero offset correction has been performed so that zero offset is negligible. It also is assumed that higher harmonics may be present.

Linear variation in amplitude, frequency, and phase are assumed. Under this assumption, the average value of each parameter during a cycle equals the instantaneous value of the parameter at the mid-point of the cycle. Since the cycles overlap by 180 degrees, the average value for a cycle equals the starting value for the next cycle.

For example, cycle n is from time 0 to $2\pi/\omega$. The average values of amplitude, frequency and phase equal the instantaneous values at the mid-point, $\pi/\omega$, which is also the starting point for cycle n+1, which is from time $\pi/\omega$ to $3\pi/\omega$. Of course, these timings are approximate, since $\omega$ also varies with time.

a. Dynamic Effect Compensation Procedure

Figure 26:
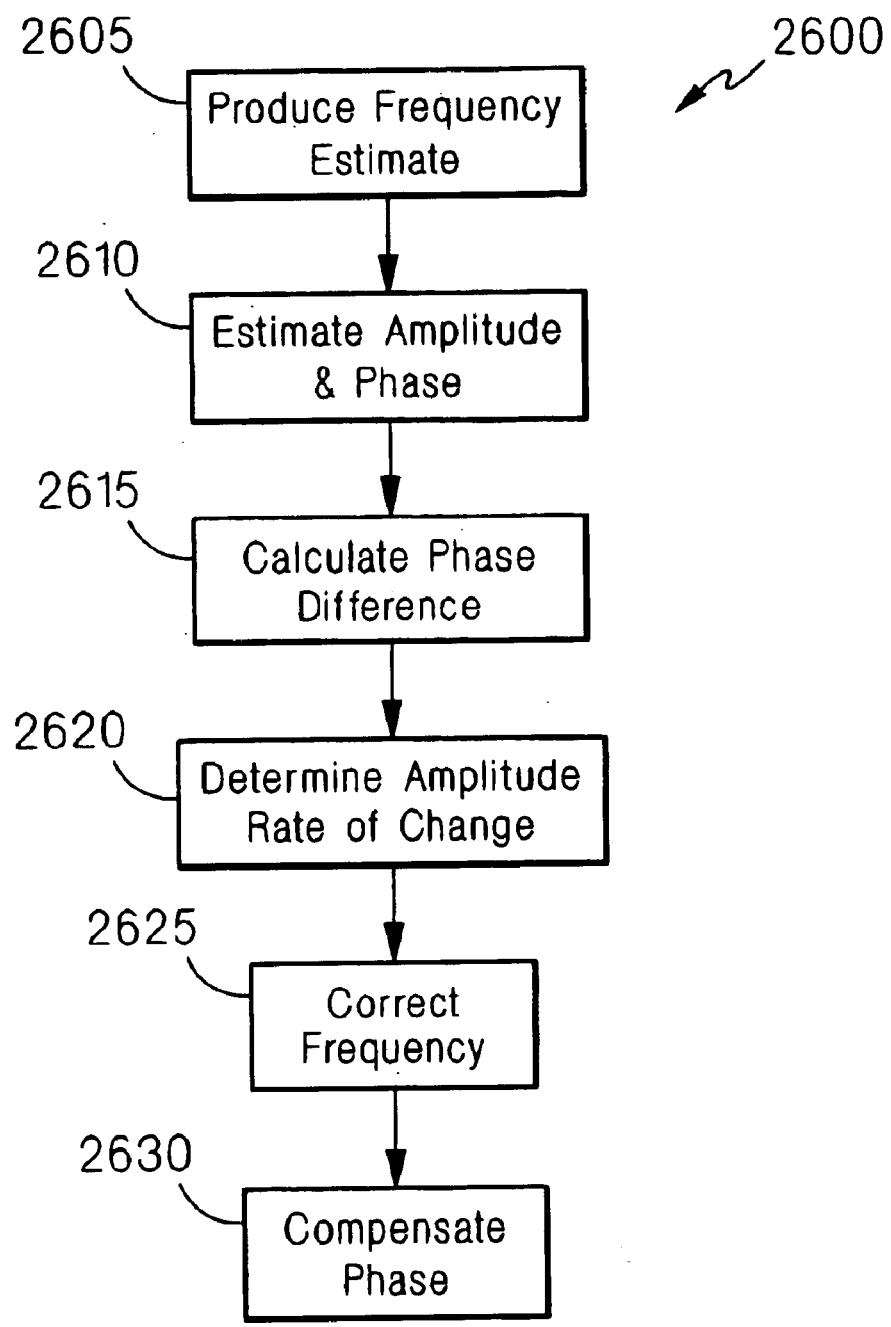
FIG. 26 is a flow chart of a procedure for compensating for dynamic effects.

The controller accounts for dynamic effects according to the procedure 2600 illustrated in FIG. 26. First, the controller produces a frequency estimate (step 2605) by using the zero crossings to measure the time between the start and end of the cycle, as described above. Assuming that frequency varies linearly, this estimate equals the time-averaged frequency over the period.

The controller then uses the estimated frequency to generate a first estimate of amplitude and phase using the Fourier method described above (step 2610). As noted above, this method eliminates the effects of higher harmonics.

Phase is interpreted in the context of a single waveform as being the difference between the start of the cycle (i.e., the zero-crossing point) and the point of zero phase for the component of SV(t) of frequency $\omega$, expressed as a phase offset. Since the phase offset is an average over the entire waveform, it may be used as the phase offset from the midpoint of the cycle. Ideally, with no zero offset and constant amplitude of oscillation, the phase offset should be zero every cycle. In practice, however, it shows a high level of variation and provides an excellent basis for correcting mass flow to account for dynamic changes in amplitude.

The controller then calculates a phase difference (step 2615). Though a number of definitions of phase difference are possible, the analysis assumes that the average phase and frequency of each sensor signal is representative of the entire waveform. Since these frequencies are different for $SV_1$ and $SV_2$, the corresponding phases are scaled to the average frequency. In addition, the phases are shifted to the same starting point (i.e., the midpoint of the cycle on $SV_1$). After scaling, they are subtracted to provide the phase difference.

The controller next determines the rate of change of the amplitude for the cycle n (step 2620):

$$\text{roc\_amp}_n \approx \frac{amp \text{ (end of cycle)} - amp \text{ (start of cycle)}}{\text{period of cycle}}$$

$$= (amp_{n+1} - amp_{n-1})freq_n.$$

This calculation assumes that the amplitude from cycle n+1 is available when calculating the rate of change of cycle n. This is possible if the corrections are made one cycle after the raw amplitude calculations have been made. The advantage of having an accurate estimate of the rate of change, and hence good measurement correction, outweighs the delay in the provision of the corrected measurements, which, in one implementation, is on the order of 5 milliseconds. The most recently generated information is always used for control of the conduit (i.e., for generation of the drive signal).

If desired, a revised estimate of the rate of change can be calculated after amplitude correction has been applied (as described below). This results in iteration to convergence for the best values of amplitude and rate of change.

b. Frequency Compensation for Feedback and Velocity Effects

As noted above, the dynamic aspects of the feedback loop introduce time varying shifts in the phase due to the small deviations in amplitude about the set-point. This results in the measured frequency, which is based on zero-crossings, differing from the natural frequency of the conduit. If velocity sensors are used, an additional shift in phase occurs. This additional shift is also associated with changes in the positional amplitude of the conduit. A dynamic analysis can monitor and compensate for these effects. Accordingly, the controller uses the calculated rate of amplitude change to correct the frequency estimate (step 2625).

The position of an oscillating conduit in a feedback loop that is employed to maintain the amplitude of oscillation of the conduit constant may be expressed as:

$$X = A(t) \sin(\omega_0 t - \theta(t)),$$

where $\theta(t)$ is the phase delay caused by the feedback effect. The mechanical Q of the oscillating conduit is typically on the order of 1000, which implies small deviations in amplitude and phase. Under these conditions, $\theta(t)$ is given by:

$$\theta(t) \approx -\frac{\dot{A}(t)}{2\omega_0 A(t)}.$$

Since each sensor measures velocity:

$$SV(t) = \dot{X}(t) = \dot{A}(t)\sin[\omega_0 t - \theta(t)] + [\omega_0 - \dot{\theta}(t)]A(t)\cos[\omega_0 t - \theta(t)]$$

$$= \omega_0 A(t)\left[\left(1 - \frac{\dot{\theta}}{\omega_0}\right)^2 + \left(\frac{\dot{A}(t)}{\omega_0 A(t)}\right)^2\right]^{1/2} \cos(\omega_0 t - \theta(t) - \gamma(t)),$$

where Y(t) is the phase delay caused by the velocity effect:

$$\gamma(t) = \tan^{-1}\left(\frac{\dot{A}(t)}{\omega_0 A(t)\left(1 - \frac{\dot{\theta}}{\omega_0}\right)}\right).$$

Since the mechanical Q of the conduit is typically on the order of 1000, and, hence, variations in amplitude and phase are small, it is reasonable to assume:

$$\frac{\dot{\theta}}{\omega_0} << 1 \text{ and } \frac{\dot{A}(t)}{\omega_0 A(t)} << 1.$$

This means that the expression for SV(t) may be simplified to:

$$SV(t) \approx \omega_0 A(t) \cos(\omega_0 t - \theta(t) - \gamma(t)),$$

and for the same reasons, the expression for the velocity offset phase delay may be simplified to:

$$\gamma(t) \approx \frac{\dot{A}(t)}{\omega_0 A(t)}.$$

Summing the feedback and velocity effect phase delays gives the total phase delay:

$$\varphi(t) = \theta(t) + \gamma(t) \approx -\frac{\dot{A}(t)}{2\omega_0 A(t)} + \frac{\dot{A}(t)}{w_0 A(t)} = \frac{\dot{A}(t)}{2\omega_0 A(t)},$$

and the following expression for SV(t):

$$SV(t) \approx \omega_0 A(t) \cos [\omega_0 t - \phi(t)].$$

From this, the actual frequency of oscillation may be distinguished from the natural frequency of oscillation. Though the former is observed, the latter is useful for density calculations. Over any reasonable length of time, and assuming adequate amplitude control, the averages of these two frequencies are the same (because the average rate of change of amplitude must be zero). However, for improved instantaneous density measurement, it is desirable to compensate the actual frequency of oscillation for dynamic effects to obtain the natural frequency. This is particularly useful in dealing with aerated fluids for which the instantaneous density can vary rapidly with time.

The apparent frequency observed for cycle n is delineated by zero crossings occurring at the midpoints of cycles n−1 and n+1. The phase delay due to velocity change will have an impact on the apparent start and end of the cycle:

$$\begin{aligned}
\text{obs\_freq}_n &= \text{obs\_freq}_{n-1} + \frac{\text{true\_freq}_n}{2\pi}(\varphi_{n+1} - \varphi_{n-1}) \\
&= \text{obs\_freq}_{n-1} + \frac{\text{true\_freq}_{n-1}}{2\pi}\left(\frac{\dot{A}_{n+1}}{4\pi \text{true\_freq}_n A_{n+1}} - \frac{\dot{A}_{n-1}}{4\pi \text{true\_freq}_n A_{n-1}}\right) \\
&= \text{obs\_freq}_{n-1} + \frac{1}{8\pi^2}\left(\frac{\dot{A}_{n+1}}{A_{n+1}} - \frac{\dot{A}_{n-1}}{A_{n-1}}\right).
\end{aligned}$$

Based on this analysis, a correction can be applied using an integrated error term:

$$\text{error\_sum}_n = \text{error\_sum}_{n-1} - \frac{1}{8\pi^2}\left(\frac{\dot{A}_{n+1}}{A_{n+1}} - \frac{\dot{A}_{n-1}}{A_{n-1}}\right),$$

and $$\text{est\_freq}_n = \text{obs\_freq}_n - \text{error\_sum}_n,$$

where the value of error_sum at startup (i.e., the value at cycle zero) is:

$$\text{error\_sum}_0 = -\frac{1}{8\pi^2}\left(\frac{\dot{A}_0}{A_0} + \frac{\dot{A}_1}{A_1}\right).$$

Though these equations include a constant term having a value of $1/8\pi^2$, actual data has indicated that a constant term of $1/8\pi$ is more appropriate. This discrepancy may be due to unmodeled dynamics that may be resolved through further analysis.

The calculations discussed above assume that the true amplitude of oscillation, A, is available. However, in practice, only the sensor voltage SV is observed. This sensor voltage may be expressed as:

$$SV(t) \approx \omega_0 \dot{A}(t) \cos (\omega_0 t - \phi(t))$$

The amplitude, amp_SV(t), of this expression is:

$$\text{amp\_}SV(t) \approx \omega_0 \dot{A}(t).$$

The rate of change of this amplitude is:

$$\text{roc\_amp\_}SV(t) \approx \omega_0 \ddot{A}(t)$$

so that the following estimation can be used:

$$\frac{\dot{A}(t)}{A(t)} \approx \frac{\text{roc\_amp\_}SV(t)}{\text{amp\_}SV(t)}.$$

c. Application of Feedback and Velocity Effect Frequency Compensation

FIGS. 27A–32B illustrate how application of the procedure 2600 improves the estimate of the natural frequency, and hence the process density, for real data from a meter having a one inch diameter conduit. Each of the figures shows 10,000 samples, which are collected in just over 1 minute.

Figure 27A:
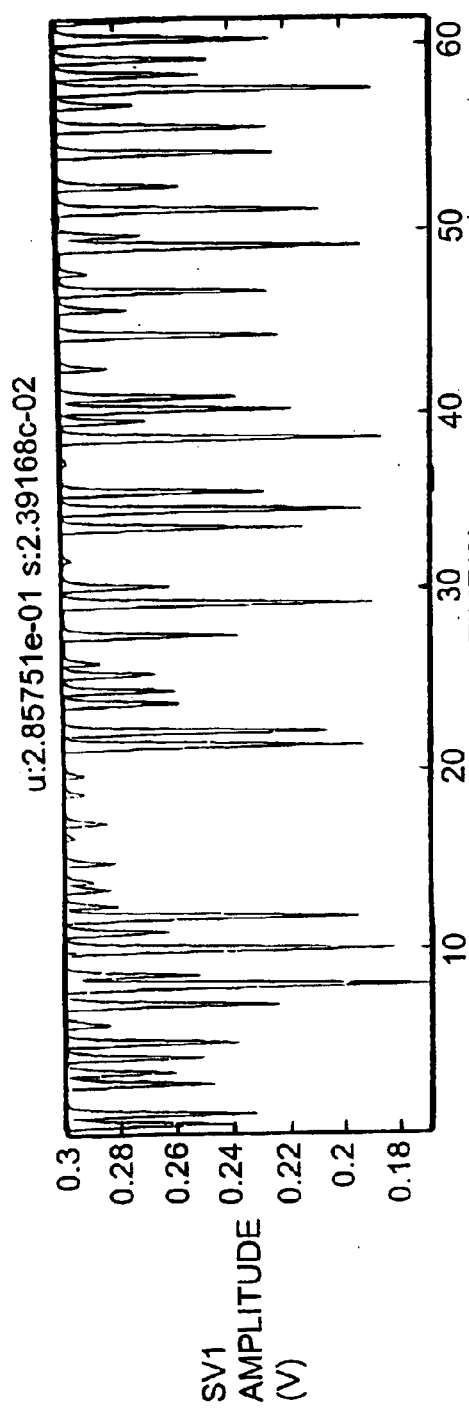
Figure 27B:
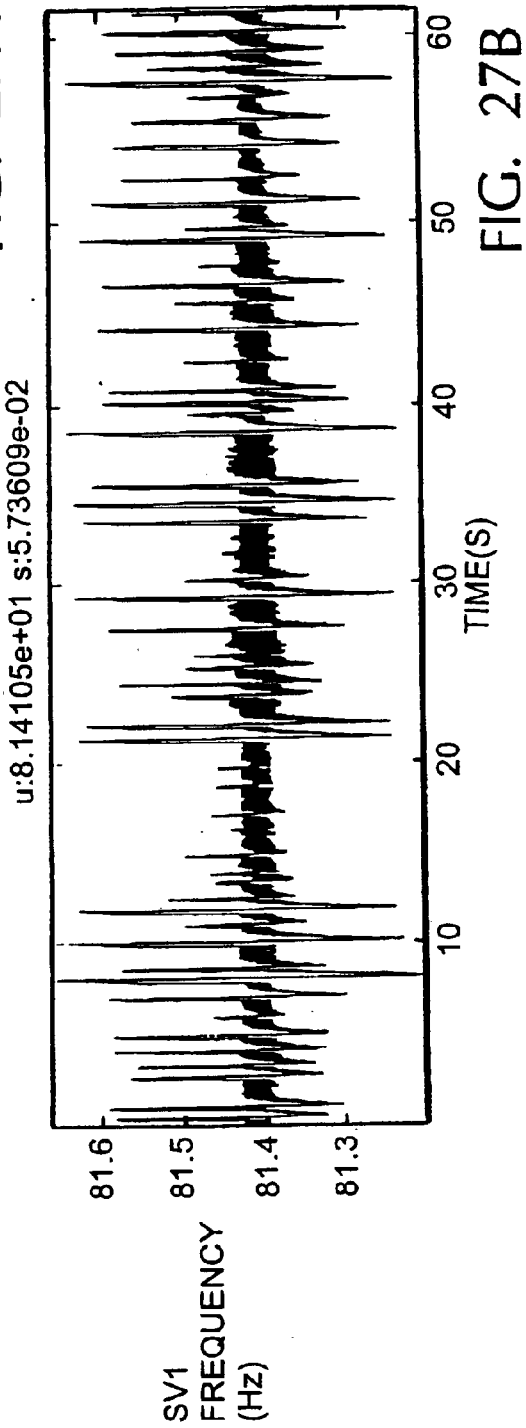

FIGS. 27A and 27B show amplitude and frequency data from $SV_1$, taken when random changes to the amplitude set-point have been applied. Since the conduit is full of water and there is no flow, the natural frequency is constant. However, the observed frequency varies considerably in response to changes in amplitude. The mean frequency value is 81.41 Hz, with a standard deviation of 0.057 Hz.

Figure 28A:
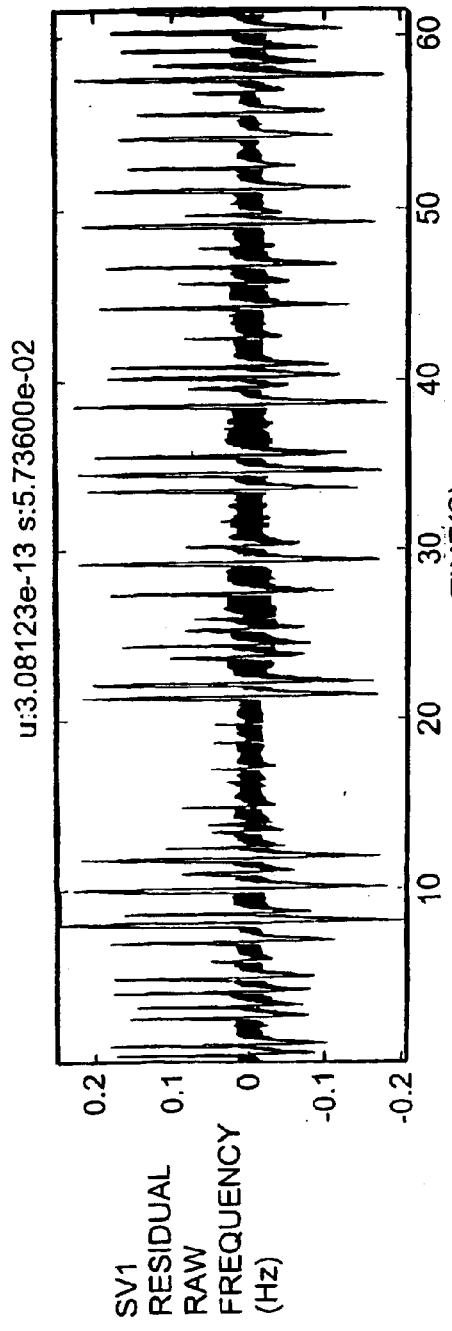
Figure 28B:
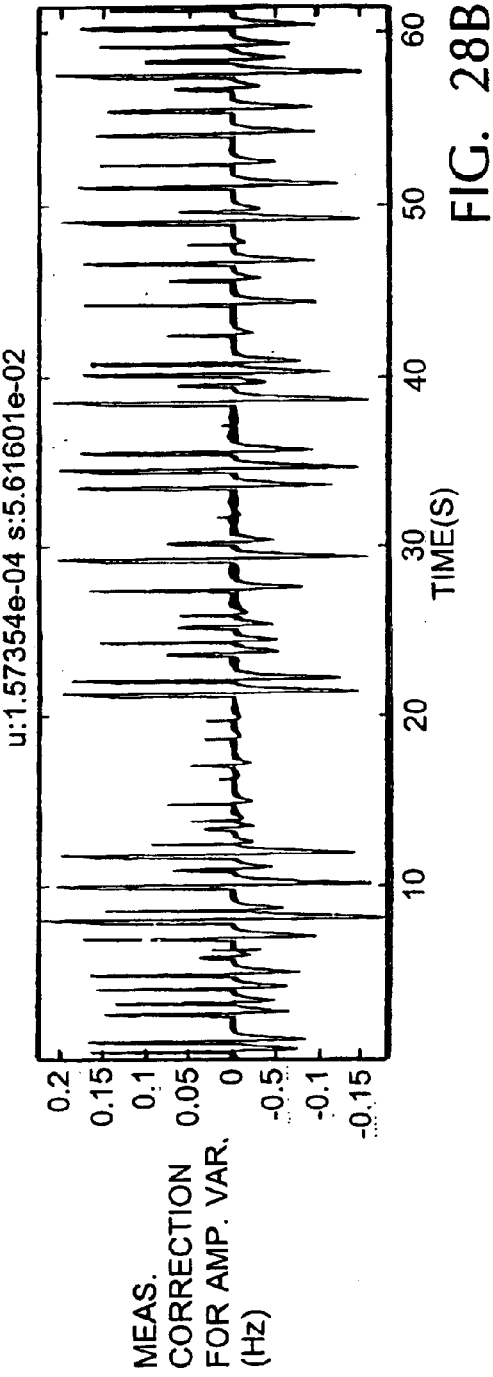

FIGS. 28A and 28B show, respectively, the variation in frequency from the mean value, and the correction term generated using the procedure 2600. The gross deviations are extremely well matched. However, there is additional variance in frequency which is not attributable to amplitude variation. Another important feature illustrated by FIG. 28B is that the average is close to zero as a result of the proper initialization of the error term, as described above.

FIGS. 29A and 92B compare the raw frequency data (FIG. 29A) with the results of applying the correction function (FIG. 29B). There has been a negligible shift in the mean frequency, while the standard deviation has been reduced by a factor of 4.4. From FIG. 29B, it is apparent that there is residual structure in the corrected frequency data. It is expected that further analysis, based on the change in phase across a cycle and its impact on the observed frequency, will yield further noise reductions.

FIGS. 30A and 30B show the corresponding effect on the average frequency, which is the mean of the instantaneous sensor voltage frequencies. Since the mean frequency is used to calculate the density of the process fluid, the noise reduction (here by a factor of 5.2) will be propagated into the calculation of density.

FIGS. 31A and 31B illustrate the raw and corrected average frequency for a 2" diameter conduit subject to a random amplitude set-point. The 2" flowtube exhibits less frequency variation that the 1", for both raw and corrected data. The noise reduction factor is 4.0.

FIGS. 32A and 32B show more typical results with real flow data for the one inch flowtube. The random setpoint algorithm has been replaced by the normal constant setpoint. As a result, there is less amplitude variation than in the previous examples, which results in a smaller noise reduction factor of 1.5.

d. Compensation of Phase Measurement for Amplitude Modulation

Referring again to FIG. 26, the controller next compensates the phase measurement to account for amplitude modulation assuming the phase calculation provided above (step 2630). The Fourier calculations of phase described above assume that the amplitude of oscillation is constant throughout the cycle of data on which the calculations take place. This section describes a correction which assumes a linear variation in amplitude over the cycle of data.

Ignoring higher harmonics, and assuming that any zero offset has been eliminated, the expression for the sensor voltage is given by:

$$SV(t) \approx A_1(1+\lambda_A t) \sin(\omega t)$$

where $\lambda_A$ is a constant corresponding to the relative change in amplitude with time. As discussed above, the integrals $I_1$ and $I_2$ may be expressed as:

$$I_1 = \frac{2\omega}{\pi} \int_0^{\frac{2\pi}{\omega}} SV(t)\sin(\omega t)\,dt, \text{ and}$$

$$I_2 = \frac{2\omega}{\pi} \int_0^{\frac{2\pi}{\omega}} SV(t)\cos(\omega t)\,dt.$$

Evaluating these integrals results in:

$$I_1 = A_1\left(1 + \frac{\pi}{\omega}\lambda_A\right), \text{ and}$$

$$I_2 = A_1 \frac{1}{2\omega}\lambda_A.$$

Substituting these expressions into the calculation for amplitude and expanding as a series in $\lambda_A$ results in:

$$\text{Amp} = A_1\left(1 + \frac{\pi}{\omega}\lambda_A + \frac{1}{8\omega^2}\lambda_A^2 + \ldots\right).$$

Assuming $\lambda_A$ is small, and ignoring all terms after the first order term, this may be simplified to:

$$\text{Amp} = A_1\left(1 + \frac{\pi}{\omega}\lambda_A\right).$$

This equals the amplitude of SV(t) at the midpoint of the cycle (t=π/ω). Accordingly, the amplitude calculation provides the required result without correction.

For the phase calculation, it is assumed that the true phase difference and frequency are constant, and that there is no voltage offset, which means that the phase value should be zero. However, as a result of amplitude modulation, the correction to be applied to the raw phase data to compensate for amplitude modulation is:

$$\text{Phase} = \tan^{-1}\left(\frac{\lambda_A}{2(\pi\lambda_A + \omega)}\right).$$

Assuming that the expression in brackets is small, the inverse tangent function can be ignored.

A more elaborate analysis considers the effects of higher harmonics. Assuming that the sensor voltage may be expressed as:

$$SV(t)=(1+\lambda_A t)[A_1 \sin(\omega t) + A_2 \sin(2\omega t) + A_3 \sin(\omega t) + A_4 \sin(4\omega t)]$$

such that all harmonic amplitudes increase at the same relative rate over the cycle, then the resulting integrals may be expressed as:

$$I_1 = A_1\left(1 + \frac{\pi}{\omega}\lambda_A\right),$$

and $$I_2 \frac{-1}{60\omega}\lambda_A(30A_1 + 80A_2 + 45A_3 + 32A_4)$$

for positive cycles, and $$I_2 \frac{-1}{60\omega}\lambda_A(30A_1 - 80A_2 + 45A_3 - 32A_4)$$

for negative cycles.

For amplitude, substituting these expressions into the calculations establishes that the amplitude calculation is only affected in the second order and higher terms, so that no correction is necessary to a first order approximation of the amplitude. For phase, the correction term becomes:

$$\frac{-1}{60}\lambda_A\left(\frac{30A_1 + 80A_2 + 45A_3 + 32A_4}{A_1(\pi\lambda_A + \omega)}\right)$$

for positive cycles, and $$\frac{-1}{60}\lambda_A\left(\frac{30A_1 - 80A_2 + 45A_3 - 32A_4}{A_1(\pi\lambda_A + \omega)}\right)$$

for negative cycles. These correction terms assume the availability of the amplitudes of the higher harmonics. While these can be calculated using the usual Fourier technique, it is also possible to approximate some or all them using assumed ratios between the harmonics. For example, for one implementation of a one inch diameter conduit, typical amplitude ratios are $A_1$=1.0, $A_2$=0.01, $A_3$=0.005, and $A_4$=0.001.

e. Application of Amplitude Modulation Compensation to Phase

Simulations have been carried out using the digital transmitter, including the simulation of higher harmonics and amplitude modulation. One example uses f=80 Hz, $A_1$(t=0)=0.3, $A_2$=0, $A_3$=0, $A_4$=0, $\lambda_A$=1e$^{-5}$*48 KHz (sampling rate)=0.47622, which corresponds to a high rate of change of amplitude, but with no higher harmonics. Theory suggests a phase offset of −0.02706 degrees. In simulation over 1000 cycles, the average offset is −0.02714 degrees, with a standard deviation of only 2.17e$^{-6}$. The difference between simulation and theory (approx 0.3% of the simulation error) is attributable to the model's assumption of a linear variation in amplitude over each cycle, while the simulation generates an exponential change in amplitude.

A second example includes a second harmonic, and has the parameters f=80 Hz, $A_1$(t=0)=0.3, $A_2$(t=0)=0.003, $A_3$=0, A4=0, $\lambda_A$=−1e$^{-6}$*48 KHz (sample rate)=−0.047622. For this example, theory predicts the phase offset to be +2.706e$^{-3}$, +/−2.66% for positive or negative cycles. In simulation, the results are $2.714e^{-3}$ +/−2.66%, which again matches well.

Figure 34A:
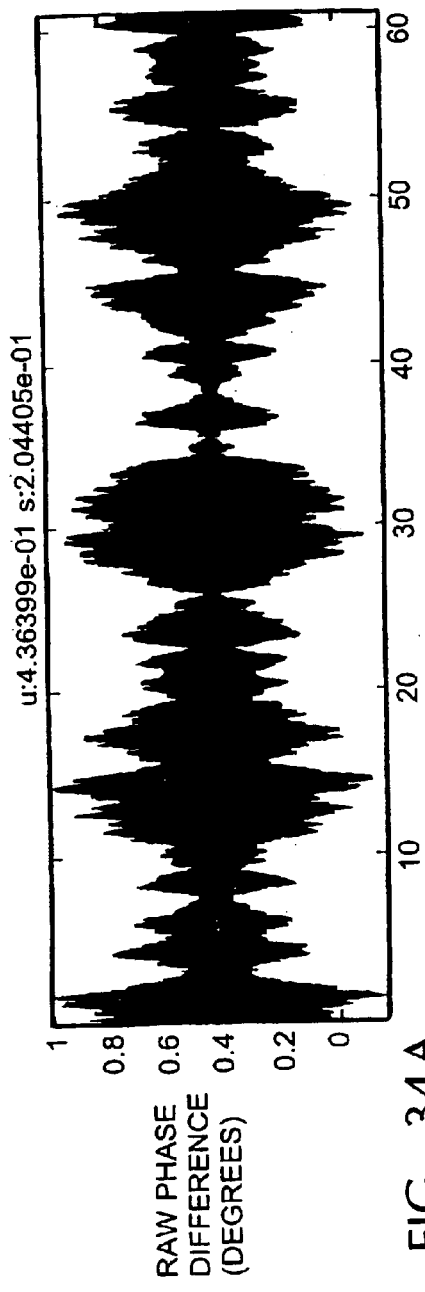
Figure 34B:
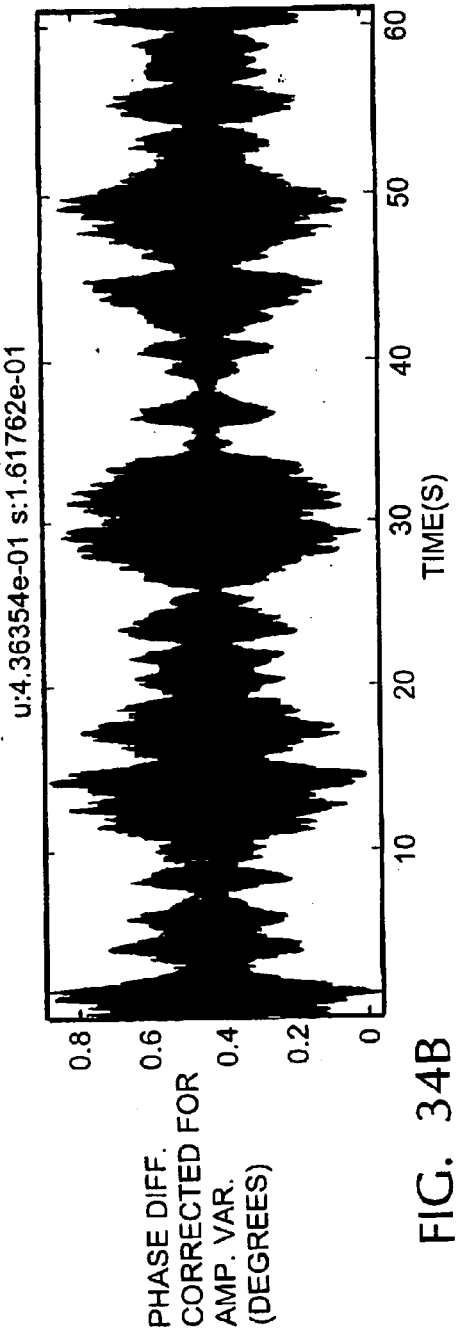

FIGS. 33A–34B give examples of how this correction improves real flowmeter data. FIG. 33A shows raw phase data from $SV_1$, collected from a 1" diameter conduit, with low flow assumed to be reasonably constant. FIG. 33B shows the correction factor calculated using the formula described above, while FIG. 33C shows the resulting corrected phase. The most apparent feature is that the correction has increased the variance of the phase signal, while still producing an overall reduction in the phase difference (i.e., $SV_2$–$SV_1$) standard deviation by a factor of 1.26, as shown in FIGS. 34A and 34B. The improved performance results because this correction improves the correlation between the two phases, leading to reduced variation in the phase difference. The technique works equally well in other flow conditions and on other conduit sizes.

f. Compensation to Phase Measurement for Velocity Effect

The phase measurement calculation is also affected by the velocity effect. A highly effective and simple correction factor, in radians, is of the form $$c_v(t_k) = \frac{1}{\pi} \Delta SV(t_k),$$

where $\Delta SV(t_k)$ is the relative rate of change of amplitude and may be expressed as:

$$\Delta SV(t_k) = \frac{SV(t_{k+1}) - SV(t_{k-1})}{t_{k+1} - t_{k-1}} \cdot \frac{1}{SV(t_k)},$$

where $t_k$ is the completion time for the cycle for which $\Delta SV(t_k)$ is being determined, $t_{k+1}$ is the completion time for the next cycle, and $t_{k-1}$ is the completion time of the previous cycle. $\Delta SV$ is an estimate of the rate of change of SV, scaled by its absolute value, and is also referred to as the proportional rate of change of SV.

Figure 35D:
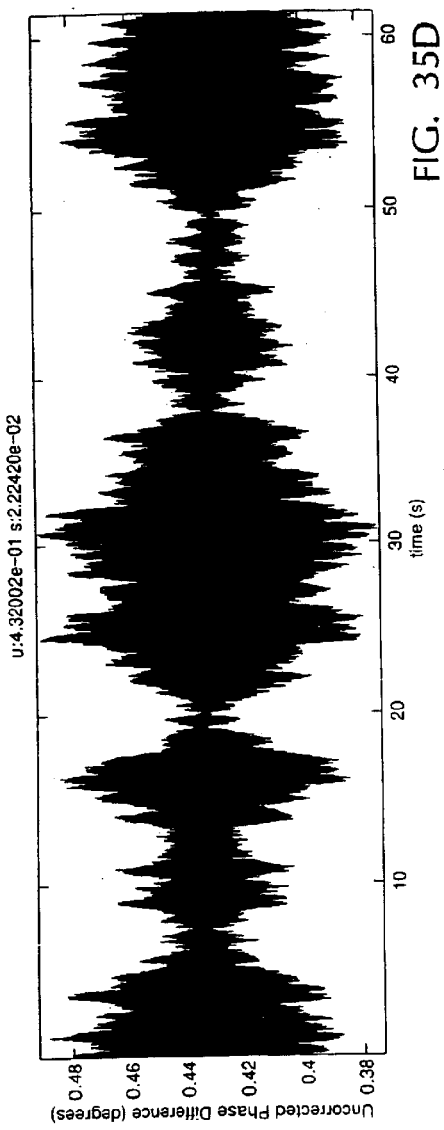
Figure 35E:
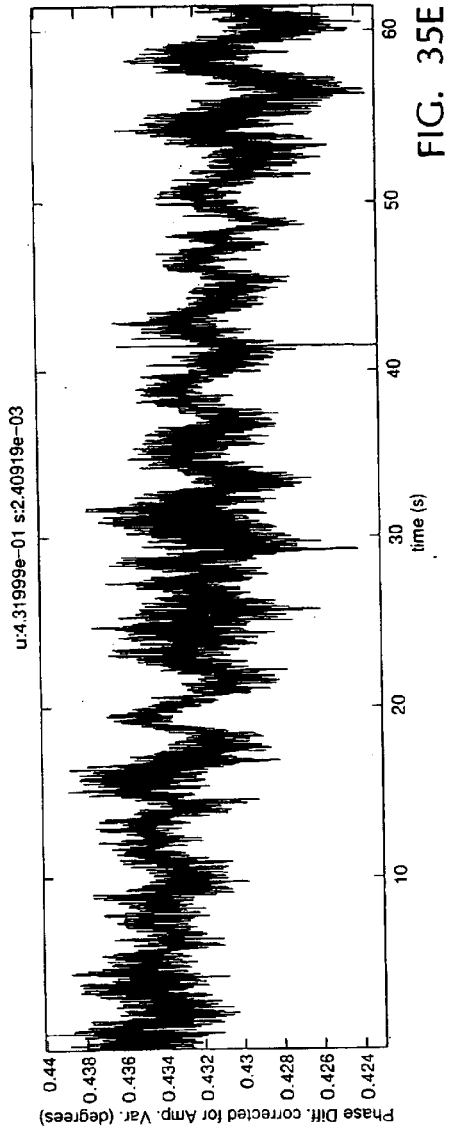

FIGS. 35A–35E illustrate this technique. FIG. 35A shows the raw phase data from a single sensor ($SV_1$), after having applied the amplitude modulation corrections described above. FIG. 35B shows the correction factor in degrees calculated using the equation above, while FIG. 35C shows the resulting corrected phase. It should be noted that the standard deviation of the corrected phase has actually increased relative to the raw data. However, when the corresponding calculations take place on the other sensor ($SV_2$), there is an increase in the negative correlation (from −0.8 to −0.9) between the phases on the two signals. As a consequence, the phase difference calculations based on the raw phase measurements (FIG. 35D) have significantly more noise than the corrected phase measurements (FIG. 35E).

Comparison of FIGS. 35D and 35E shows the benefits of this noise reduction technique. It is immediately apparent from visual inspection of FIG. 35E that the process variable is decreasing, and that there are significant cycles in the measurement, with the cycles being attributable, perhaps, to a poorly conditioned pump. None of this is discernable from the uncorrected phase difference data of FIG. 35D.

g. Application of Sensor Level Noise Reduction

The combination of phase noise reduction techniques described above results in substantial improvements in instantaneous phase difference measurement in a variety of flow conditions, as illustrated in FIGS. 36A–36L. Each graph shows three phase difference measurements calculated simultaneously in real time by the digital Coriolis transmitter operating on a one inch conduit. The middle band 3600 shows phase data calculated using the simple time-difference technique. The outermost band 3605 shows phase data calculated using the Fourier-based technique described above.

It is perhaps surprising that the Fourier technique, which uses far more data, a more sophisticated analysis, and much more computational effort, results in a noisier calculation. This can be attributed to the sensitivity of the Fourier technique to the dynamic effects described above. The innermost band of data 3610 shows the same Fourier data after the application of the sensor-level noise reduction techniques. As can be seen, substantial noise reduction occurs in each case, as indicated by the standard deviation values presented on each graph.

Figure 36A:
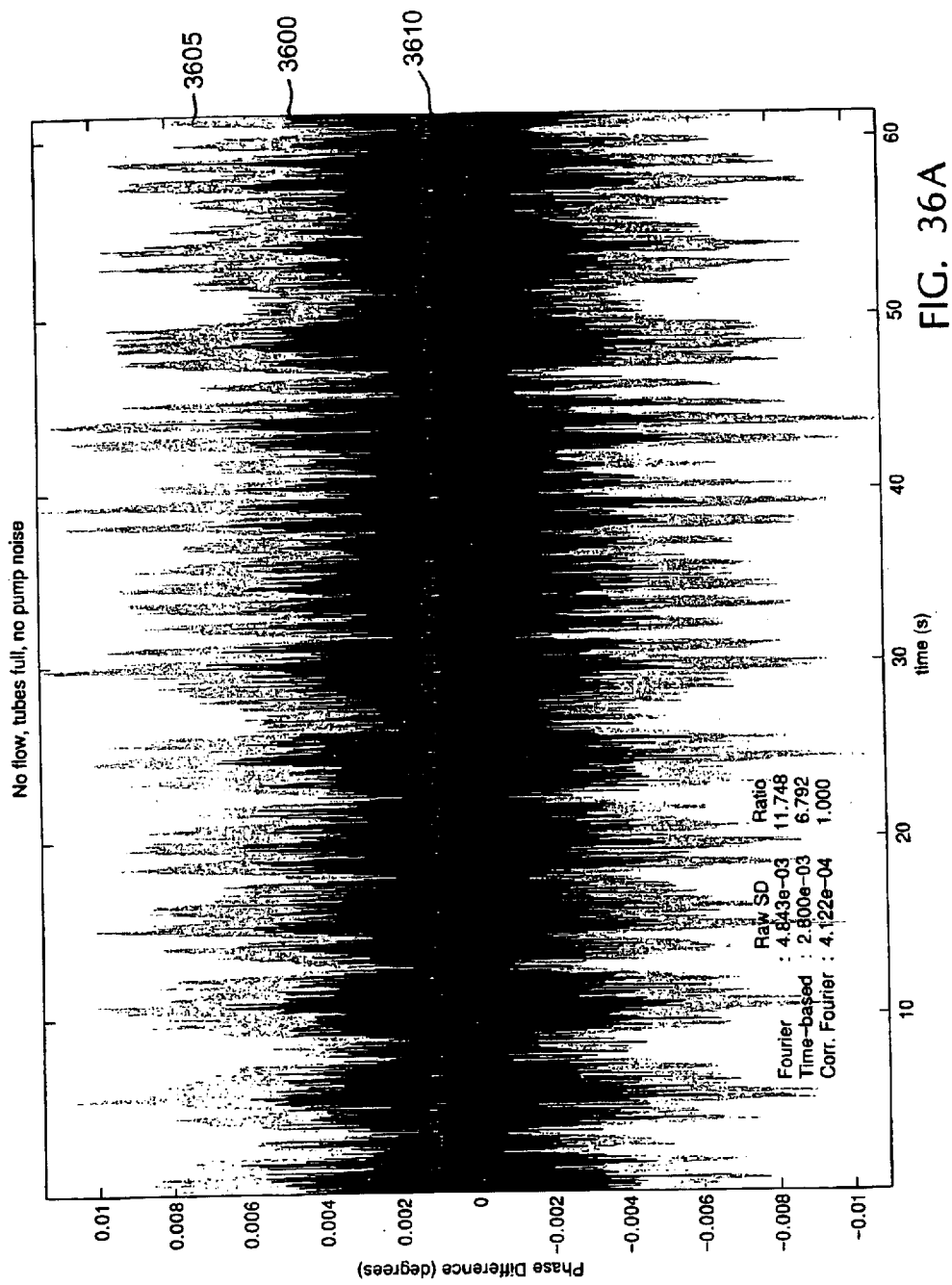
Figure 36B:
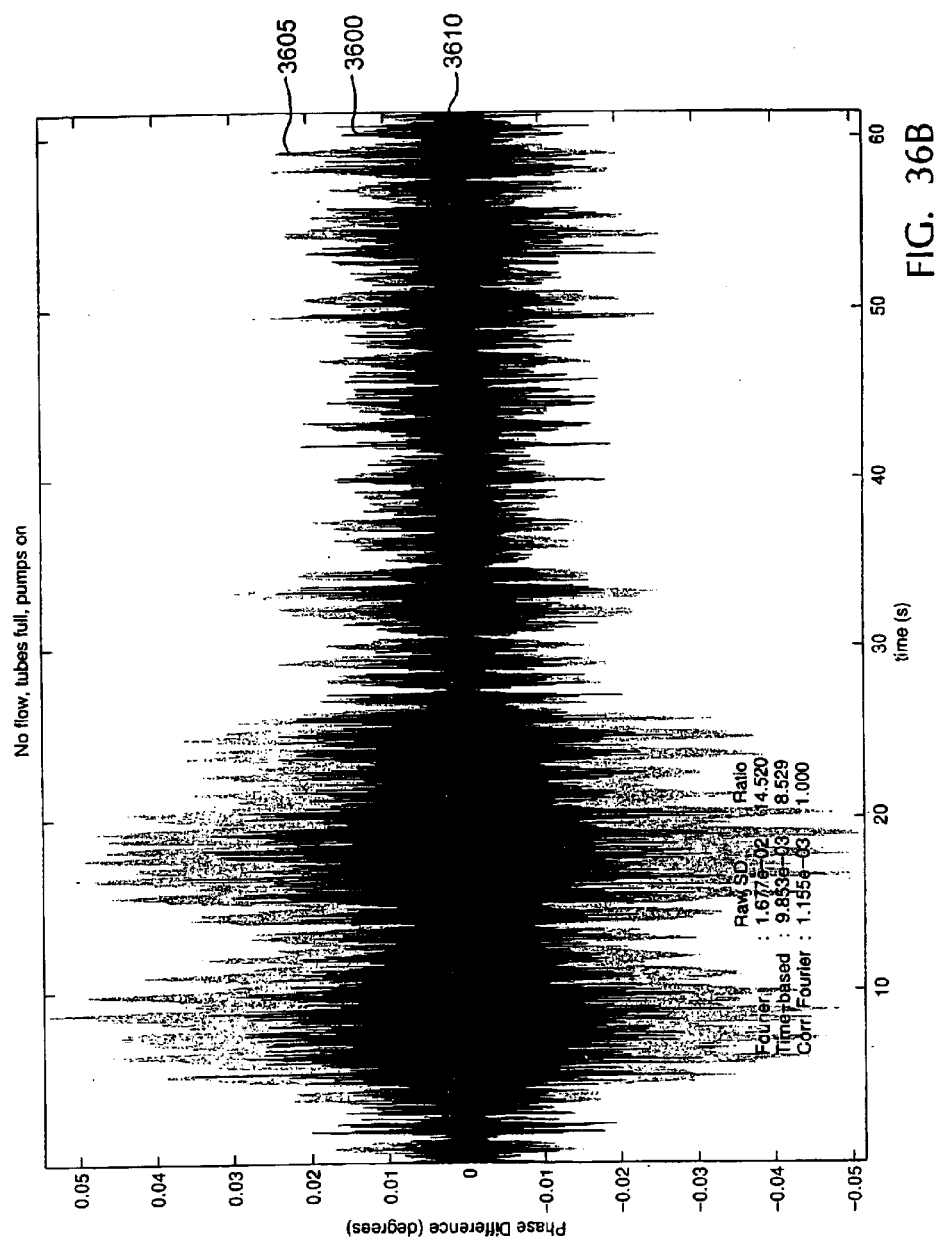
Figure 36C:
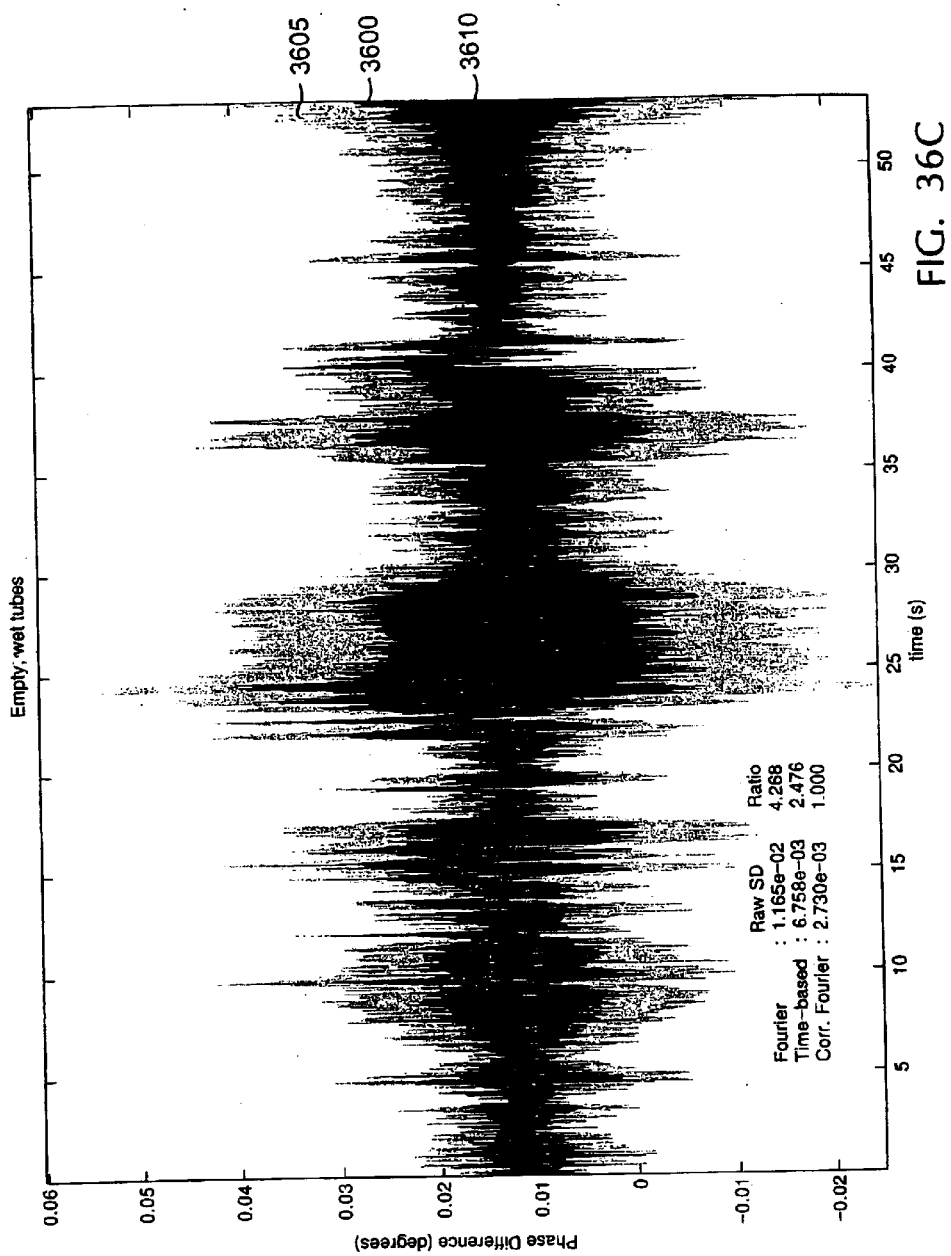
Figure 36D:
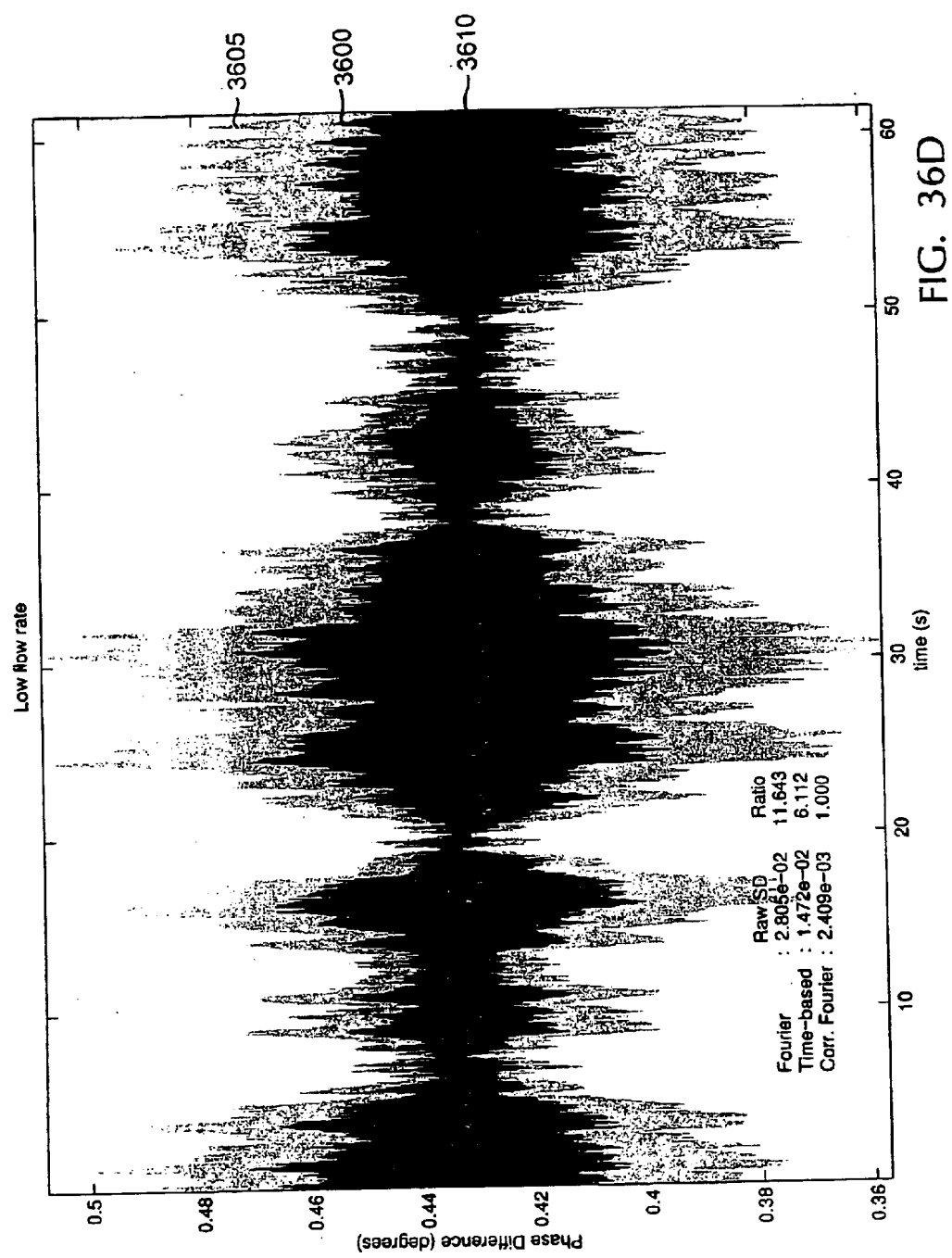
Figure 36E:
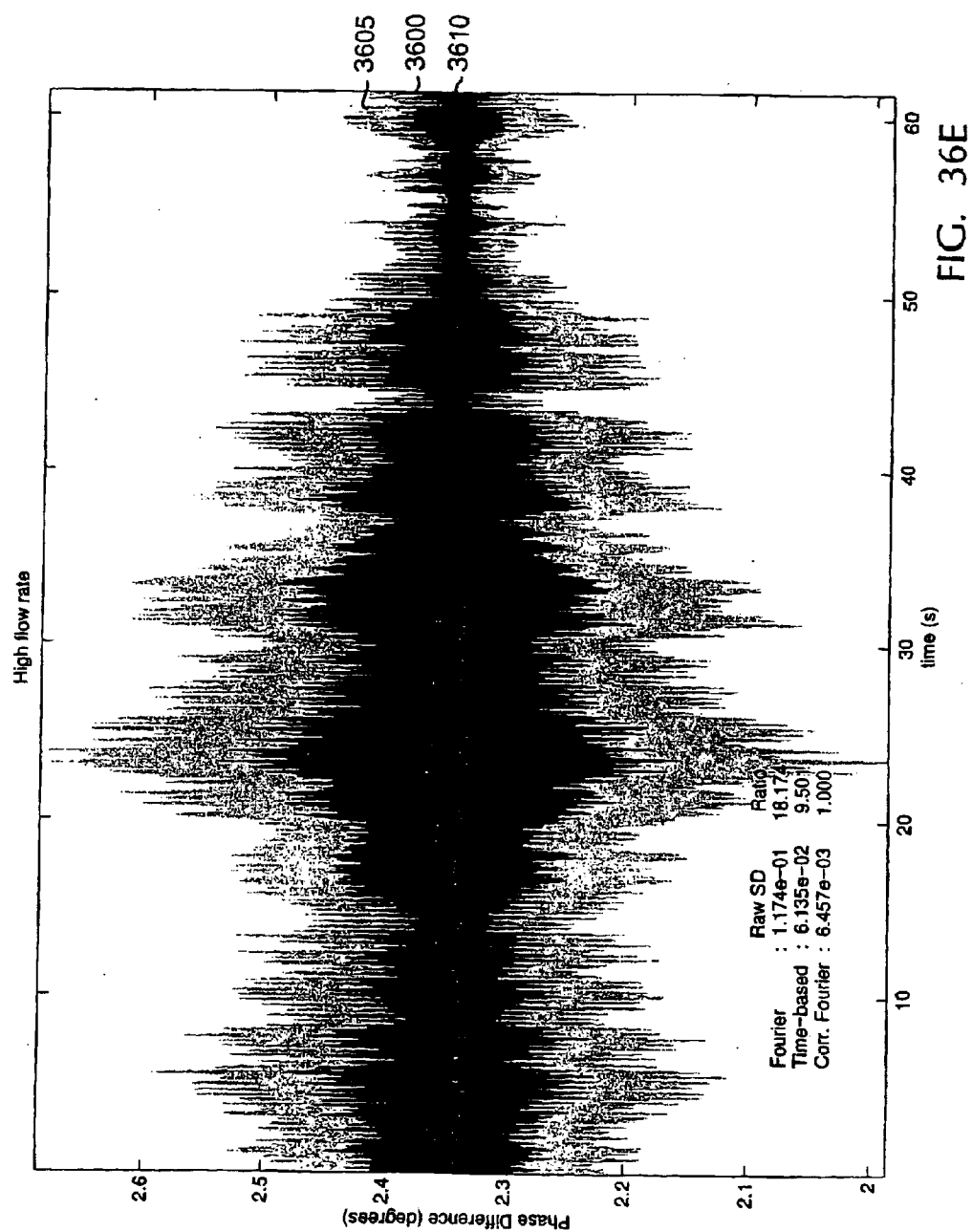
Figure 36F:
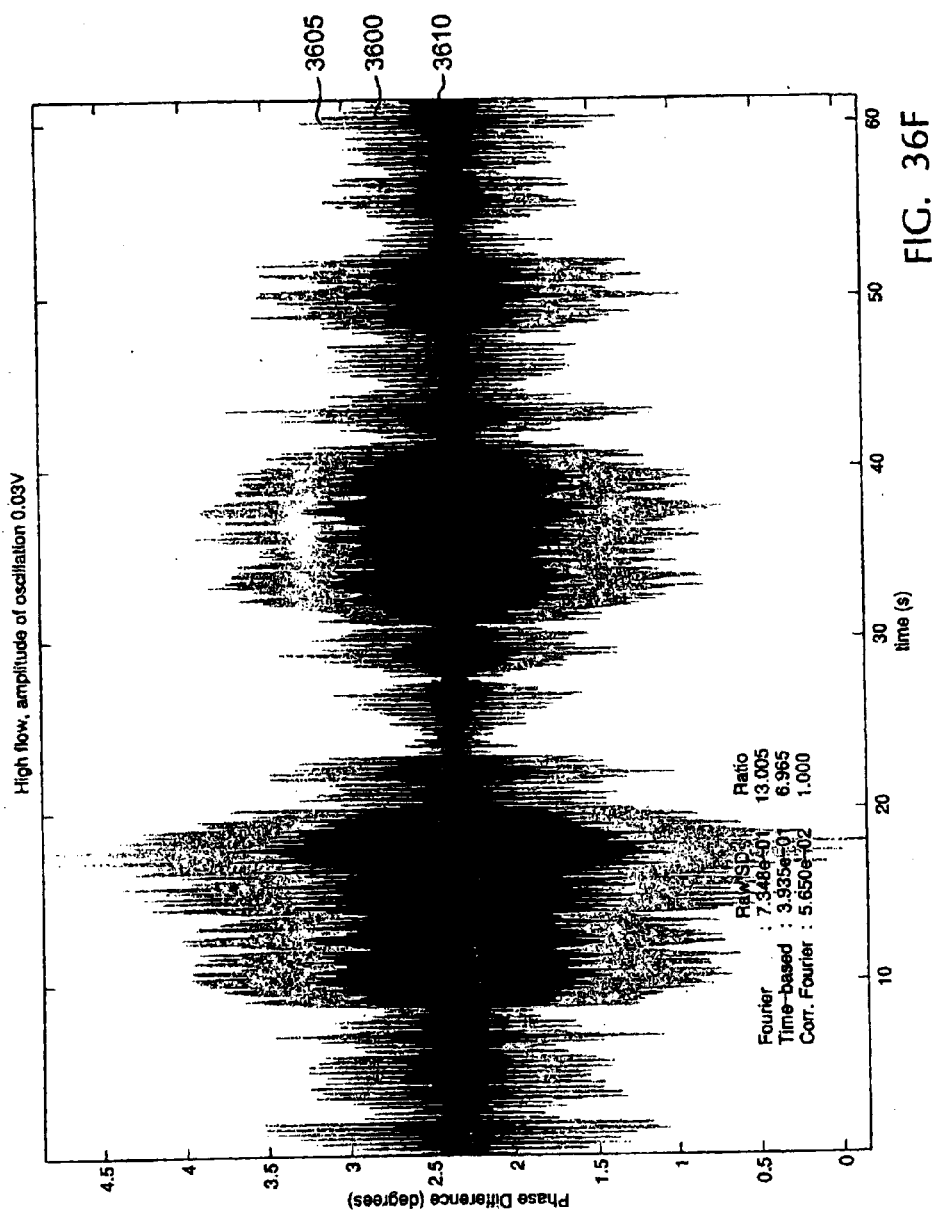
Figure 36G:
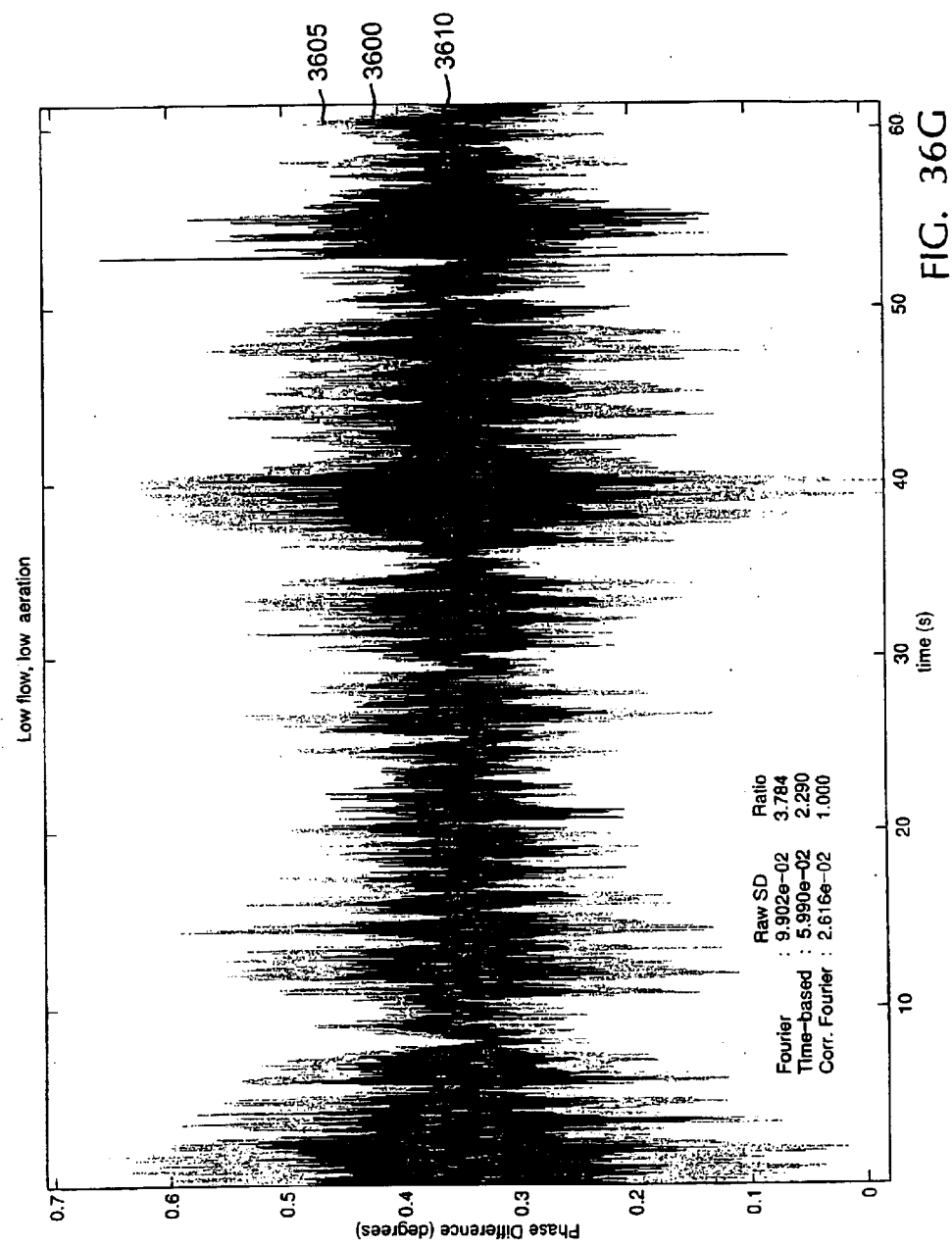
Figure 36H:
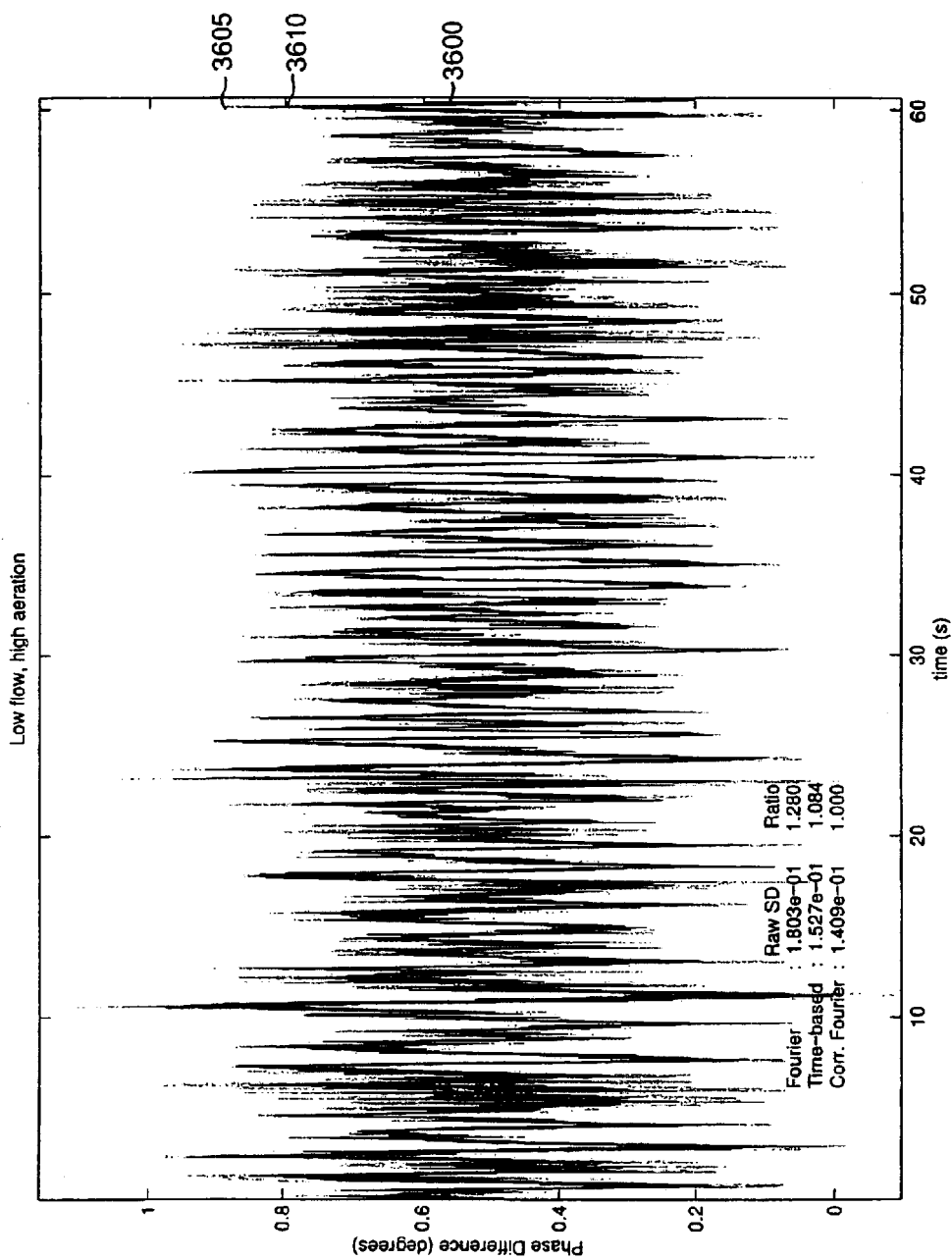
Figure 36I:
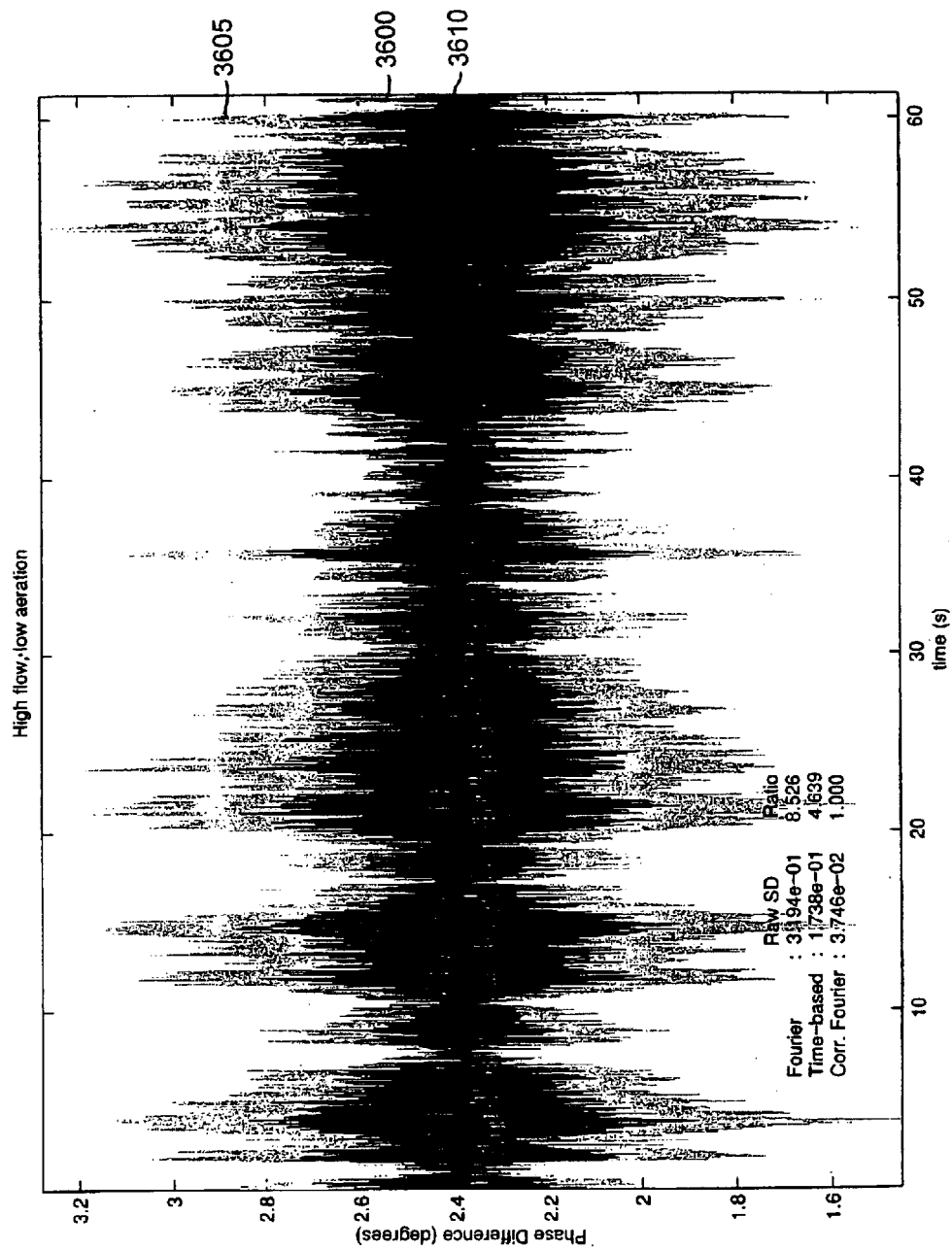
Figure 36J:
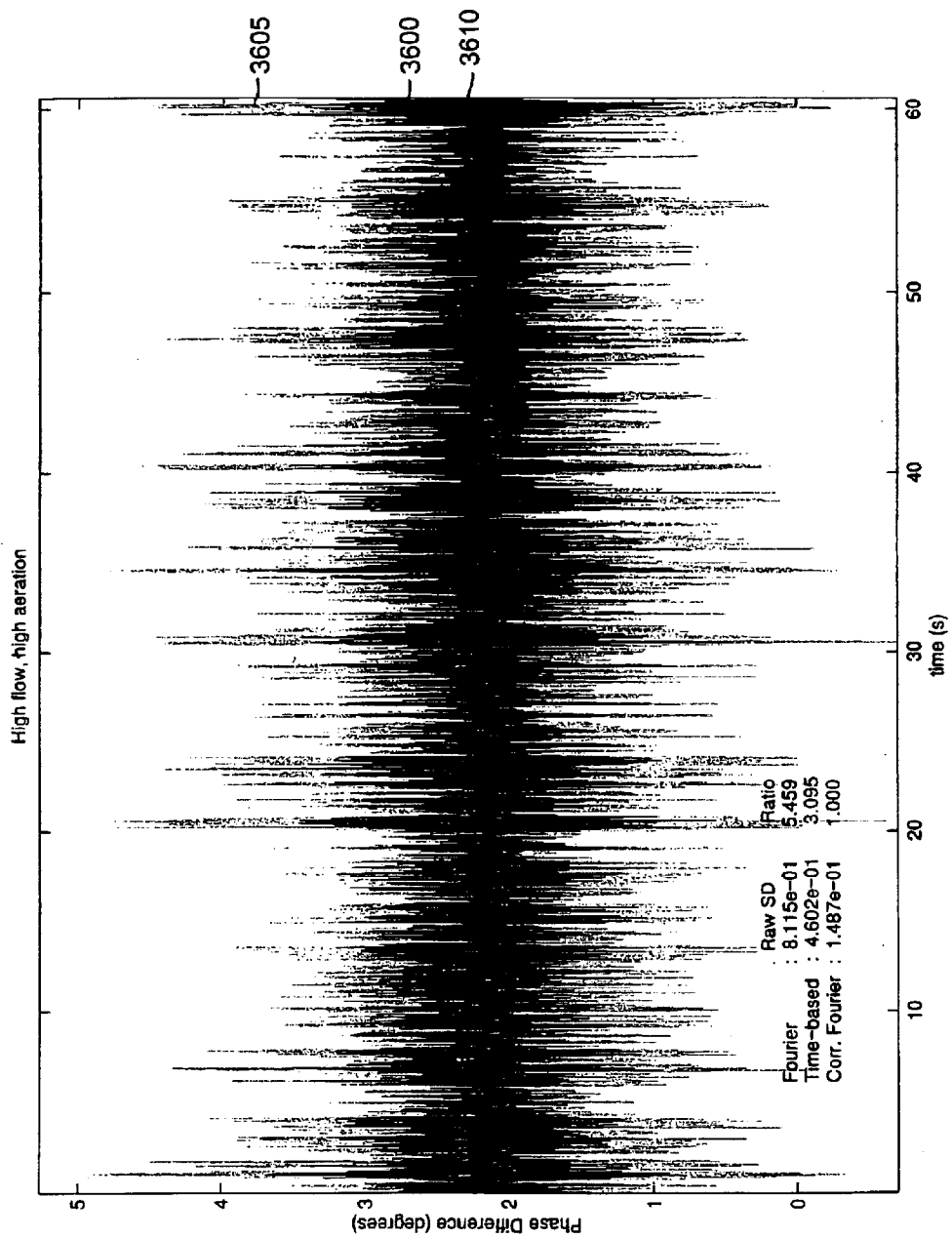
Figure 36L:
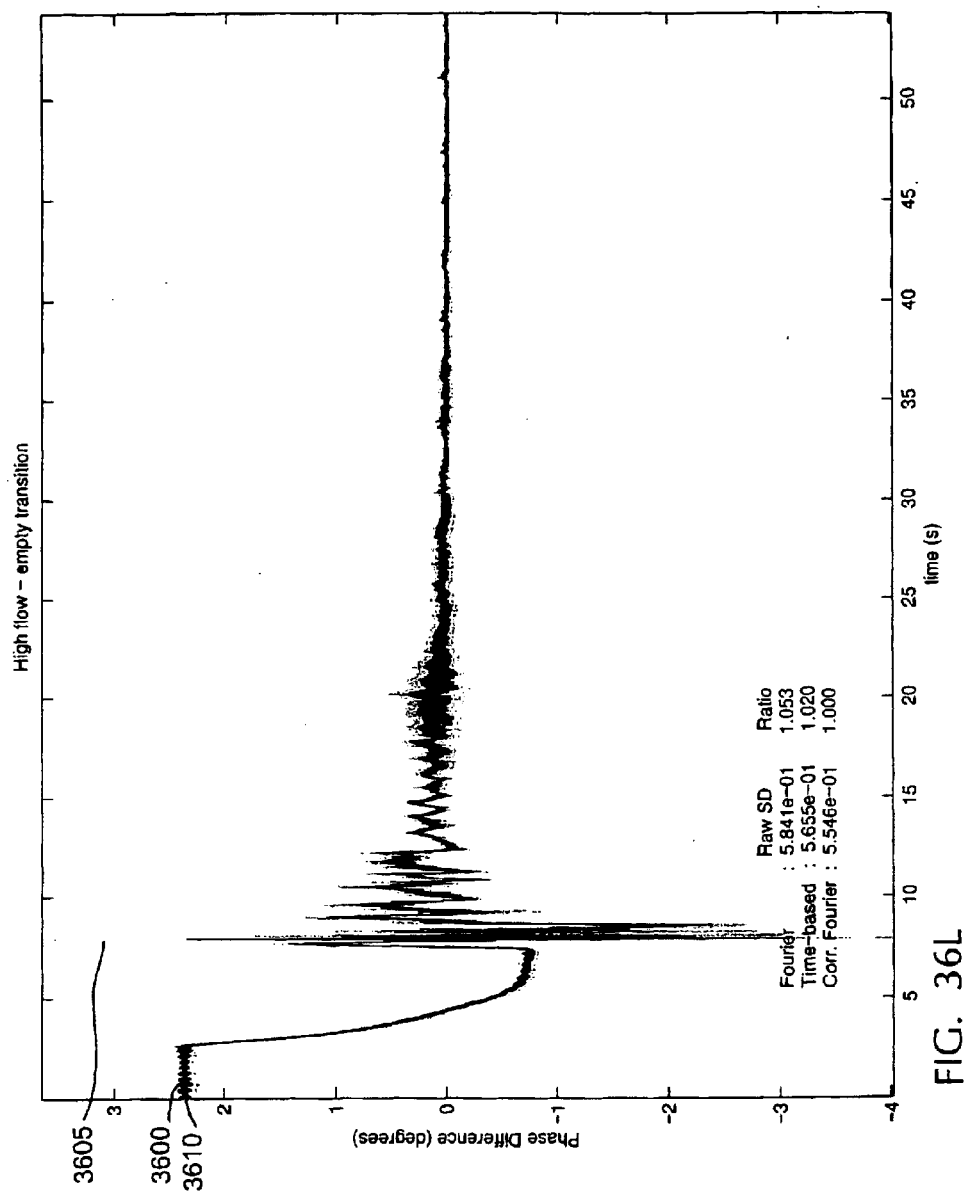

FIG. 36A illustrates measurements with no flow, a full conduit, and no pump noise. FIG. 36B illustrates measurements with no flow, a full conduit, and the pumps on. FIG. 36C illustrates measurements with an empty, wet conduit. FIG. 36D illustrates measurements at a low flow rate. FIG. 36E illustrates measurements at a high flow rate. FIG. 36F illustrates measurements at a high flow rate and an amplitude of oscillation of 0.03 V. FIG. 36G illustrates measurements at a low flow rate with low aeration. FIG. 36H illustrates measurements at a low flow rate with high aeration. FIG. 36I illustrates measurements at a high flow rate with low aeration. FIG. 36J illustrates measurements at a high flow rate with high aeration. FIG. 36K illustrates measurements for an empty to high flow rate transition. FIG. 36L illustrates measurements for a high flow rate to empty transition.

2. Flowtube Level Dynamic Modeling

A dynamic model may be incorporated in two basic stages. In the first stage, the model is created using the techniques of system identification. The flowtube is "stimulated" to manifest its dynamics, while the true mass flow and density values are kept constant. The response of the flowtube is measured and used in generating the dynamic model. In the second stage, the model is applied to normal flow data. Predictions of the effects of flowtube dynamics are made for both phase and frequency. The predictions then are subtracted from the observed data to leave the residual phase and frequency, which should be due to the process alone. Each stage is described in more detail below.

a. System Identification

Figure 37A:
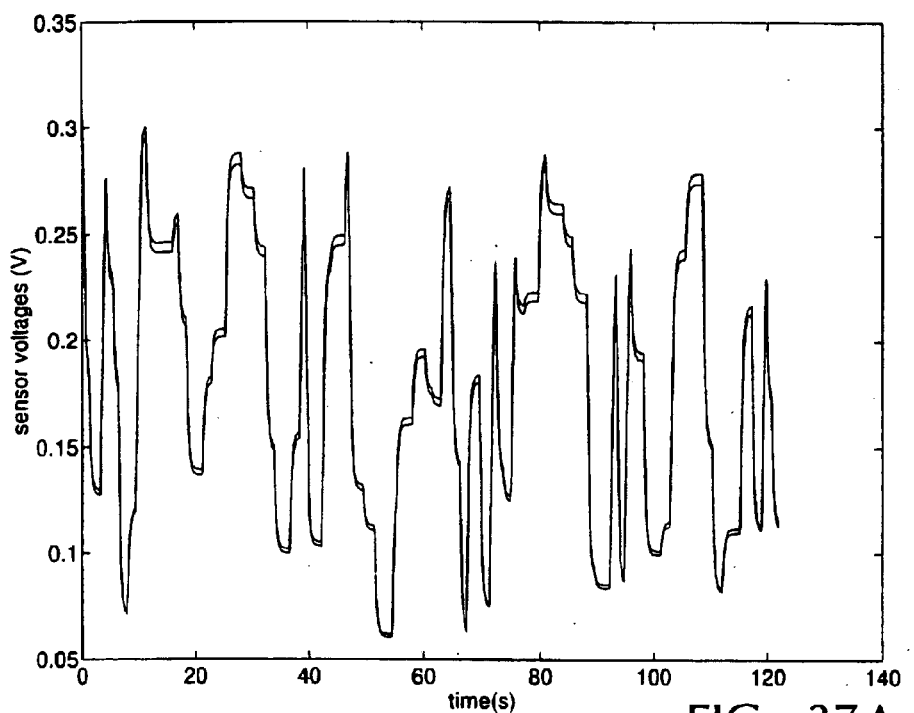
FIG. 37A is a graph of sensor voltages.
Figure 37B:
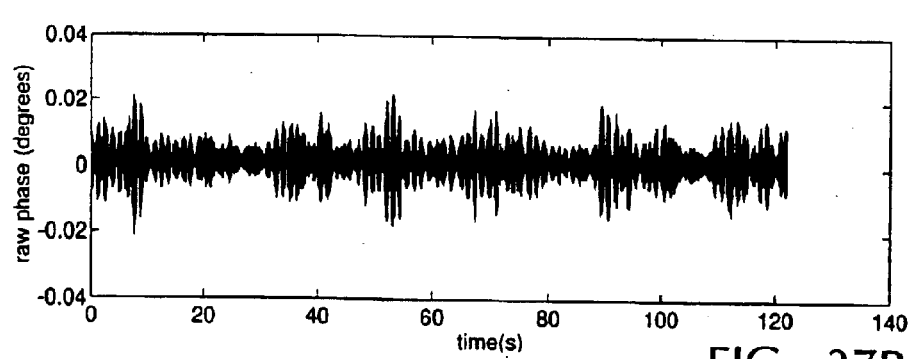
FIGS. 37B and 37C are graphs of phase and frequency measurements corresponding to the sensor voltages of FIG. 37A.
Figure 37C:
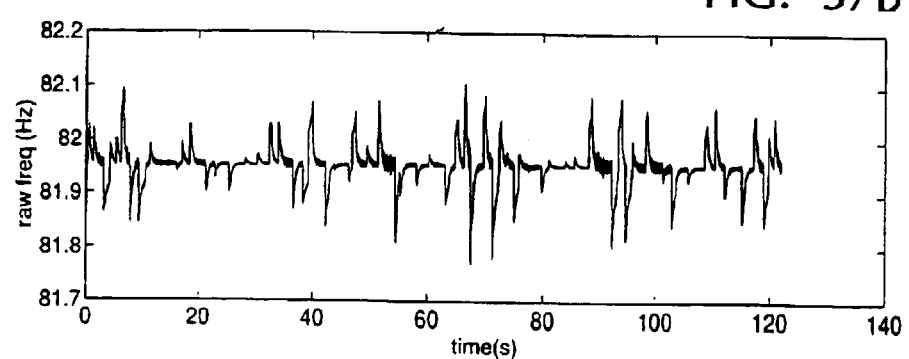

System identification begins with a flowtube full of water, with no flow. The amplitude of oscillation, which normally is kept constant, is allowed to vary by assigning a random setpoint between 0.05 V and 0.3 V, where 0.3 V is the usual value. The resulting sensor voltages are shown in FIG. 37A, while FIGS. 37B and 37C show, respectively, the corresponding calculated phase and frequency values. These values are calculated once per cycle. Both phase and frequency show a high degree of "structure." Since the phase and frequency corresponding to mass flow are constant, this structure is likely to be related to flowtube dynamics. Observable variables that will predict this structure when the true phase and frequency are not known to be constant may be expressed as set forth below.

First, as noted above, $\Delta SV(t_k)$ may be expressed as:

$$\Delta SV(t_k) = \frac{SV(t_{k+1}) - SV(t_{k-1})}{t_{k+1} - t_{k-1}} \cdot \frac{1}{SV(t_k)}.$$

This expression may be used to determine $\Delta SV_1$ and $\Delta SV_2$.

Figure 37D:
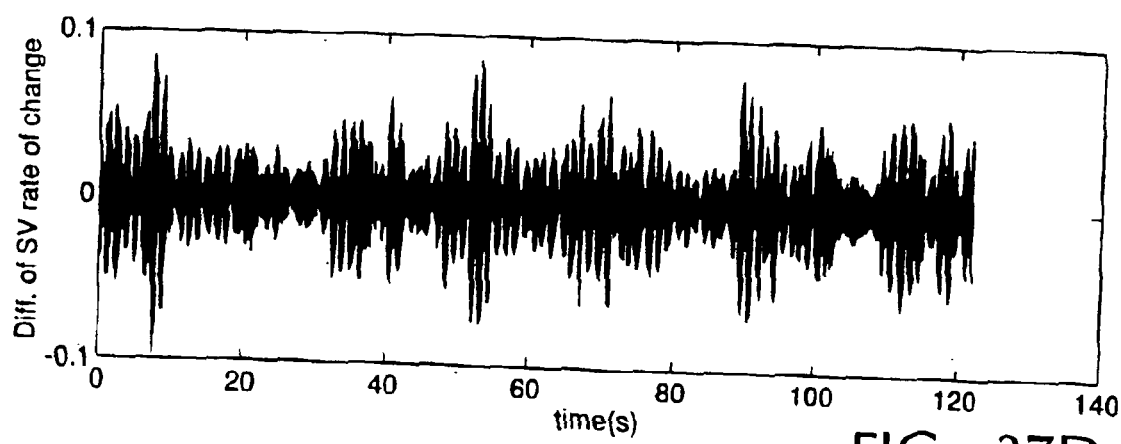
FIGS. 37D and 37E are graphs of correction parameters for the phase and frequency measurements of FIGS. 37B and 37C.
Figure 37E:
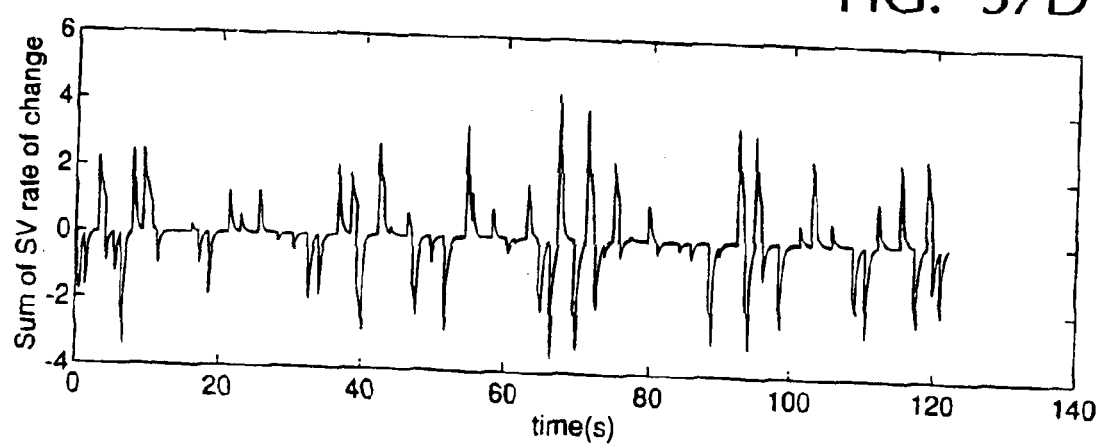

The phase of the flowtube is related to $\Delta$, which is defined as $\Delta SV_1 - \Delta SV_2$, while the frequency is related to $\Delta^+$, which is defined as $\Delta SV_1 + \Delta SV_2$. These parameters are illustrated in FIGS. 37D and 37E. Comparing FIG. 37B to FIG. 37D and FIG. 37C to FIG. 37E shows the striking relationship between $\Delta^-$ and phase and between $\Delta^+$ and frequency.

Some correction for flowtube dynamics may be obtained by subtracting a multiple of the appropriate prediction function from the phase and/or the frequency. Improved results may be obtained using a model of the form:

$$y(k)+a_1y(k-1)+\ldots+a_ny(k-n)=b_0u(k)+b_1u(k-1)+\ldots+b_mu(k-m),$$

where y(k) is the output (i.e., phase or frequency) and u is the prediction function (i.e., $\Delta^-$ or $\Delta^+$). The technique of system identification suggests values for the orders n and m, and the coefficients $a_i$ and $b_j$, of what are in effect polynomials in time. The value of y(k) can be calculated every cycle and subtracted from the observed phase or frequency to get the residual process value.

It is important to appreciate that, even in the absence of dynamic corrections, the digital flowmeter offers very good precision over a long period of time. For example, when totalizing a batch of 200 kg, the device readily achieves a repeatability of less that 0.03%. The purpose of the dynamic modeling is to improve the dynamic precision. Thus, raw and compensated values should have similar mean values, but reductions in "variance" or "standard deviation."

Figure 38A:
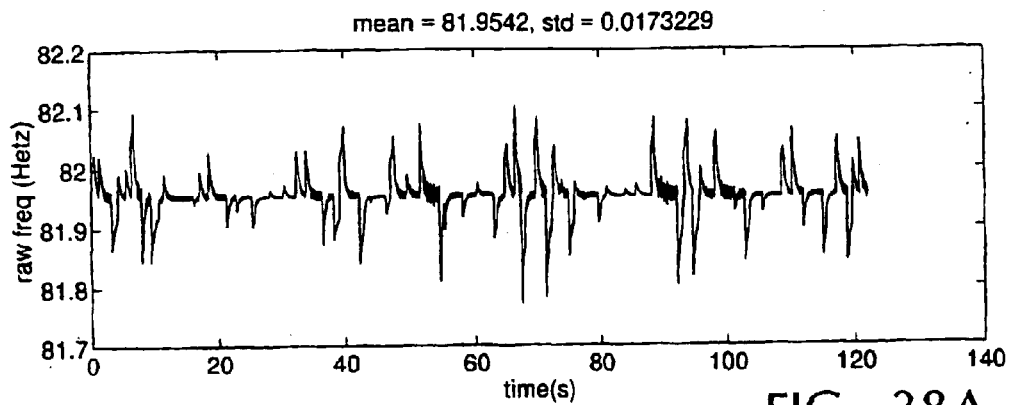
FIGS. 38A–38H are graphs of raw measurements.
Figure 39A:
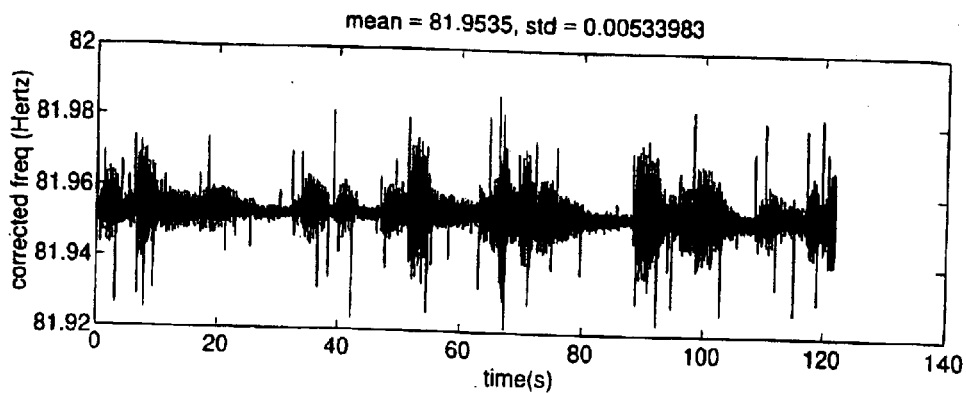
FIGS. 39A–39H are graphs of corrected measurements.

FIGS. 38A and 39A show raw and corrected frequency values. The mean values are similar, but the standard deviation has been reduced by a factor of 3.25. Though the gross deviations in frequency have been eliminated, significant "structure" remains in the residual noise. This structure appears to be unrelated to the $\Delta^+$ function. The model used is a simple first order model, where m=n=1.

Figure 38B:
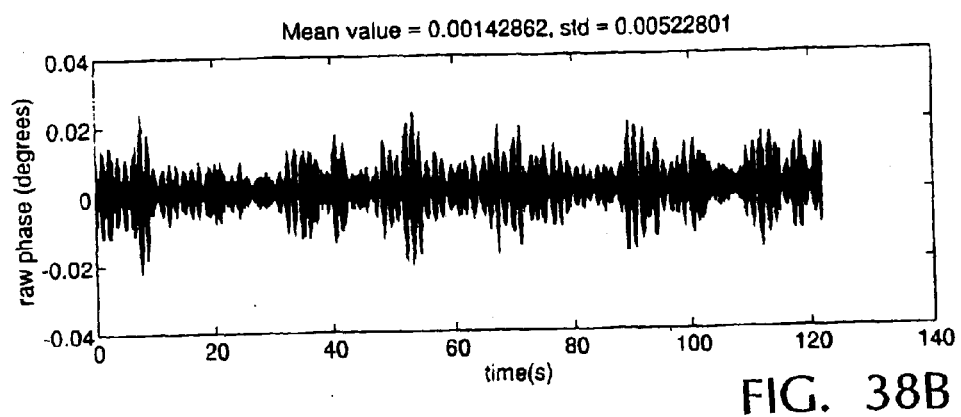
Figure 39B:
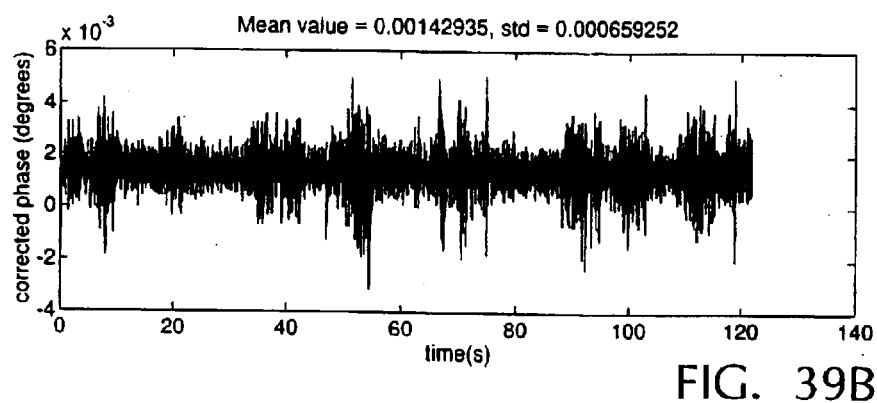

FIGS. 38B and 39B show the corresponding phase correction. The mean value is minimally affected, while the standard deviation is reduced by a factor of 7.9. The model orders are n=2 and m=10. Some structure appears to remain in the residual noise. It is expected that this structure is due to insufficient excitation of the phase dynamics by setpoint changes.

Figure 38C:
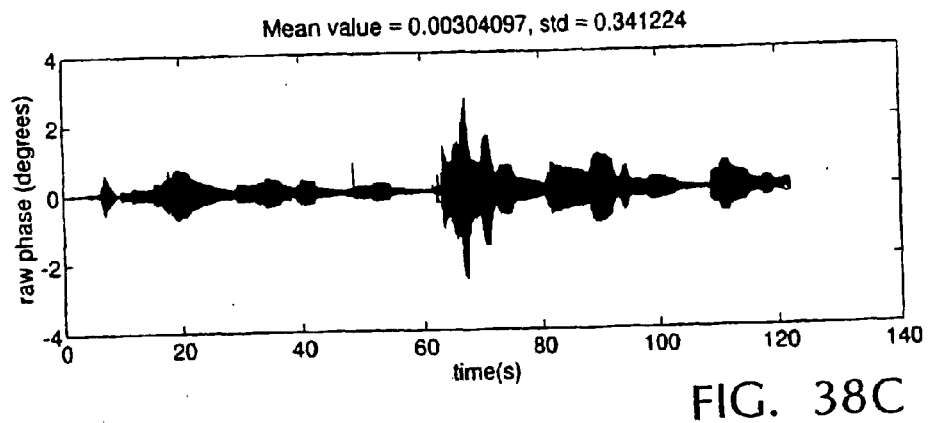
Figure 39C:
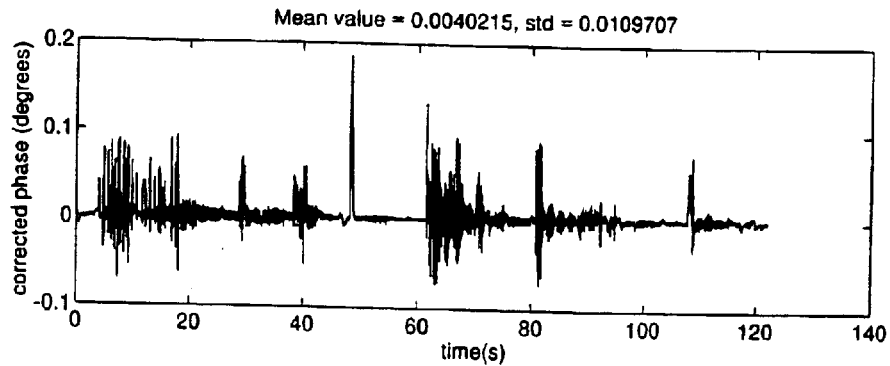

More effective phase identification has been achieved through further simulation of flowtube dynamics by continuous striking of the flowtube during data collection (set point changes are still carried out). FIGS. 38C and 39C show the effects of correction under these conditions. As shown, the standard deviation is reduced by a factor of 31. This more effective model is used in the following discussions.

b. Application to Flow Data

The real test of an identified model is the improvements it provides for new data.

At the outset, it is useful to note a number of observations. First, the mean phase, averaged over, for example, ten seconds or more, is already quite precise. In the examples shown, phase values are plotted at 82 Hz or thereabouts. The reported standard deviation would be roughly ⅓ of the values shown when averaged to 10 Hz, and ⅑ when averages to 1 Hz. For reference, on a one inch flow tube, one degree of phase difference corresponds to about 1 kg/s flow rate.

The expected benefit of the technique is that of providing a much better dynamic response to true process changes, rather than improving average precision. Consequently, in the following examples, where the flow is non-zero, small flow step changes are introduced every ten seconds or so, with the expectation that the corrected phase will show up the step changes more clearly.

Figure 38D:
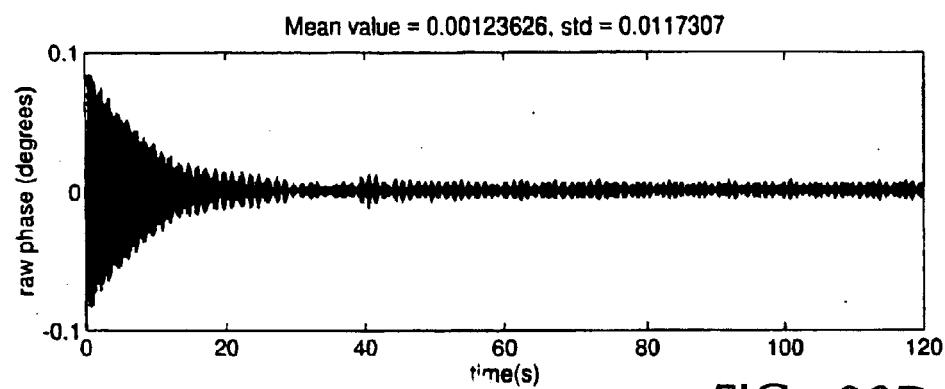
Figure 39D:
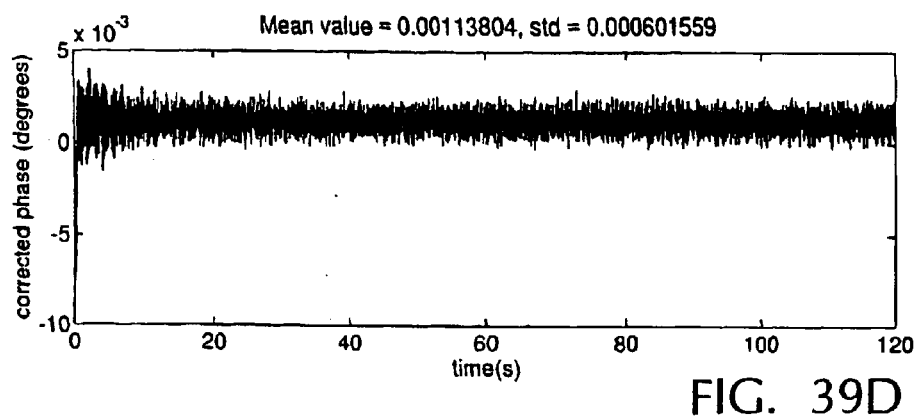

FIGS. 38D and 39D show the correction applied to a full flowtube with zero flow, just after startup. The ring-down effect characteristic of startup is clearly evident in the raw data (FIG. 38D), but this is eliminated by the correction (FIG. 39D), leading to a standard deviation reduction of a factor of 23 over the whole data set. Note that the corrected measurement closely resembles white noise, suggesting most flowtube dynamics have been captured.

Figure 38E:
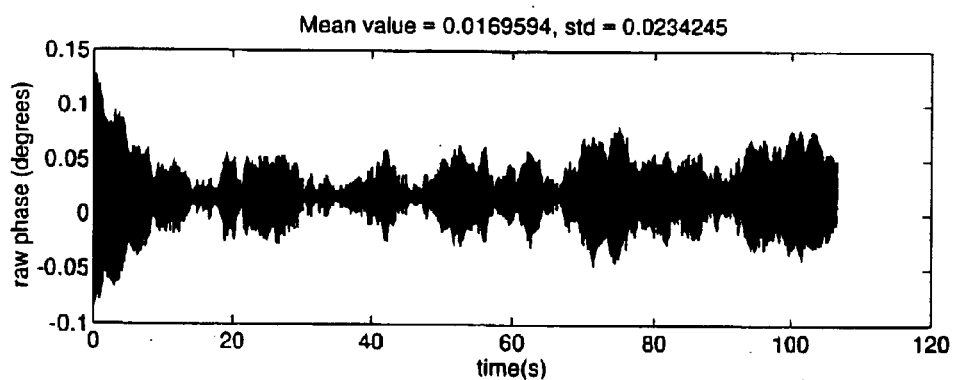
Figure 39E:
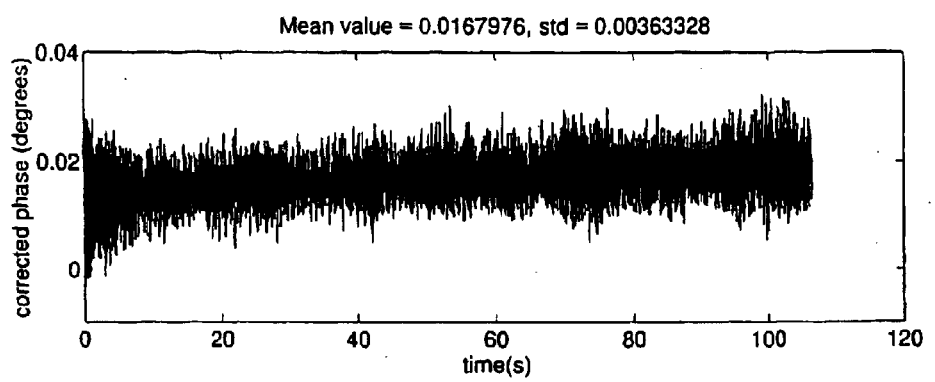

FIGS. 38E and 39E show the resulting correction for a "drained" flowtube. Noise is reduced by a factor of 6.5 or so. Note, however, that there appears to be some residual structure in the noise.

Figure 38F:
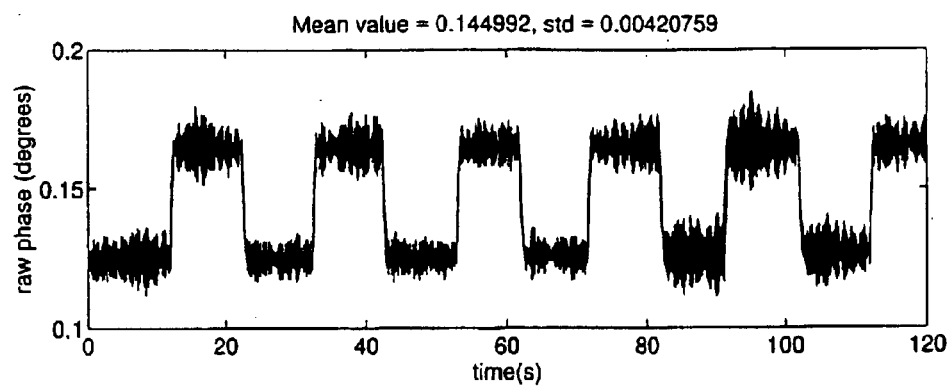
Figure 38G:
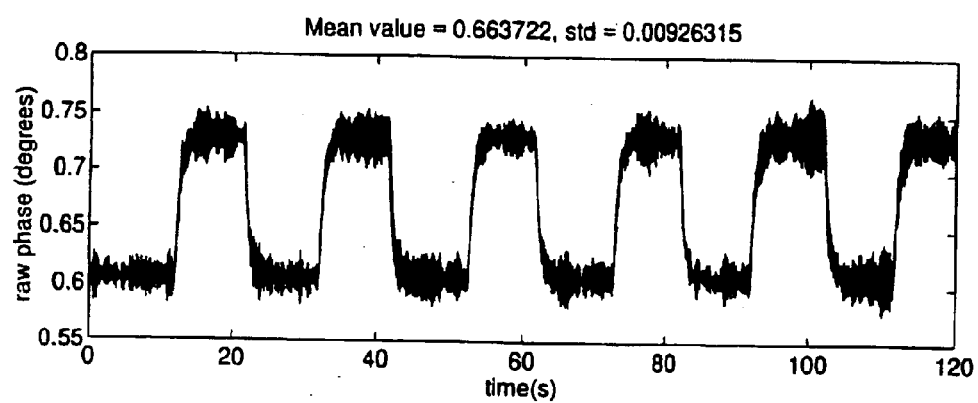
Figure 38H:
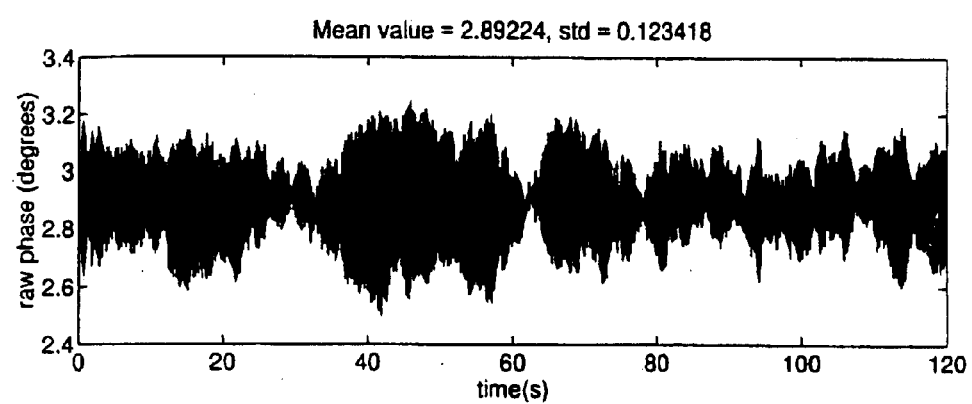
Figure 39F:
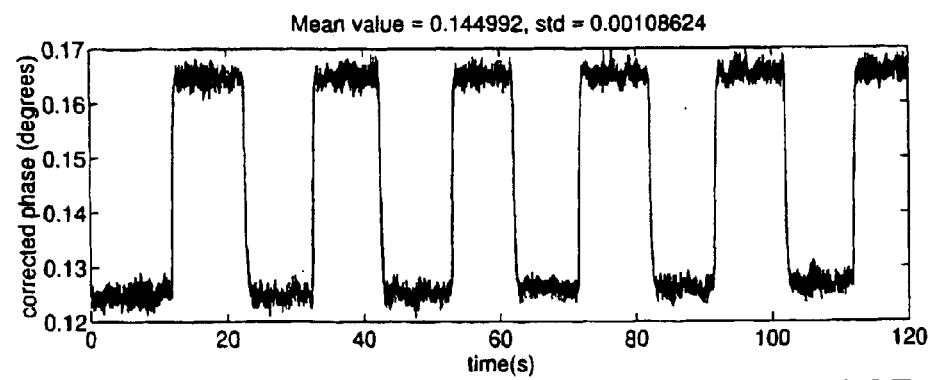
Figure 39G:
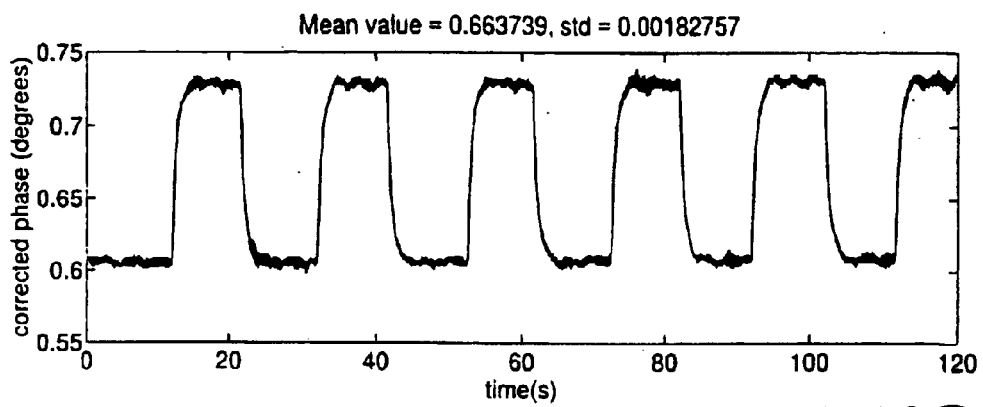
Figure 39H:
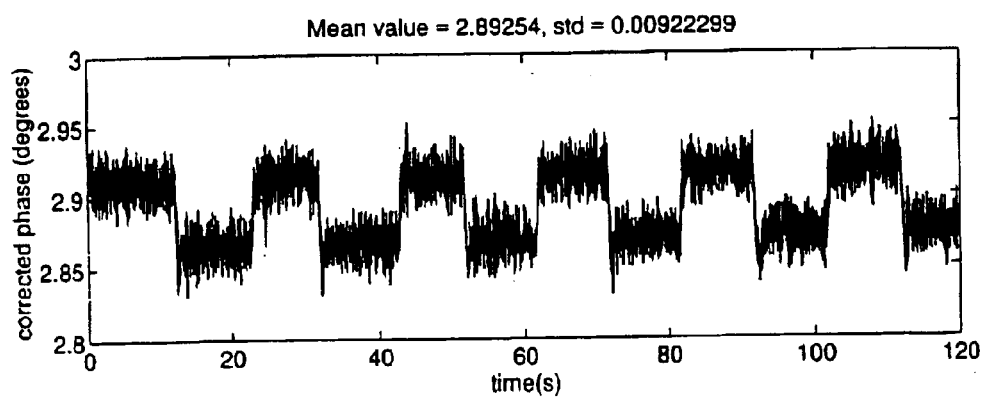

The effects of the technique on low (FIGS. 38F and 39F), medium (FIGS. 38G and 39G), and high (FIGS. 38H and 39H) flow rates are also illustrated, each with step changes in flow every ten seconds. In each case, the pattern is the same: the corrected average flows (FIGS. 39F–39H) are identical to the raw average flows (FIGS. 38F–38H), but the dynamic noise is reduced considerably. In FIG. 39H, this leads to the emergence of the step changes which previously had been submerged in noise (FIG. 38H).

3. Extensions of Dynamic Monitoring and Compensation Techniques

The previous sections have described a variety of techniques (physical modeling, system identification, heuristics) used to monitor and compensate for different aspects of dynamic behavior (frequency and phase noise caused by amplitude modulation, velocity effect, flowtube dynamics at both the sensor and the flowtube level). By natural extension, similar techniques well-known to practitioners of control and/or instrumentation, including those of artificial intelligence, neural networks, fuzzy logic, and genetic algorithms, as well as classical modeling and identification methods, may be applied to these and other aspects of the dynamic performance of the meter. Specifically, these might include monitoring and compensation for frequency, amplitude and/or phase variation at the sensor level, as well as average frequency and phase difference at the flowtube level, as these variations occur within each measurement interval, as well as the time between measurement intervals (where measurement intervals do not overlap).

This technique is unusual in providing both reduced noise and improved dynamic response to process measurement changes. As such, the technique promises to be highly valuable in the context of flow measurement.

I. Aeration

The digital flowmeter provides improved performance in the presence of aeration in the conduit. Aeration causes energy losses in the conduit that can have a substantial negative impact on the measurements produced by a mass flowmeter and can result in stalling of the conduit. Experiments have shown that the digital flowmeter has substantially improved performance in the presence of aeration relative to traditional, analog flowmeters. This performance improvement may stem from the meter's ability to provide a very wide gain range, to employ negative feedback, to calculate measurements precisely at very low amplitude levels, and to compensate for dynamic effects such as rate of change of amplitude and flowtube dynamics, and also may stem from the meter's use of a precise digital amplitude control algorithm.

The digital flowmeter detects the onset of aeration when the required driver gain rises simultaneously with a drop in apparent fluid density. The digital flowmeter then may directly respond to detected aeration. In general, the meter monitors the presence of aeration by comparing the observed density of the material flowing through the conduit (i.e., the density measurement obtained through normal measurement techniques) to the known, nonaerated density of the material. The controller determines the level of aeration based on any difference between the observed and actual densities. The controller then corrects the mass flow measurement accordingly.

The controller determines the non-aerated density of the material by monitoring the density over time periods in which aeration is not present (i.e., periods in which the density has a stable value). Alternatively, a control system to which the controller is connected may provide the non-aerated density as an initialization parameter.

In one implementation, the controller uses three corrections to account for the effects of aeration: bubble effect correction, damping effect correction, and sensor imbalance correction. FIGS. 40A–40H illustrate the effects of the correction procedure.

Figure 40A:
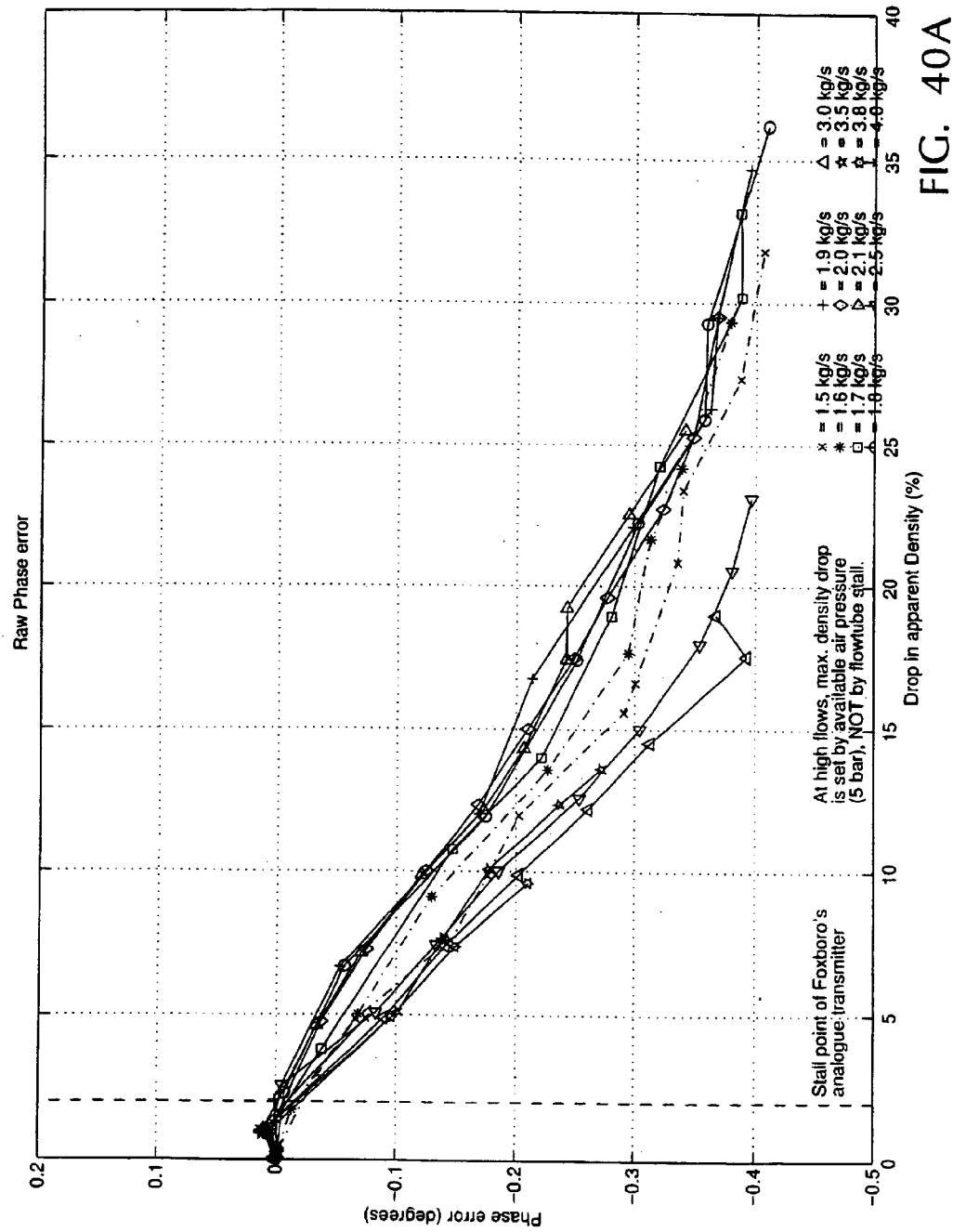
Figure 40B:
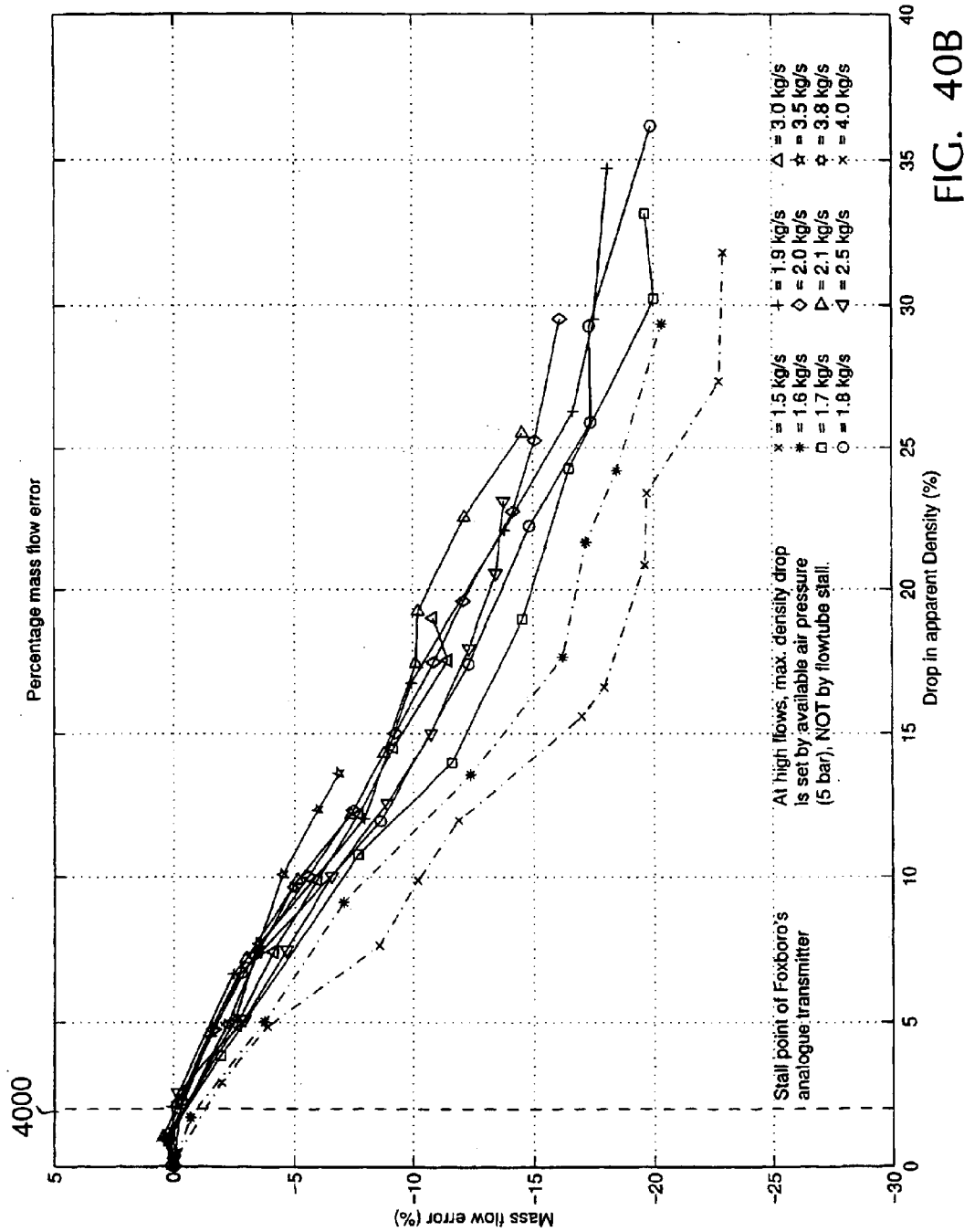

FIG. 40A illustrates the error in the phase measurement as the measured density decreases (i.e., as aeration increases) for different mass flow rates, absent aeration correction. As shown, the phase error is negative and has a magnitude that increases with increasing aeration. FIG. 40B illustrates that the resulting mass flow error is also negative. It also is significant to note that the digital flowmeter operates at high levels of aeration. By contrast, as indicated by the horizontal bar 4000, traditional analog meters tend to stall in the presence of low levels of aeration.

A stall occurs when the flowmeter is unable to provide a sufficiently large driver gain to allow high drive current at low amplitudes of oscillation. If the level of damping requires a higher driver gain than can be delivered by the flowtube in order to maintain oscillation at a certain amplitude, then insufficient drive energy is supplied to the conduit. This results in a drop in amplitude of oscillation, which in turn leads to even less drive energy supplied due to the maximum gain limit. Catastrophic collapse results, and flowtube oscillation is not possible until the damping reduces to a level at which the corresponding driver gain requirement can be supplied by the flowmeter.

Figure 40C:
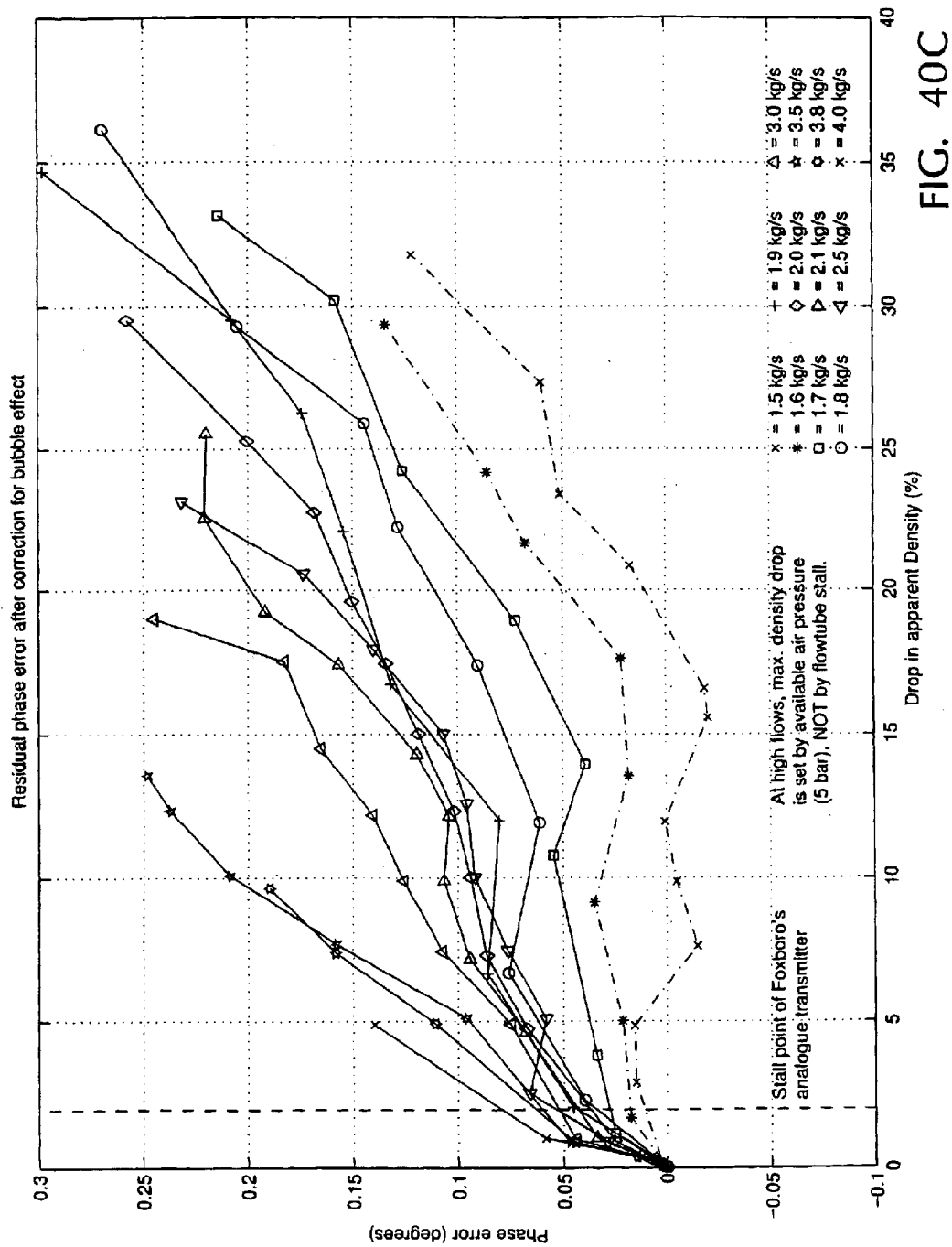

The bubble effect correction is based on the assumption that the mass flow decreases as the level of aeration, also referred to as the void fraction, increases. Without attempting to predict the actual relationship between void fraction and the bubble effect, this correction assumes, with good theoretical justification, that the effect on the observed mass flow will be the same as the effect on the observed density. Since the true fluid density is known, the bubble effect correction corrects the mass flow rate by the same proportion. This correction is a linear adjustment that is the same for all flow rates. FIGS. 40C and 40D illustrate, respectively, the residual phase and mass flow errors after correction for the bubble effect. As shown, the residual errors are now positive and substantially smaller in magnitude than the original errors.

The damping factor correction accounts for damping of the conduit motion due to aeration. In general, the damping factor correction is based on the following relationship between the observed phase, $\varphi_{obs}$, and the actual phase, $\varphi_{true}$:

$$\varphi_{obs} = \varphi_{true}\left(1 + \frac{k\lambda^2 \varphi_{true}}{f^2}\right),$$

where $\lambda$ is a damping coefficient and k is a constant. FIG. 40E illustrates the damping correction for different mass flow rates and different levels of aeration. FIG. 40F illustrates the residual phase error after correction for damping. As shown, the phase error is reduced substantially relative to the phase error remaining after bubble effect correction.

Figure 41:
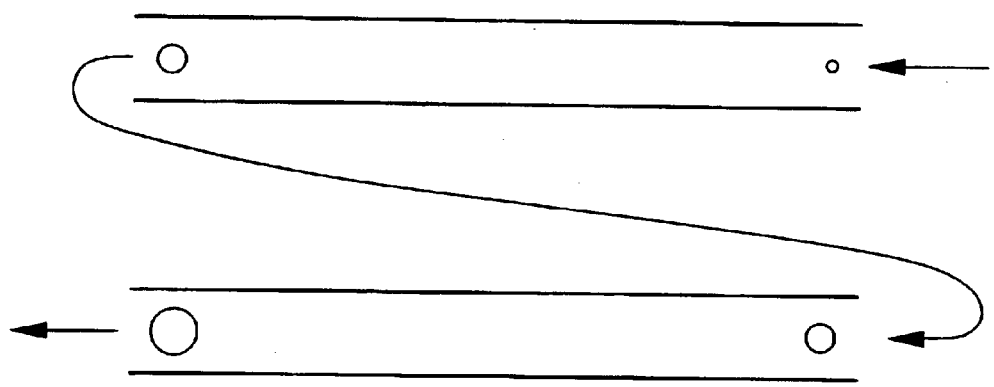
FIG. 41 is a block diagram illustrating the effect of aeration in a conduit.

The sensor balance correction is based on density differences between different ends of the conduit. As shown in FIG. 41, a pressure drop between the inlet and the outlet of the conduit results in increasing bubble sizes from the inlet to the outlet. Since material flows serially through the two loops of the conduit, the bubbles at the inlet side of the conduit (i.e., the side adjacent to the first sensor/driver pair) will be smaller than the bubbles at the outlet side of the conduit (i.e., the side adjacent to the second sensor/driver pair). This difference in bubble size results in a difference in mass and density between the two ends of the conduit. This difference is reflected in the sensor signals ($SV_1$ and $SV_2$). Accordingly, the sensor balance correction is based on a ratio of the two sensor signals.

Figure 40G:
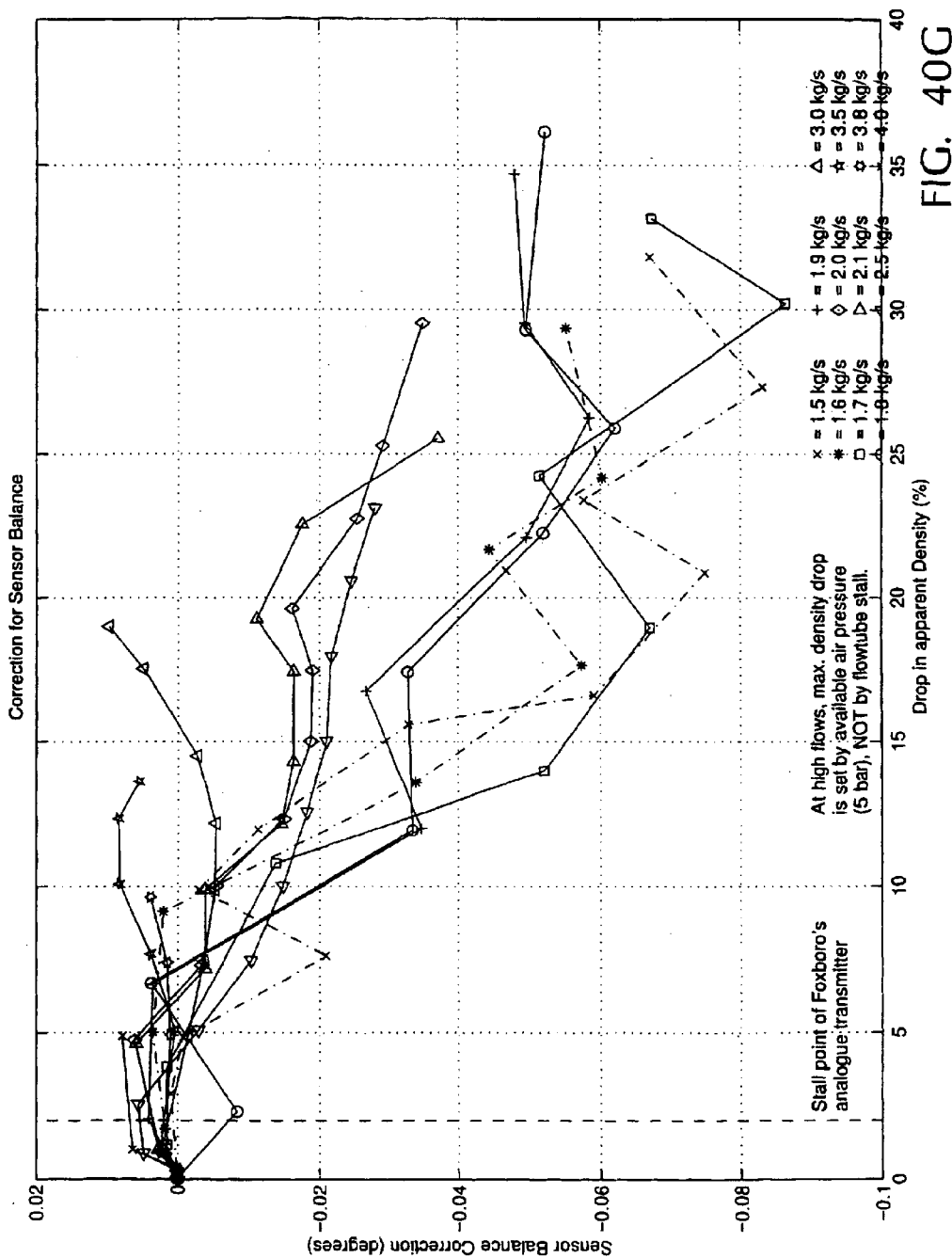

FIG. 40G illustrates the sensor balance correction for different mass flow rates and different levels of aeration. FIG. 40H illustrates the residual phase error after applying the sensor balance correction. At low flow rates and low levels of aeration, the phase error is improved relative to the phase error remaining after damping correction.

Other correction factors also could be used. For example, the phase angle of each sensor signal could be monitored. In general, the average phase angle for a signal should be zero. However, the average phase angle tends to increase with increasing aeration. Accordingly, a correction factor could be generated based on the value of the average phase angle. Another correction factor could be based on the temperature of the conduit.

In general, application of the correction factors tends to keep the mass flow errors at one percent or less. Moreover, these correction factors appear to be applicable over a wide range of flows and aeration levels.

J. Setpoint Adjustment

The digital flowmeter provides improved control of the setpoint for the amplitude of oscillation of the conduit. In an analog meter, feedback control is used to maintain the amplitude of oscillation of the conduit at a fixed level corresponding to a desired peak sensor voltage (e.g., 0.3 V). A stable amplitude of oscillation leads to reduced variance in the frequency and phase measurements.

In general, a large amplitude of oscillation is desirable, since such a large amplitude provides a large Coriolis signal for measurement purposes. A large amplitude of oscillation also results in storage of a higher level of energy in the conduit, which provides greater robustness to external vibrations.

Circumstances may arise in which it is not possible to maintain the large amplitude of oscillation due to limitations in the current that can be supplied to the drivers. For example, in one implementation of an analog transmitter, the current is limited to 100 mA for safety purposes. This is typically 5–10 times the current needed to maintain the desired amplitude of oscillation. However, if the process fluid provides significant additional damping (e.g., via two-phase flow), then the optimal amplitude may no longer be sustainable.

Similarly, a low-power flowmeter, such as the two-wire meter described below, may have much less power available to drive the conduit. In addition, the power level may vary when the conduit is driven by capacitive discharge.

Figure 42:
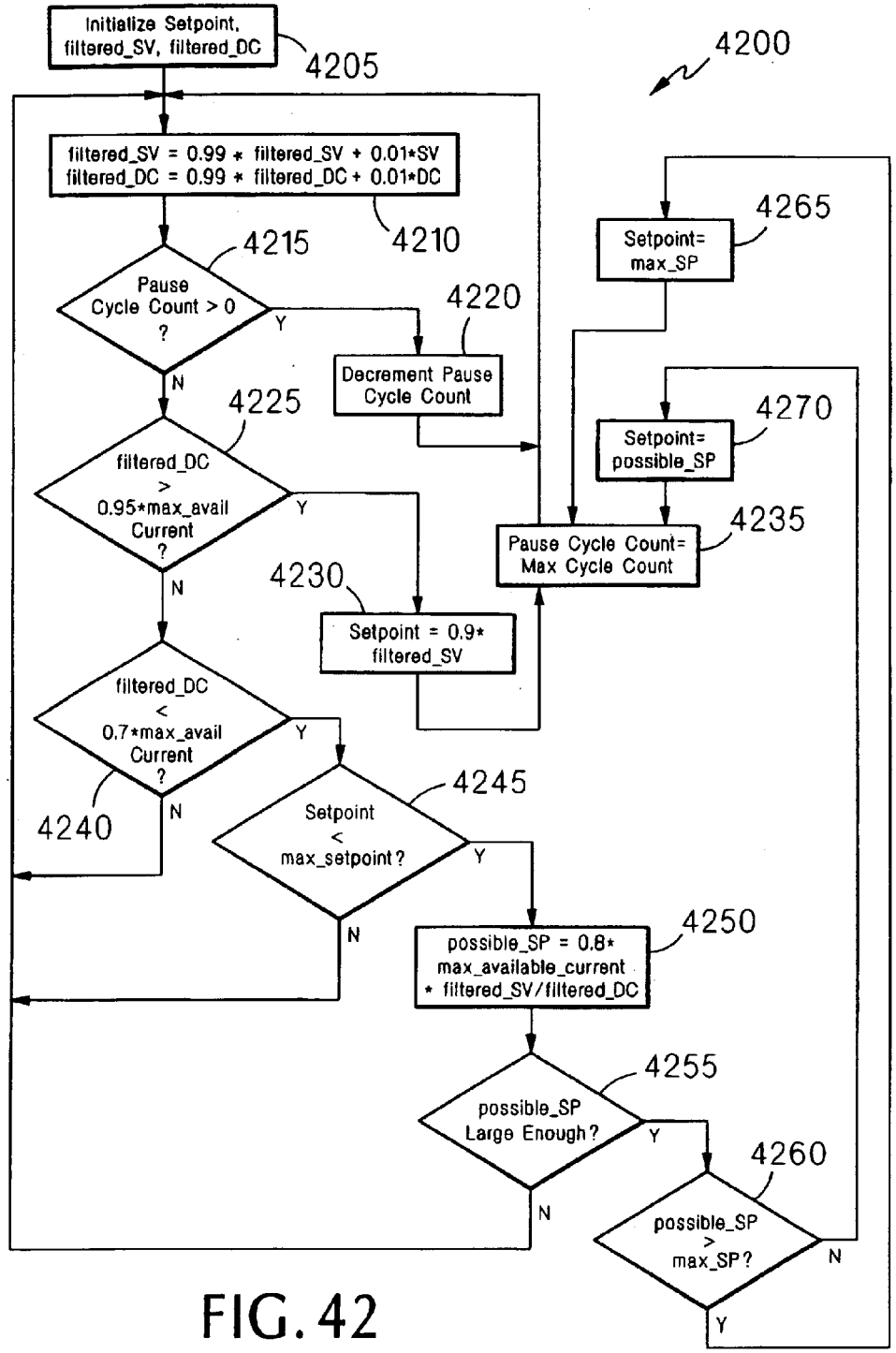
FIG. 42 is a flow chart of a setpoint control procedure.

Referring to FIG. 42, a control procedure 4200 implemented by the controller of the digital flowmeter may be used to select the highest sustainable setpoint given a maximum available current level. In general, the procedure is performed each time that a desired drive current output is selected, which typically is once per cycle, or once every half-cycle if interleaved cycles are used.

The controller starts by setting the setpoint to a default value (e.g., 0.3 V) and initializing filtered representations of the sensor voltage (filtered_SV) and the drive current (filtered_DC) (step 4205). Each time that the procedure is performed, the controller updates the filtered values based on current values for the sensor voltage (SV) and drive current (DC) (step 42 1 0). For example, the controller may generate a new value for filtered_SV as the sum of ninety nine percent of filtered_SV and one percent of SV.

Next, the controller determines whether the procedure has been paused to provide time for prior setpoint adjustments to take effect (step 4215). Pausing of the procedure is indicated by a pause cycle count having a value greater than zero. If the procedure is paused, the controller performs no further actions for the cycle and decrements the pause cycle count (step 4220).

If the procedure has not been paused, the controller determines whether the filtered drive current exceeds a threshold level (step 4225). In one implementation, the threshold level is ninety five percent of the maximum available current. If the current exceeds the threshold, the controller reduces the setpoint (step 4230). To allow time for the meter to settle after the setpoint change, the controller then implements a pause of the procedure by setting the pause cycle count equal to an appropriate value (e.g., 100) (step 4235).

If the procedure has not been paused, the controller determines whether the filtered drive current is less than a threshold level (step 4240) and the setpoint is less than a maximum permitted setpoint (step 4245). In one implementation, the threshold level equals seventy percent of the maximum available current. If both conditions are met, the controller determines a possible new setpoint (step 4250). In one implementation, the controller determines the new setpoint as eighty percent of the maximum available current multiplied by the ratio of filtered_SV to filtered_DC. To avoid small changes in the setpoint (i.e., chattering), the controller then determines whether the possible new setpoint exceeds the current setpoint by a sufficient amount (step 4255). In one implementation, the possible new setpoint must exceed the current setpoint by 0.02 V and by ten percent.

If the possible new setpoint is sufficiently large, the controller determines if it is greater than the maximum permitted setpoint (step 4260). If so, the controller sets the setpoint equal to the maximum permitted setpoint (step 4265). Otherwise, the controller sets the setpoint equal to the possible new setpoint (step 4270). The controller then implements a pause of the procedure by setting the pause cycle count equal to an appropriate value (step 4235).

Figure 43A:
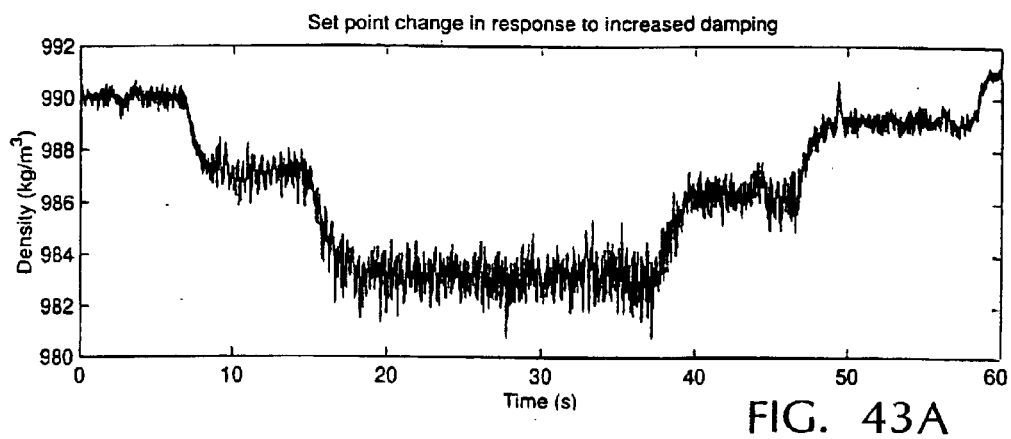
FIGS. 43A–43C are graphs illustrating application of the procedure of FIG. 41.
Figure 43B:
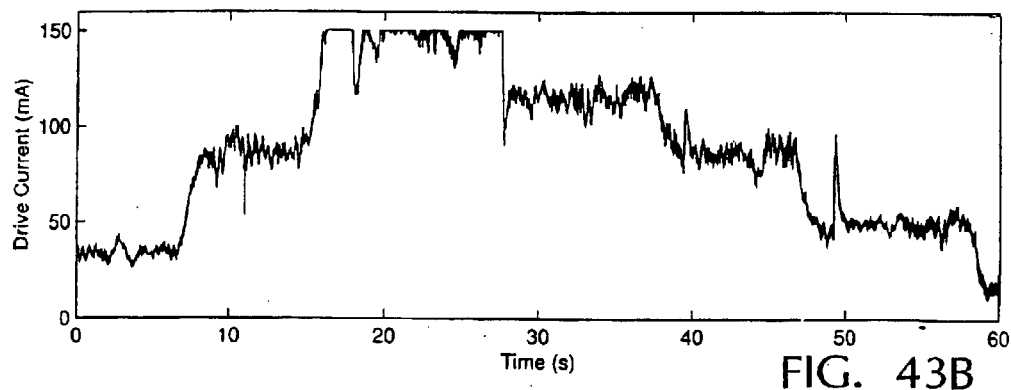
Figure 43C:
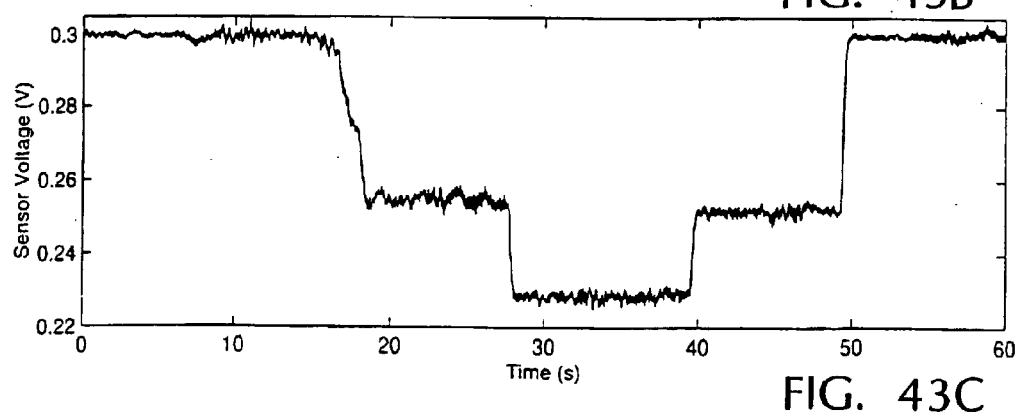

FIGS. 43A–43C illustrate operation of the setpoint adjustment procedure. As shown in FIG. 43C, the system starts with a setpoint of 0.3 V. At about eight seconds of operation, aeration results in a drop in the apparent density of the material in the conduit (FIG. 43A). Increased damping accompanying the aeration results in an increase in the drive current (FIG. 43B) and increased noise in the sensor voltage (FIG. 43C). No changes are made at this time, since the meter is able to maintain the desired setpoint.

At about fifteen seconds of operation, aeration increases and the apparent density decreases further (FIG. 43A). At this level of aeration, the driver current (FIG. 43B) reaches a maximum value that is insufficient to maintain the 0.3 V setpoint. Accordingly, the sensor voltage drops to 0.26 V (FIG. 43C), the voltage level that the maximum driver current is able to maintain. In response to this condition, the controller adjusts the setpoint (at about 28 seconds of operation) to a level (0.23 V) that does not require generation of the maximum driver current.

At about 38 seconds of operation, the level of aeration decreases and the apparent density increases (FIG. 43A). This results in a decrease in the drive current (FIG. 43B). At 40 seconds of operation, the controller responds to this condition by increasing the setpoint (FIG. 43C). The level of aeration decreases and the apparent density increases again at about 48 seconds of operation, and the controller responds by increasing the setpoint to 0.3 V.

K. Performance Results The digital flowmeter has shown remarkable performance improvements relative to traditional analog flowmeters. In one experiment, the ability of the two types of meters to accurately measure a batch of material was examined. In each case, the batch was fed through the appropriate flowmeter and into a tank, where the batch was then weighed. For 1200 and 2400 pound batches, the analog meter provided an average offset of 500 pounds, with a repeatability of 200 pounds. By contrast, the digital meter provided an average offset of 40 pounds, with a repeatability of two pounds, which clearly is a substantial improvement.

In each case, the conduit and surrounding pipework were empty at the start of the batch. This is important in many batching applications where it is not practical to start the batch with the conduit full. The batches were finished with the flowtube full. Some positive offset is expected because the flowmeter is measuring the material needed to fill the pipe before the weighing tank starts to be filled. Delays in starting up, or offsets caused by aerated flow or low amplitudes of oscillation, are likely to introduce negative offsets. For real batching applications, the most important issue is the repeatability of the measurement.

The results show that with the analog flowmeter there are large negative offsets and repeatability of only 200 pounds. This is attributable to the length of time taken to startup after the onset of flow (during which no flow is metered), and measurement errors until full amplitude of oscillation is achieved. By comparison, the digital flowmeter achieves a positive offset, which is attributable to filling up of the empty pipe, and a repeatability is two pounds.

Figure 44:
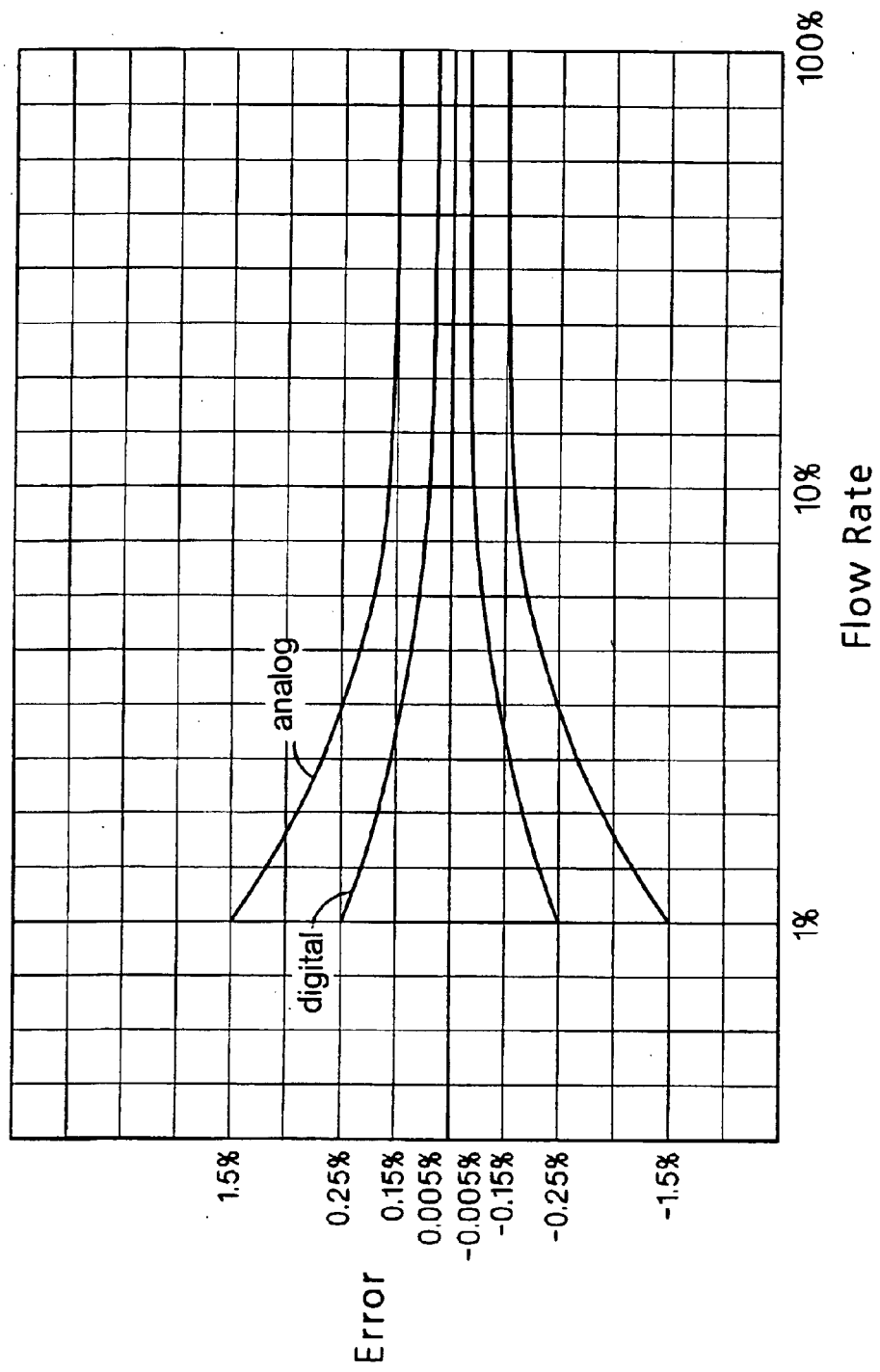
FIG. 44 is a graph comparing the performance of digital and analog flowmeters.

Another experiment compared the general measurement accuracy of the two types of meters. FIG. 44 illustrates the accuracy and corresponding uncertainty of the measurements produced by the two types of meters at different percentages of the meters' maximum recommended flow rate. At high flow rates (i.e., at rates of 25% or more of the maximum rate), the analog meter produces measurements that correspond to actual values to within 0.15% or less, compared to 0.005% or less for the digital meter. At lower rates, the offset of the analog meter is on the order of 1.5%, compared to 0.25% for the digital meter.

L. Self-Validating Meter

The digital flowmeter may used in a control system that includes self-validating sensors. To this end, the digital flowmeter may be implemented as a self-validating meter. Self-validating meters and other sensors are described in U.S. Pat. No. 5,570,300, entitled "SELF-VALIDATING SENSORS", which is incorporated by reference.

In general, a self-validating meter provides, based on all information available to the meter, a best estimate of the value of a parameter (e.g., mass flow) being monitored. Because the best estimate is based, in part, on nonmeasurement data, the best estimate does not always conform to the value indicated by the current, possibly faulty, measurement data. A self-validating meter also provides information about the uncertainty and reliability of the best estimate, as well as information about the operational status of the sensor. Uncertainty information is derived from known uncertainty analyses and is provided even in the absence of faults.

In general, a self-validating meter provides four basic parameters: a validated measurement value (VMV), a validated uncertainty (VU), an indication (MV status) of the status under which the measurement was generated, and a device status. The VMV is the meter's best estimate of the value of a measured parameter. The VU and the MV status are associated with the VMV. The meter produces a separate VMV, VU and MV status for each measurement. The device status indicates the operational status of the meter.

The meter also may provide other information. For example, upon a request from a control system, the meter may provide detailed diagnostic information about the status of the meter. Also, when a measurement has exceeded, or is about to exceed, a predetermined limit, the meter can send an alarm signal to the control system. Different alarm levels can be used to indicate the severity with which the measurement has deviated from the predetermined value.

VMV and VU are numeric values. For example, VMV could be a temperature measurement valued at 200 degrees and VU, the uncertainty of VMV, could be 9 degrees. In this case, there is a high probability (typically 95%) that the actual temperature being measured falls within an envelope around VMV and designated by VU (i.e., from 191 degrees to 209 degrees).

The controller generates VMV based on underlying data from the sensors. First, the controller derives a raw measurement value (RMV) that is based on the signals from the sensors. In general, when the controller detects no abnormalities, the controller has nominal confidence in the RMV and sets the VMV equal to the RMV. When the controller detects an abnormality in the sensor, the controller does not set the VMV equal to the RMV. Instead, the controller sets the VMV equal to a value that the controller considers to be a better estimate than the RMV of the actual parameter.

The controller generates the VU based on a raw uncertainty signal (RU) that is the result of a dynamic uncertainty analysis of the RMV. The controller performs this uncertainty analysis during each sampling period. Uncertainty analysis, originally described in "Describing Uncertainties in Single Sample Experiments," S. J. Kline & F. A. McClintock, *Mech. Eng.*, 75, 3–8 (1953), has been widely applied and has achieved the status of an international standard for calibration. Essentially, an uncertainty analysis provides an indication of the "quality" of a measurement. Every measurement has an associated error, which, of course, is unknown. However, a reasonable limit on that error can often be expressed by a single uncertainty number (ANSI/ASME PTC 19.1-1985 Part 1, Measurement Uncertainty: Instruments and Apparatus).

As described by Kline & McClintock, for any observed measurement M, the uncertainty in M, $w_M$, can be defined as follows:

$$M_{true} \in [M-w_M, M+w_M]$$

where M is true ($M_{true}$) with a certain level of confidence (typically 95%). This uncertainty is readily expressed in a relative form as a proportion of the measurement (i.e. $w_M/M$).

In general, the VU has a non-zero value even under ideal conditions (i.e., a faultless sensor operating in a controlled, laboratory environment). This is because the measurement produced by a sensor is never completely certain and there is always some potential for error. As with the VMV, when the controller detects no abnormalities, the controller sets the VU equal to the RU. When the controller detects a fault that only partially affects the reliability of the RMV, the controller typically performs a new uncertainty analysis that accounts for effects of the fault and sets the VU equal to the results of this analysis. The controller sets the VU to a value based on past performance when the controller determines that the RMV bears no relation to the actual measured value.

To ensure that the control system uses the VMV and the VU properly, the MV status provides information about how they were calculated. The controller produces the VMV and the VU under all conditions—even when the sensors are inoperative. The control system needs to know whether VMV and VU are based on "live" or historical data. For example, if the control system were using VMV and VU in feedback control and the sensors were inoperative, the control system would need to know that VMV and VU were based on past performance.

The MV status is based on the expected persistence of any abnormal condition and on the confidence of the controller in the RMV. The four primary states for MV status are generated according to Table 1.

TABLE 1

| Expected Persistence | Confidence in RMV | MV Status |
|---|---|---|
| not applicable | nominal | CLEAR |
| not applicable | reduced | BLURRED |
| short | zero | DAZZLED |
| long | zero | BLIND |

A CLEAR MV status occurs when RMV is within a normal range for given process conditions. A DAZZLED MV status indicates that RMV is quite abnormal, but the abnormality is expected to be of short duration. Typically, the controller sets the MV status to DAZZLED when there is a sudden change in the signal from one of the sensors and the controller is unable to clearly establish whether this change is due to an as yet undiagnosed sensor fault or to an abrupt change in the variable being measured. A BLURRED MV status indicates that the RMV is abnormal but reasonably related to the parameter being measured. For example, the controller may set the MV status to BLURRED when the RMV is a noisy signal. A BLIND MV status indicates that the RMV is completely unreliable and that the fault is expected to persist.

Two additional states for the MV status are UNVALIDATED and SECURE. The MV status is UNVALIDATED when the controller is not performing validation of VMV. MV status is SECURE when VMV is generated from redundant measurements in which the controller has nominal confidence.

The device status is a generic, discrete value summarizing the health of the meter. It is used primarily by fault detection and maintenance routines of the control system. Typically, the device status 32 is in one of six states, each of which indicates a different operational status for the meter. These states are: GOOD, TESTING, SUSPECT, IMPAIRED, BAD, or CRITICAL. A GOOD device status means that the meter is in nominal condition. A TESTING device status means that the meter is performing a self check, and that this self check may be responsible for any temporary reduction in measurement quality. A SUSPECT device status means that the meter has produced an abnormal response, but the controller has no detailed fault diagnosis. An IMPAIRED device status means that the meter is suffering from a diagnosed fault that has a minor impact on performance. A BAD device status means that the meter has seriously malfunctioned and maintenance is required. Finally, a CRITICAL device status means that the meter has malfunctioned to the extent that the meter may cause (or have caused) a hazard such as a leak, fire, or explosion.

Figure 45:
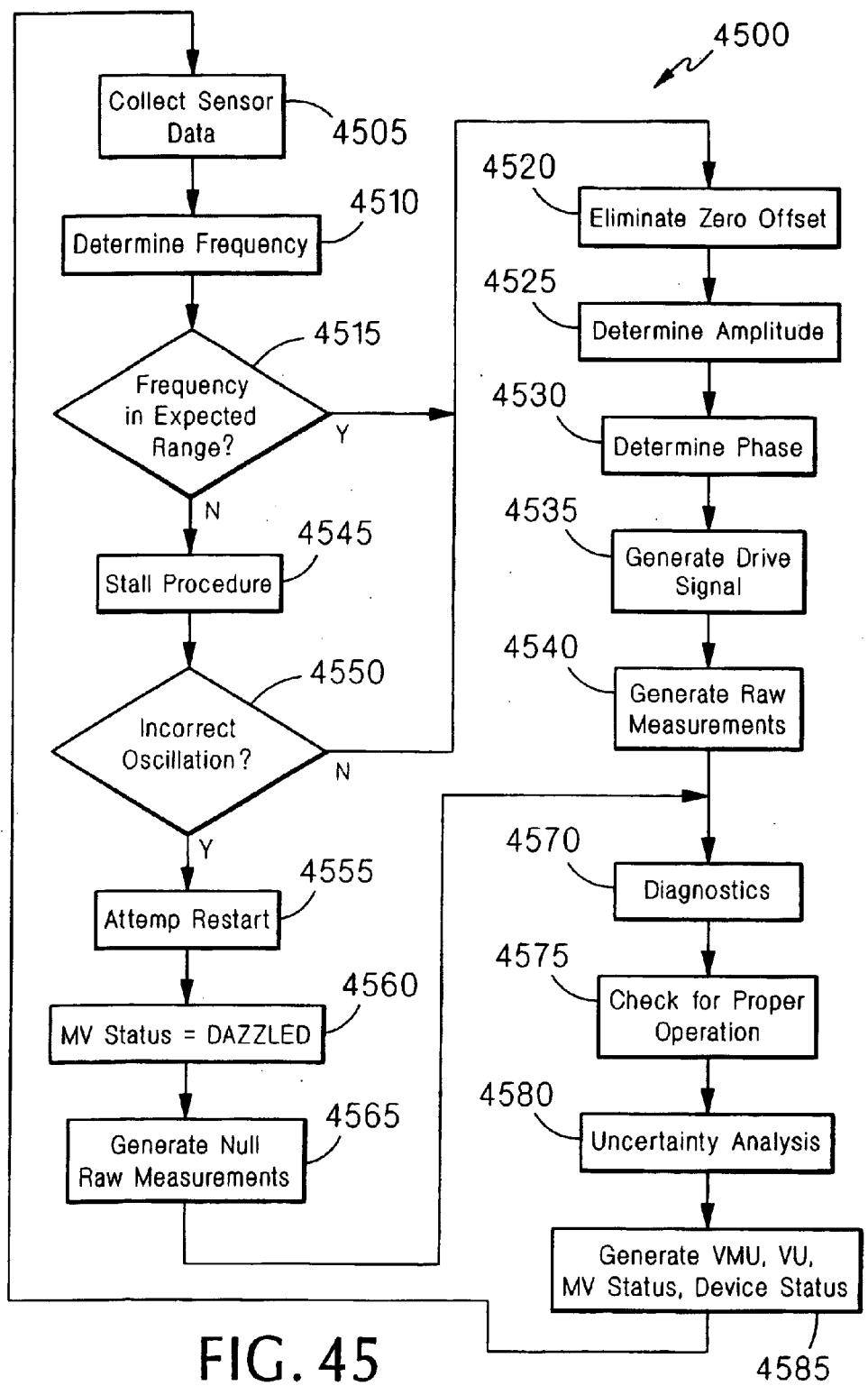
FIG. 45 is a flow chart showing operation of a self-validating meter.

FIG. 45 illustrates a procedure 4500 by which the controller of a self-validating meter processes digitized sensor signals to generate drive signals and a validated mass flow measurement with an accompanying uncertainty and measurement status. Initially, the controller collects data from the sensors (step 4505). Using this data, the controller determines the frequency of the sensor signals (step 4510). If the frequency falls within an expected range (step 4515), the controller eliminates zero offset from the sensor signals (step 4520), and determines the amplitude (step 4525) and phase (step 4530) of the sensor signals. The controller uses these calculated values to generate the drive signal (step 4535) and to generate a raw mass flow measurement and other measurements (step 4540).

If the frequency does not fall within an expected range (step 4515), then the controller implements a stall procedure (step 4545) to determine whether the conduit has stalled and to respond accordingly. In the stall procedure, the controller maximizes the driver gain and performs a broader search for zero crossings to determine whether the conduit is oscillating at all.

If the conduit is not oscillating correctly (i.e., if it is not oscillating, or if it is oscillating at an unacceptably high frequency (e.g., at a high harmonic of the resonant frequency)) (step 4550), the controller attempts to restart normal oscillation (step 4555) of the conduit by, for example, injecting a square wave at the drivers. After attempting to restart oscillation, the controller sets the MV status to DAZZLED (step 4560) and generates null raw measurement values (step 4565). If the conduit is oscillating correctly (step 4550), the controller eliminates zero offset (step 4520) and proceeds as discussed above.

After generating raw measurement values (steps 4540 or 4565), the controller performs diagnostics (step 4570) to determine whether the meter is operating correctly (step 4575). (Note that the controller does not necessarily perform these diagnostics during every cycle.)

Next, the controller performs an uncertainty analysis (step 4580) to generate a raw uncertainty value. Using the raw measurements, the results of the diagnostics, and other information, the controller generates the VMV, the VU, the MV status, and the device status (step 4585). Thereafter, the controller collects a new set of data and repeats the procedure. The steps of the procedure 4500 may be performed serially or in parallel, and may be performed in varying order.

In another example, when aeration is detected, the mass flow corrections are applied as described above, the MV status becomes blurred, and the uncertainty is increased to reflect the probable error of the correction technique. For example, for a flowtube operating at 50% flowrate, under normal operating conditions, the uncertainty might be of the order of 0.1–0.2% of flowrate. If aeration occurs and is corrected for using the techniques described above, the uncertainty might be increased to perhaps 2% of reading. Uncertainty values should decrease as understanding of the effects of aeration improves and the ability to compensate for aeration gets better. In batch situations, where flow rate uncertainty is variable (e.g. high at start/end if batching from/to empty, or during temporary incidents of aeration or cavitation), the uncertainty of the batch total will reflect the weighted significance of the periods of high uncertainty against the rest of the batch with nominal low uncertainty. This is a highly useful quality metric in fiscal and other metering applications.

M. Two Wire Flowmeter

Figure 46:
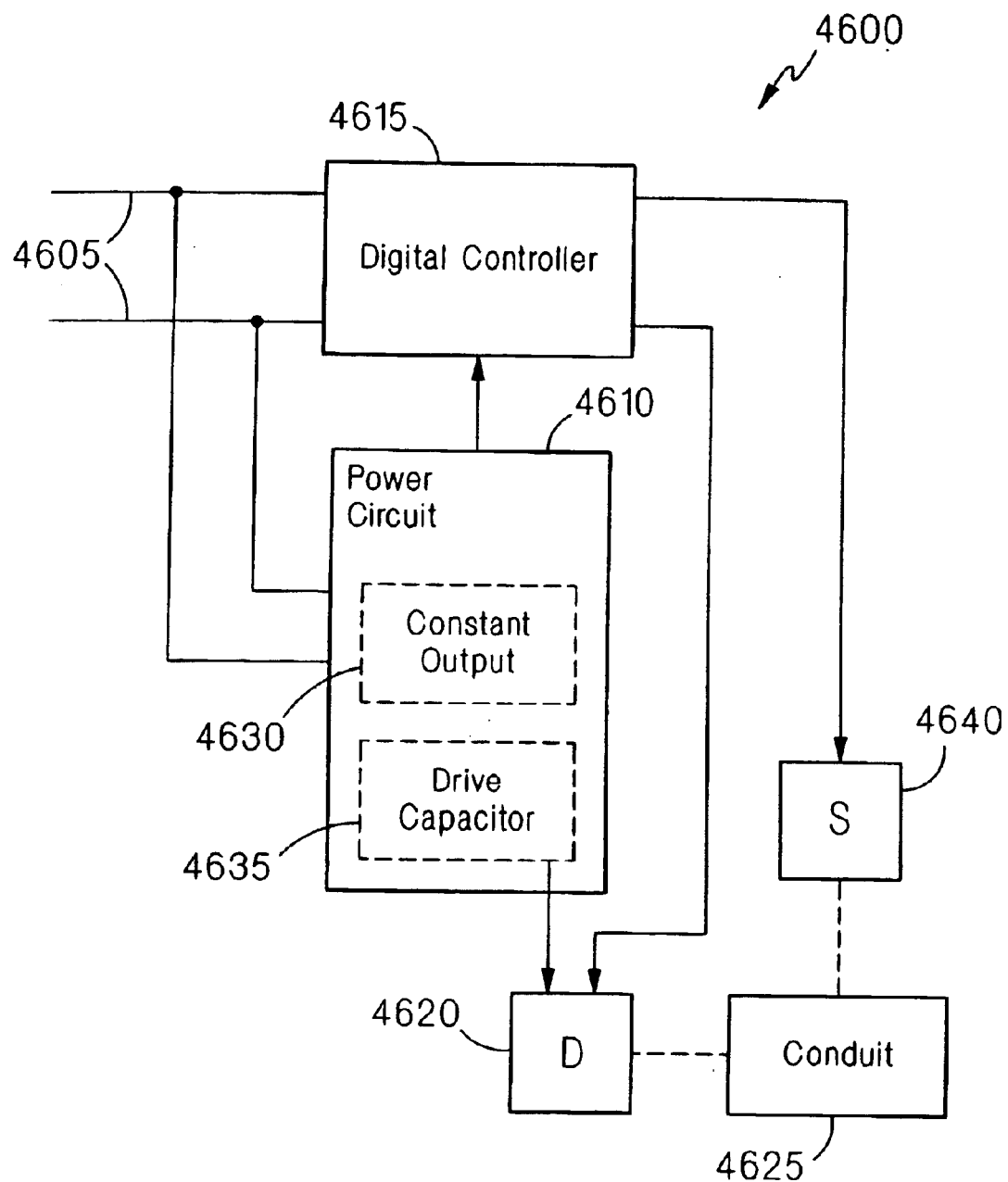
FIG. 46 is a block diagram of a two-wire digital mass flowmeter.

Other embodiments are also contemplated. For example, as shown in FIG. 46, the techniques described above may be used to implement a "two-wire" Coriolis flowmeter 4600 that performs bidirectional communications on a pair of wires 4605. A power circuit 4610 receives power for operating a digital controller 4615 and for powering the driver(s) 4620 to vibrate the conduit 4625. For example, the power circuit may include a constant output circuit 4630 that provides operating power to the controller and a drive capacitor 4635 that is charged using excess power. The power circuit may receive power from the wires 4605 or from a second pair of wires. The digital controller receives signals from one or more sensors 4640.

When the drive capacitor is -suitably charged, the controller 4615 discharges the capacitor 4635 to drive the conduit 4625. For example, the controller may drive the conduit once during every 10 cycles. The controller 4615 receives and analyzes signals from the sensors 4640 to produce a mass flow measurement that the controller then transmits on the wires 4605.

A number of implementations have been described. Nevertheless, it will be understood that various modifications may be made. Accordingly, other implementations are within the scope of the following claims.

What is claimed is:

1. A controller for a flowmeter comprising:
an input module operable to receive a sensor signal from a sensor connected to a vibratable flowtube, the sensor signal related to a fluid flow through the flowtube;
a signal processing system operable to receive the sensor signal, determine sensor signal characteristics, and output drive signal characteristics for a drive signal applied to the flowtube;
an output module operable to output the drive signal to the flowtube; and
a control system operable to modify the drive signal and thereby maintain oscillation of the flowtube during a time in which an apparent density of the fluid flow, as determined by the signal processing system based on the sensor signal characteristics, drops by more than ten percent in response to an introduction of gas within the fluid flow.

2. The controller of claim 1 wherein the control system is operable to maintain oscillation of the flowtube during a time in which the apparent density drops by more than fifteen percent in response to the introduction of gas within the fluid flow.

3. The controller of claim 1 wherein the control system is operable to maintain oscillation of the flowtube during a time in which the apparent density drops by more than twenty percent in response to the introduction of gas within the fluid flow.

4. The controller of claim 1 wherein the control system is operable to modify the drive signal by increasing a drive gain applied to the drive signal in response to a reduction of the apparent density.

5. The controller of claim 4 wherein the drive gain is defined as a ratio of a driver current of the drive signal to an amplitude of oscillation of the flowtube.

6. The controller of claim 4 wherein the drive gain is defined as a ratio of a driver current of the drive signal to a sensor voltage of the sensor signal.

7. The controller of claim 4 wherein the control system is operable to increase the drive gain by a factor of ten times.

8. The controller of claim 4 wherein the control system is operable to increase the drive gain by a factor of twenty times.

9. The controller of claim 1 wherein a volumetric fraction of the fluid flow comprising introduced gas is 5% or more.

10. A method for operating a flowmeter comprising:
receiving a sensor signal from a sensor connected to a vibratable flowtube, the sensor signal related to a fluid flow through the flowtube;
processing the sensor signal to determine sensor signal characteristics,
determining, based on the sensor signal characteristics, drive signal characteristics for a drive signal applied to the flowtube, the drive signal characteristics including a drive gain;
determining, based on the sensor signal characteristics, a flow transition characterized by the drive gain rising in conjunction with a reduction in an apparent density of the fluid flow; and
transitioning the flowmeter from a first state in which a substantially non-aerated fluid flow exists in the flowtube to a second state in which an aerated fluid flow exists in the flowtube, based on the flow transition.

11. The method of claim 10 wherein determining drive signal characteristics comprises determining a first-state drive gain associated with the first state.

12. The method of claim 11 comprising maintaining oscillation of the flowtube when a second-state drive gain used for driving the flowtube in the second state is more than ten times the first-state drive gain.

13. The method of claim 12 wherein the second-state drive gain is more than twenty times the first-state drive gain.

14. The method of claim 10 wherein the determining the flow transition occurs during a reduction in apparent density of greater than ten percent.

15. The controller of claim 10 wherein the drive gain is defined as a ratio of a drive current of the drive signal to an amplitude of oscillation of the flowtube.

16. The controller of claim 10 wherein the drive gain is defined as a ratio of a drive current of the drive signal to a sensor voltage of the sensor signal.

17. The method of claim 10 wherein a volumetric fraction of the aerated fluid flow comprising gas is 5% or more.

18. A flowmeter comprising:
a vibratable conduit conducting a fluid flow;
a driver connected to the conduit and operable to impart a motion to the conduit;
a sensor connected to the conduit and operable to sense the motion of the conduit; and
a control and measurement system connected to the driver and the sensor, the control and measurement system comprising circuitry to:
receive a first sensor signal from the sensor during a non-aerated fluid flow through the conduit;
generate, based on the first sensor signal and using digital signal processing, a first drive signal having a drive frequency, the first drive signal having a drive gain based on the first sensor signal;
receive a second sensor signal from the sensor upon introduction of gas to the fluid flow, the gas comprising more than five percent by volume of a total fluid flow;
generate a second drive signal based on the second sensor signal and using digital signal processing; and
update the drive gain in response to the introduction of the gas at a drive gain update rate,
wherein the drive gain update rate is at least five percent of the drive frequency.

19. The flowmeter of claim 18 wherein the control and measurement system is operable to update the drive gain incrementally, each increment occurring at the drive gain update rate.

20. The flowmeter of claim 18 wherein the drive gain update rate is at least ten percent of the drive frequency.

21. The flowmeter of claim 18 wherein the drive gain update rate is at least twenty percent of the drive frequency.

22. The flowmeter of claim 18 wherein the drive gain update rate is at least fifty percent of the drive frequency.

23. The flowmeter of claim 18 wherein the drive gain update rate is at least equal to the drive frequency.

24. The flowmeter of claim 18 further comprising:
an analog-to-digital converter operable to convert the sensor signal received from the sensor from analog form to digital form; and
a digital-to-analog converter operable to convert the drive signal from digital form to analog form, for application to the conduit via the driver.

25. A controller for a flowmeter comprising:
an input module operable to receive a sensor signal from a sensor connected to a vibratable flowtube, the sensor signal related to a fluid flow through the flowtube;
a signal processing system operable to receive the sensor signal, determine sensor signal characteristics using digital signal processing, and output drive signal characteristics for a drive signal applied to the flowtube, the drive signal characteristics including a drive gain to be applied to the drive signal;
a control system operable to modify the drive signal and thereby maintain oscillation of the flowtube at a determined oscillation frequency, wherein the drive gain is modified in response to a change in condition of the fluid flow, as necessary to maintain the oscillation of the flowtube, such that the drive gain incrementally changes at least once per forty cycles of the oscillation frequency; and
an output module operable to output the drive signal to the flowtube.

26. The controller of claim 25 wherein the oscillation frequency corresponds to a natural frequency of vibration of the flowtube.

27. The controller of claim 25 wherein the drive gain is modified in response to a change in condition of the fluid flow, as necessary to maintain the oscillation of the flowtube, such that the drive gain incrementally changes at least once per twenty cycles of the oscillation frequency.

28. The controller of claim 25 wherein the drive gain is modified in response to a change in condition of the fluid flow, as necessary to maintain the oscillation of the flowtube, such that the drive gain incrementally changes at least once per ten cycles of the oscillation frequency.

29. The controller of claim 25 wherein the drive gain is modified in response to a change in condition of the fluid flow, as necessary to maintain the oscillation of the flowtube, such that the drive gain incrementally changes at least once per five cycles of the oscillation frequency.

30. The controller of claim 25 wherein the drive gain is modified in response to a change in condition of the fluid flow, as necessary to maintain the oscillation of the flowtube, such that the drive gain incrementally changes at least once per cycle of the oscillation frequency.

31. A flowmeter comprising:
a vibratable conduit;
a driver connected to the conduit and operable to impart a motion to the conduit;

a sensor connected to the conduit and operable to sense the motion of the conduit; and a control and measurement system connected to the driver and the sensor, the control and measurement system comprising circuitry to:

receive a first sensor signal from the sensor at a first mass flow rate of fluid through the conduit;

generate, based on the first sensor signal, a measurement output characterizing a property of the fluid;

receive a second sensor signal from the sensor upon a change of the first mass flow rate to a second mass flow rate; and update, based on the second sensor signal, the measurement output at an update rate that is at least five percent of an oscillation frequency of the conduit.

32. The flowmeter of claim 31 wherein the measurement output includes a pulse output of the flowmeter.

33. The flowmeter of claim 31 wherein the measurement output includes a 4–20 mA output of the flowmeter.

34. The flowmeter of claim 31 wherein the property of the fluid includes a mass flow rate of the fluid.

35. The flowmeter of claim 31 wherein the property of the fluid includes a density of the fluid.

36. The flowmeter of claim 31 wherein the update rate is at least ten percent of the oscillation frequency of the conduit.

37. The flowmeter of claim 31 wherein the update rate is at least twenty percent of the oscillation frequency of the conduit.

38. The flowmeter of claim 31 wherein the update rate is at least fifty percent of the oscillation frequency of the conduit.

39. The flowmeter of claim 31 wherein the update rate is greater than or equal to the oscillation frequency of the conduit.

40. A controller for a flowmeter comprising:

an input module operable to receive a sensor signal from a sensor connected to a flowtube oscillating at an oscillation frequency, the sensor signal related to a flow of a fluid through the flowtube;

a signal processing system operable to receive the sensor signal, determine sensor signal characteristics using digital signal processing, and output a measurement output characterizing a property of the fluid flow; and a control system operable to modify the measurement output in response to a change in condition of the fluid flow, to thereby obtain a modified measurement output, wherein a response time between the change in condition of the fluid flow and an outputting of the modified measurement output is less than 100 ms.

41. The controller of claim 40 wherein the update rate is less than 50 ms.

42. The controller of claim 40 wherein the update rate is less than 30 ms.

43. The flowmeter of claim 40 wherein the measurement output includes a pulse output of the flowmeter.

44. The flowmeter of claim 40 wherein the measurement output includes a 4–20 mA output of the flowmeter.

45. The flowmeter of claim 40 wherein the property of the fluid includes a mass flow rate of the fluid.

46. The flowmeter of claim 40 wherein the property of the fluid includes a density of the fluid.

* * * * *